US011325875B2

(12) United States Patent
Ding et al.

(10) Patent No.: US 11,325,875 B2
(45) Date of Patent: May 10, 2022

(54) COMPOUND HAVING CHIRAL SPIROBIINDANE SKELETON AND PREPARATION METHOD THEREFOR

(71) Applicants: ZHEJIANG JIUZHOU PHARMACEUTICAL CO., LTD., Taizhou (CN); SHANGHAI INSTITUTE OF ORGANIC CHEMISTRY, CHINESE ACADEMY OF SCIENCES, Shanghai (CN)

(72) Inventors: Kuiling Ding, Shanghai (CN); Yuxi Cao, Shanghai (CN); Zhiyao Zheng, Shanghai (CN); Qinglei Chong, Shanghai (CN); Zheng Wang, Shanghai (CN)

(*) Notice: Subject to any disclaimer, the term of this patent is extended or adjusted under 35 U.S.C. 154(b) by 0 days.

(21) Appl. No.: 16/060,424

(22) PCT Filed: Dec. 12, 2016

(86) PCT No.: PCT/CN2016/109383
§ 371 (c)(1),
(2) Date: Jun. 8, 2018

(87) PCT Pub. No.: WO2017/107789
PCT Pub. Date: Jun. 29, 2017

(65) Prior Publication Data
US 2018/0370876 A1 Dec. 27, 2018

(30) Foreign Application Priority Data
Dec. 22, 2015 (CN) .......................... 201510974151.1

(51) Int. Cl.
*C07C 13/72* (2006.01)
*B01J 31/22* (2006.01)
(Continued)

(52) U.S. Cl.
CPC ............... *C07C 13/72* (2013.01); *B01J 31/22* (2013.01); *C07B 53/00* (2013.01); *C07C 39/17* (2013.01);
(Continued)

(58) Field of Classification Search
None
See application file for complete search history.

(56) References Cited

FOREIGN PATENT DOCUMENTS

| CN | 1342652 A | | 4/2002 |
| CN | 1827563 | * | 9/2006 |
| CN | 102424682 A | | 4/2012 |

OTHER PUBLICATIONS

Venugopal et al. (Tetrahedron: Asymmetry, 2004, 15(21), 3427). (Year: 2004).*
Tetrahedron:Asymmetry, 15(21), (2004),3427-3431.

* cited by examiner

Primary Examiner — Sudhakar Katakam
Assistant Examiner — Jennifer C Sawyer
(74) Attorney, Agent, or Firm — Novick, Kim & Lee, PLLC; Allen Xue

(57) ABSTRACT

Chiral spirobiindane skeleton compound and preparation method thereof is disclosed in the present invention. The spirobiindane skeleton compound of the present invention having the structure formula of I or I'; the preparation method for synthesizing the spirobiindane skeleton compound of the present invention comprising the following steps: in the presence of solvent and catalysts, the structure formula compound III reacted through intramolecular Friedel-Crafts reaction to obtain the compound of formula I; the catalyst is a Browsteric acidor Lewis acid. The preparation method of chiral fused spirobiindane skeleton compound of the present invention does not need to adopt chiral starting (Continued)

materials or chiral resolving agents, does not require chiral resolving steps, is simple in method, is simple in post-treatment, and is economic and environment friendly. High product yield, high product optical purity and chemical purity. The catalyst for the asymmetric reaction is obtained from the chiral spirobiindane skeleton ligand of the present invention, under the catalytic reagent of transition metal, the catalyzed hydrogenation reaction can arrive at a remarkable catalytic effect with a product yield of >99%, and a product ee value of up to >99%.

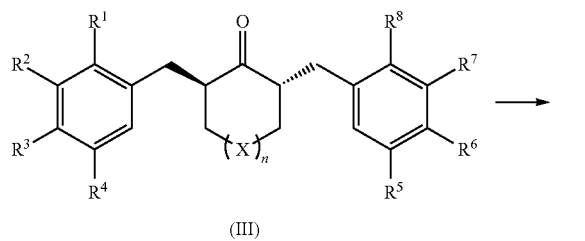

(III)

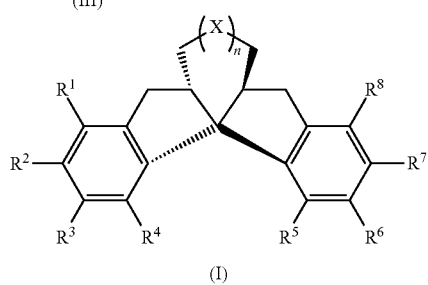

(I)

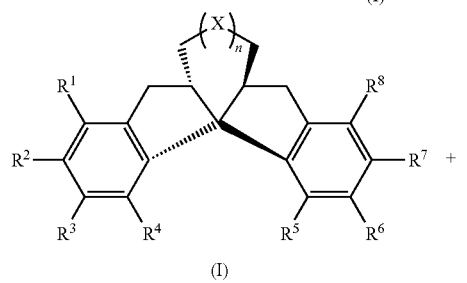

(I)

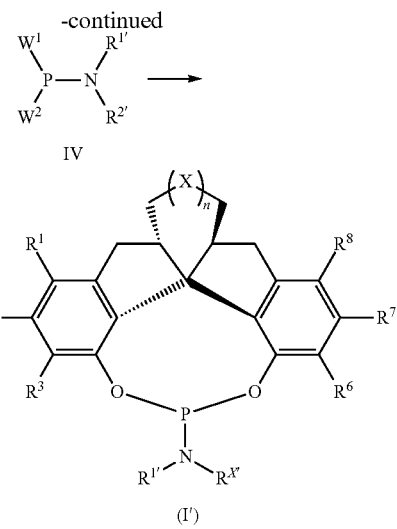

11 Claims, 1 Drawing Sheet

(51) Int. Cl.
    *C07C 39/17*     (2006.01)
    *C07C 43/21*     (2006.01)
    *C07C 43/225*     (2006.01)
    *C07F 9/6571*     (2006.01)
    *C07B 53/00*     (2006.01)
    *C07C 231/12*     (2006.01)
    *C07C 233/51*     (2006.01)

(52) U.S. Cl.
    CPC ............ *C07C 43/21* (2013.01); *C07C 43/225* (2013.01); *C07C 231/12* (2013.01); *C07C 233/51* (2013.01); *C07F 9/6571* (2013.01)

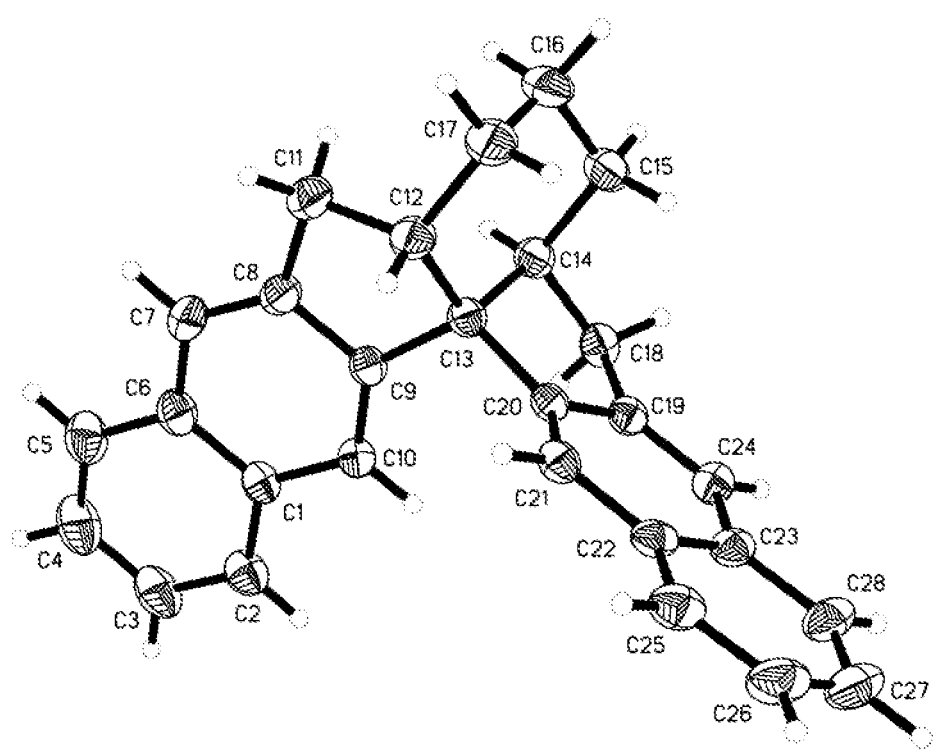

COMPOUND HAVING CHIRAL SPIROBIINDANE SKELETON AND PREPARATION METHOD THEREFOR

This application is a national entry of International Application No. PCT/CN2016/109383, filed on Dec. 12, 2016, which claims priority of Chinese patent application submitted to the Chinese Patent Office on Dec. 22, 2015, with the application number 201510974151.1, and entitled "Chiral spirobiindane skeleton compound and preparation method thereof". All of its contents are incorporated in this application by reference.

FIELD OF THE INVENTION

The present invention specifically relates to chiral spirobiindane skeleton compound and preparation method thereof.

BACKGROUND OF THE INVENTION

Compounds containing chiral spiro structure with all carbon atoms substituted are a special class of chiral molecules, namely chiral spiro-alkanes. In the structure of these spiro-alkanes, the chemical bonding of the spiro carbon atom has a characteristic of tetrahedral orientation, and its two rings are in two planes close to each other perpendicularly, and the rigid structure limits free rotate of the two rings in spirocyclic compounds, so when the ring contains a substituent, it has an axial chirality. Spirane compounds containing structures of all-carbon spiro-ring are important structural units of some biologically active compounds,and are existed extensively in natural products such as β-veivone, acorenone B, phentermromycin, etc. (Referential references R. Rios, Chem. Soc. Rev. 2012, 41, 1060.). In addition, two rings in the spiro-alkane molecule are connected to a quaternary carbon center through a σ-bond, so the chiral spiro compounds are relatively rigid and are not easily racemized. Therefore, the spiro-alkanes having the above advantages are an ideal class of chiral ligands, and has been greatly developed in the synthesis and asymmetric catalysis of chiral ligands in the last decade. For example, several outstanding chiral ligands represented by chiral spiroindane skeleton ligands have been shown better stereochemical controling effect and catalytic effect than other chiral skeletons in various types of asymmetric catalytic reactions in recent years, which are considered to be "privileged structures" for chiral ligands in the current field of asymmetric catalysis (S.-F. Zhu, Q.-L. Zhou, in Privileged Chiral Ligands and Catalysts, Ed.: Q.-L. Zhou, Wiley-VCH, Weinheim, 2011, pp. 137-170.). However, the current synthesis of chiral spiro-alkanes is usually quite cumbersome (review literature: [1] M. Sannigrahi, Tetrahedron 1999, 55, 9007; [2] R. Pradhan et al, Tetrahedron 2006, 62, 779; [3] S. Kotha et al, Synthesis 2009, 165; [4] V. A. D'yakonov et al, Chem. Rev. 2014, 114, 5775.), Not only does the substrate have a limited range of applications, but in most cases only racemic products can be obtained. Most of the optically pure spiro-alkane molecules are obtained by the racemic or diastereomeric resolution process, which is costly and cumbersome to operate, and also brings about environmental pollution, thus greatly limiting its practical application. Currently, there are more than a hundred chiral ligands and catalysts based on spirobiindane skeleton. Most of them are synthesized by using optically pure (R)- or (S)-1,1'-spiroindane-7,7'-diol or its derivatives as the chiral starting materials ([1] Zhou, Qilin; Fu, Yu; Xie, Jianhua; Wang, Lixin; Zhou, Hai. CN 1342652 A; [2] Zhou, Qilin; Xie, Jianhua; Cheng, Xu; Fu, Yu; Wang, Lixin. CN 1439643 A; [3] Zhou, Qilin; Duan, Haifeng; Shi, Wenjian; Wang, Lixin; Xie, Jianhua. CN 1760198 A. [4] Zhou, Qilin; Hou, Guohua; Xie, Jianhua; Wang, Lixin. CN 1887893 A; [5] Zhou, Qilin; Zhu, Shoufei; Li, Shen; Wang, Lixin; Song, Song. WO 2009129700 A1; [6] Zhou, Qilin; Xie, Jianhua; Liu, Xiaoyan; Xie, Jianbo; Wang, Lixin. WO 2012065571 A1; [7] XUFENG LING, YANYAN ZHAO, HAIJUN QU, XUEJIAN LICN 102516302 A.). So far, the original chirality of such an optically pure spiroindane skeleton, optically pure (R)- or (S)-1,1'-spiroindane-7,7'-diol or ester, without exception, are obtained by chiral resolution methods such as diastereomeric chemical derivatization or chiral inclusion crystallization (review the literature: [1] V. B. Birman et al, Tetrahedron-Asymmetry 1999, 10, 125; [2] J. H. Zhang et al, Tetrahedron-Asymmetry 2002, 13, 1363; [3] Z. Li et al, Tetrahedron-Asymmetry 2004, 15, 665; [4] M. Venugopal et al, Tetrahedron-Asymmetry 2004, 15, 3427.), The isolation process is cumbersome and complicated to operate, costs large amounts of chiral resolving reagents, and is not economical and environmentally friendly. These disadvantages lead to high costs of the ligands, and cause difficulties in large-scale preparation, thereby limiting their application to some extent.

Therefore, the development of a highly efficient asymmetric catalysis, without using of chiral resolving reagents, and without chiral resolving steps needed. Also simple methods, simple post-treatment, economic and environmental-friendly, high product yield, and high product optical purity and chemical purity method of chiral fused spirobiindane skeleton compounds are needed. Also the development of a chiral catalyst containing a chiral fused spirobiindane skeleton ligand having a high catalytic activity are problems urgently to be solved in the field.

SUMMARY OF THE INVENTION

The technical problem to be solved by the present invention is to overcome disadvantages existing in the preparation of chiral fused spirobiindane skeleton compounds in the prior art. The disadvantages are lised as follows: expensive chiral starting materials or chiral resolving agents are used; chiral resolving steps are needed, the cumbersome procedure, the high cost of raw materials and processes, the poor economic and environmental defects, and the low catalytic efficiency of the asymmetric hydrogenation catalyst in the prior art. Thus it is objected to provide a chiral spirobiindane skeleton compound and a preparation method thereof. The preparation method of chiral fused spirobiindane skeleton compound of the present invention does not need to adopt chiral starting materials or chiral resolving agents, does not require chiral resolving steps, is simple in method, is simple in post-treatment, and is economic and environment friendly. High product yield, high product optical purity and chemical purity. The catalyst for the asymmetric reaction is obtained from the chiral spirobiindane skeleton ligand of the present invention, under the catalytic reagent of transition metal, the catalyzed hydrogenation reaction can arrive at a remarkable catalytic effect with a product yield of >99%, and a product ee value of up to >99%.

First Technical Method of the Present Invention:

The present invention provides chiral fused spirobiindane skeleton compounds as shown in Formula I, or their enantiomers or diastereomers;

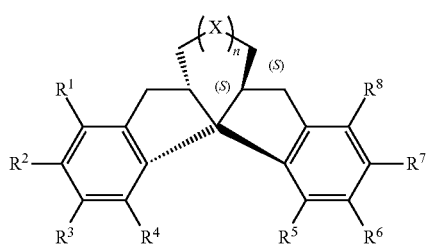

(I)

Wherein $R^1$, $R^2$, $R^3$, $R^4$, $R^5$, $R^6$, $R^7$ and $R^8$ are each independently hydrogen, $C_1$~$C_{10}$ alkyl, $C_3$~$C_{10}$ cycloalkyl, $C_1$~$C_4$ alkoxy, aryl, fluorine, chlorine, bromine, iodine, or hydroxyl;

Alternatively, $R^1$, $R^4$, $R^5$ and $R^8$ are each independently hydrogen, $C_1$~$C_{10}$ alkyl, $C_3$~$C_{10}$ cycloalkyl, $C_1$~$C_4$ alkoxy, aryl, fluorine, chlorine, bromine, iodine, or hydroxy; $R^2$ and $R^3$ together linked with its carbon atom of the molecular skeleton which they are attached to form an aromatic ring, and the aromatic ring is fused with the phenyl ring which the molecular skeleton carbon atoms located and that $R^2$ and $R^3$ linked to form mergered ring structure; $R^6$ and $R^7$ together linked with its carbon atom of the molecular skeleton which they are attached to form an aromatic ring, and the aromatic ring is fused with the phenyl ring which the molecular skeleton carbon atoms located and that $R^6$ and $R^7$ linked to form mergered ring structure;

X is $CY^1Y^2$, $NY^1$, O or S; n=0~3; Wherein $Y^1$ and $Y^2$ are each independently selected from H, $C_1$~$C_{10}$ alkyl, $C_3$~$C_{10}$ cycloalkyl, aryl or $C_1$~$C_4$ alkoxy; And, the chiral spirobiindane skeleton compound of formula I, not having the structure of formula I-n;

I-n

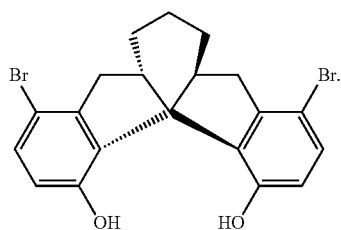

Preferably, $R^1$ and $R^8$ are the same. Preferably, $R^2$ and $R^7$ are the same. Preferably, $R^3$ and $R^6$ are the same. Preferably, $R^4$ and $R^5$ are the same.

Preferably, when $R^1$, $R^2$, $R^3$, $R^4$, $R^5$, $R^6$, $R^7$ and $R^8$ are each independently a $C_1$~$C_{10}$ alkyl, the $C_1$~$C_{10}$ alkyl group is a $C_1$~$C_6$ alkyl group. Preferably, when $R^1$, $R^2$, $R^3$, $R^4$, $R^5$, $R^6$, $R^7$ and $R^8$ are each independently a $C_1$~$C_6$ alkyl, the $C_1$~$C_6$ alkyl group is a $C_1$~$C_3$ alkyl group. Preferably, when $R^2$, $R^3$, $R^4$, $R^5$, $R^6$, $R^7$ and $R^8$ are each independently a $C_1$~$C_3$ alkyl group, the $C_1$~$C_3$ alkyl group is methyl, ethyl or propyl.

Preferably, when $R^1$, $R^2$, $R^3$, $R^4$, $R^5$, $R^6$, $R^7$ and $R^8$ are each independently a $C_3$~$C_{10}$ cycloalkyl, the $C_3$18 $C_{10}$ cycloalkyl group is a $C_3$~$C_6$ cycloalkyl group. Preferably, when $R^1$, $R^2$, $R^3$, $R^4$, $R^5$, $R^6$, $R^7$ and $R^8$ are each independently a $C_3$~$C_6$ cycloalkyl, the $C_3$~$C_6$ cycloalkyl group of is cyclopropyl.

Preferably, when $R^1$, $R^2$, $R^3$, $R^4$, $R^5$, $R^6$, $R^7$ and $R^8$ are each independently a $C_1$~$C_4$ alkoxy group, the $C_1$~$C_4$ alkoxy group is a $C_1$~$C_3$ alkoxy group. Preferably, when $R^1$, $R^2$, $R^3$, $R^4$, $R^5$, $R^6$, $R^7$ and $R^8$ are each independently $C_1$~$C_3$ alkoxy, the $C_1$~$C_3$ alkoxy group is methoxy, ethoxy or propoxy.

Preferably, when $R^1$, $R^2$, $R^3$, $R^4$, $R^5$, $R^6$, $R^7$ and $R^8$ are each independently an aryl group, the aryl group is a $C_6$~$C_{20}$ aryl group. Preferably, the $C_6$~$C_{20}$ aryl group is a $C_6$~$C_{12}$ aryl group. Preferably, the $C_6$~$C_{12}$ aryl is phenyl or naphthyl.

Preferably, $R^2$ and $R^3$ together with the carbon atoms on the molecular skeleton to which they are attached are connected together into an aromatic ring, the aromatic ring is a $C_6$~C20 aromatic ring. Preferably, the $C_6$~$C_{20}$ aromatic ring is a $C_6$~$C_{12}$ aromatic ring. Preferably, the $C_6$~$C_{12}$ aromatic ring is a benzene ring or a naphthalene ring.

Preferably, $R^6$ and $R^7$ together linked with its carbon atom of the molecular skeleton which they are attached to form a $C_6$~$C_{20}$ aromatic ring the aromatic ring is a $C_6$~$C_{20}$ aromatic ring. Preferably, the $C_6$~$C_{20}$ aromatic ring is a $C_6$~$C_{12}$ aromatic ring. Preferably, the $C_6$~$C_{12}$ aromatic ring is a benzene ring or a naphthalene ring.

Preferably, said n=0, 1, 2 or 3.

Preferably, when $Y^1$ and $Y^2$ are each independently a $C_1$~$C_{10}$ alkyl group, the $C_1$~$C_{10}$ alkyl group is a C1~C4 alkyl group. Preferably, the C1~C4 alkyl is methyl, ethyl, propyl, or tert-butyl.

Preferably, when $Y^1$ and $Y^2$ are each independently a $C_3$~$C_{10}$ cycloalkyl group, the $C_3$~$C_{10}$ cycloalkyl group is a $C_3$~$C_6$ cycloalkyl group. Preferably, the $C_3$~$C_6$ cycloalkyl is cyclopropyl.

Preferably, when the $Y^1$ and $Y^2$ are each independently an aryl group, the aryl group is a $C_6$~$C_{20}$ aryl group. Preferably, the $C_6$~C20 aryl group is a $C_6$~$C_{12}$ aryl group. Preferably, the $C_6$~$C_{12}$ aryl is phenyl or naphthyl.

Preferably, when $Y^1$ and $Y^2$ are each independently a $C_1$~$C_4$ alkoxy group, the $C_1$~$C_4$ alkoxy group is a methoxy group or an ethoxy group.

Preferably, the chiral spiroindane skeleton compound represented by formula I is any one of the following compounds:

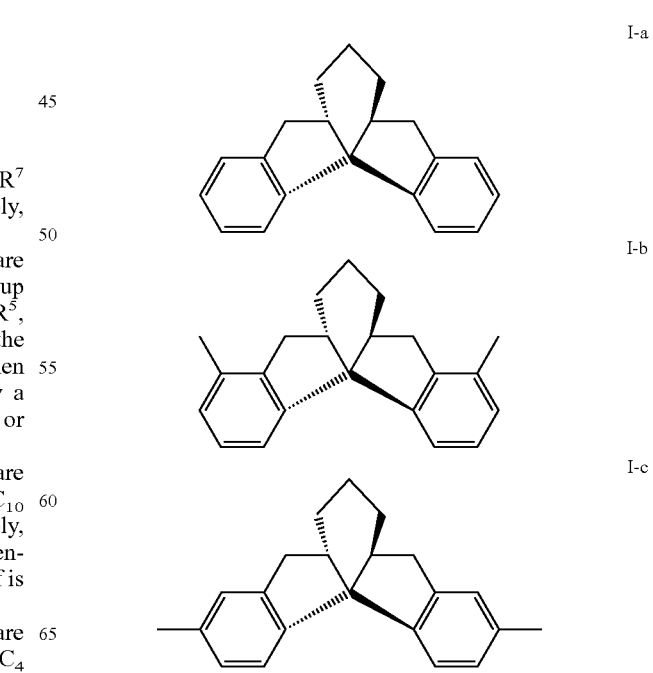

I-d
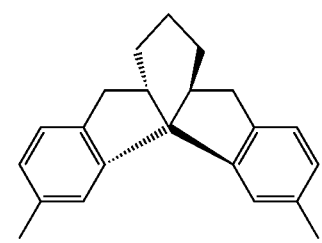
I-e
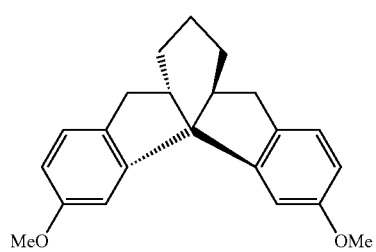
I-f
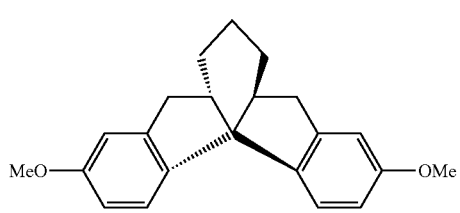
I-g
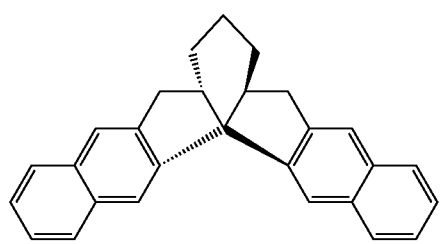
I-h
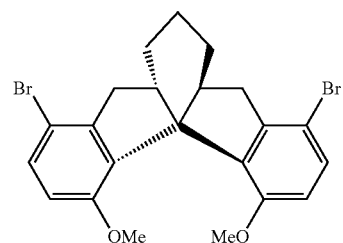
I-i
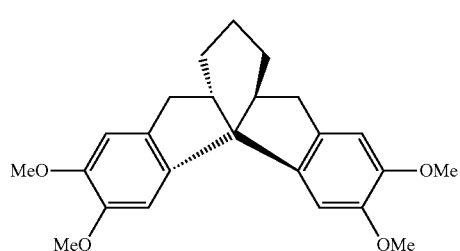
I-j
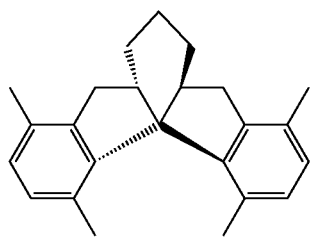
I-k
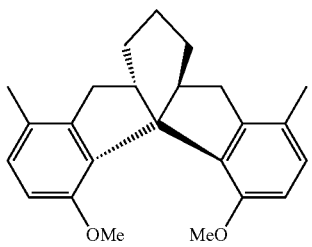
I-l
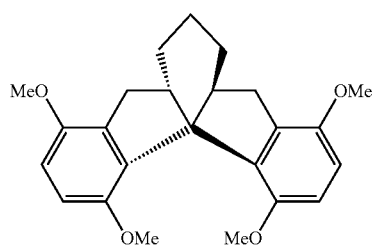
I-m
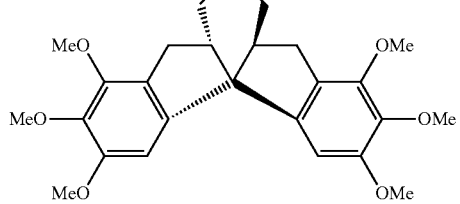
I-o
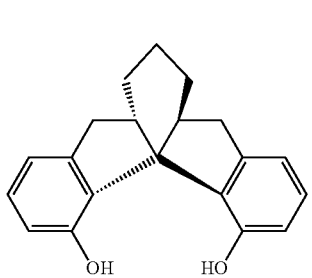
I-p
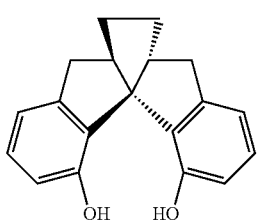

-continued

I-q
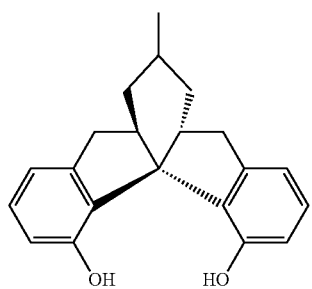

I-r
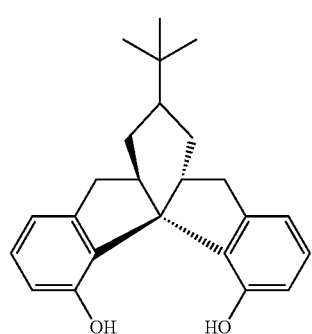

I-s
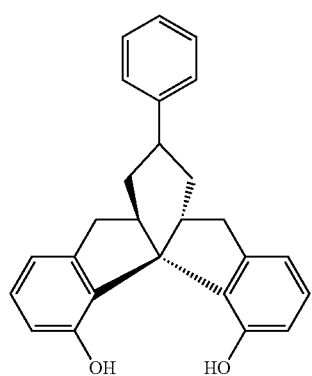

ent-I-o
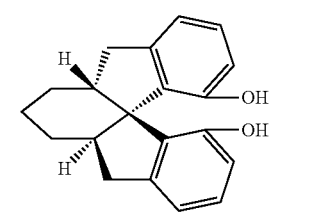

I-q'
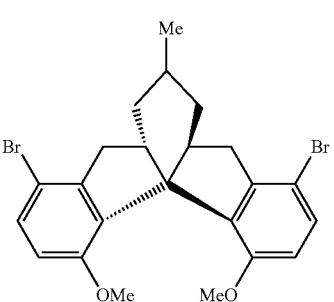

-continued

I-r'
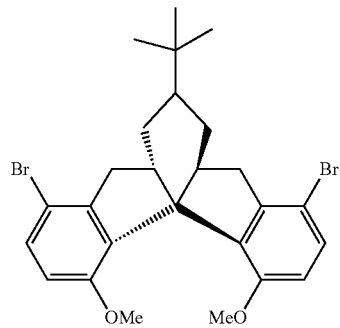

I-s'
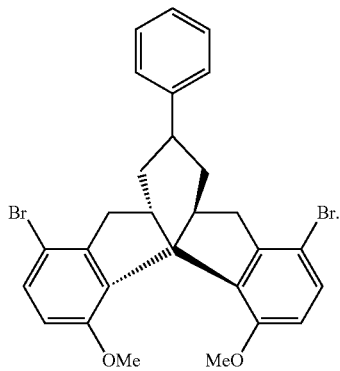

Second technical method of the present invention:

The present invention also provides a phosphoramidite ligand as shown in Formula I', or their enantiomers or diastereomers;

(I')
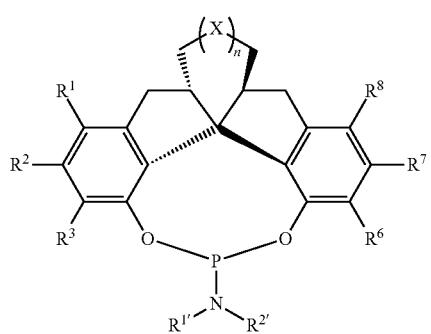

The X, n, $R^1$, $R^2$, $R^3$, $R^6$, $R^7$ and $R^8$ are as described as above.

$R^{1'}$ and $R^{2'}$ are each independently a $C_1$~$C_{10}$ alkyl group or a $C_3$~$C_{10}$ cycloalkyl group; or $R^{1'}$ and $R^{2'}$ together linked with its nitrogen atom which they are attached to form a $C_2$~$C_{10}$ N-hetero alkyl.

Preferably, when $R^{1'}$ and $R^{2'}$ are each independently a $C_1$~$C_{10}$ alkyl group, $C_1$~$C_{10}$ alkyl group is a $C_1$~$C_3$ alkyl group. Preferably, when $R^{1'}$ and $R^{2'}$ are each independently a $C_1$~$C_3$ alkyl group, the $C_1$~$C_3$ alkyl group is a methyl group, an ethyl group, or a propyl group.

Preferably, when $R^{1'}$ and $R^{2'}$ are each independently a $C_3$~$C_{10}$ cycloalkyl group, $C_3$~$C_{10}$ cycloalkyl group is a $C_3$~$C_6$ cycloalkyl group. Preferably, when $R^{1'}$ and $R^{2'}$ are each independently a $C_3$~$C_6$ cycloalkyl group, the $C_3$~$C_6$ cycloalkyl group is a cyclopropyl group.

Preferably, the $C_2$~$C_{10}$ N-hetero alkyl ring is a $C_3$~$C_6$ N-hetero alkyl ring. Preferably, the $C_3$~$C_6$ N-hetero alkyl ring is tetrahydropyrazolidine.

Preferably, the phosphoramidite ligand represented by Formula I' is any one of the following:

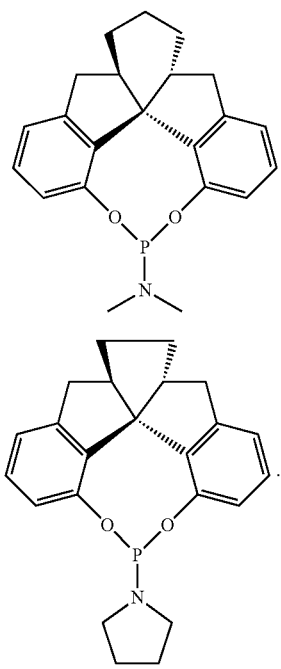

I-t

I-u

The third technical method of the present invention:

The present invention also provides a method for preparing the compound represented by Formula I, which comprises the following steps: in a solvent and in the presence of a catalyst, the compound represented by Formula III is subjected to an intramolecular Friedel-Crafts reaction to obtain compounds of the formula I; the catalyst is a Browsteric acidor Lewis acid; X, n, $R^1$, $R^2$, $R^3$, $R^4$, $R^5$, $R^6$, $R^7$ and $R^8$ are the same as previously described;

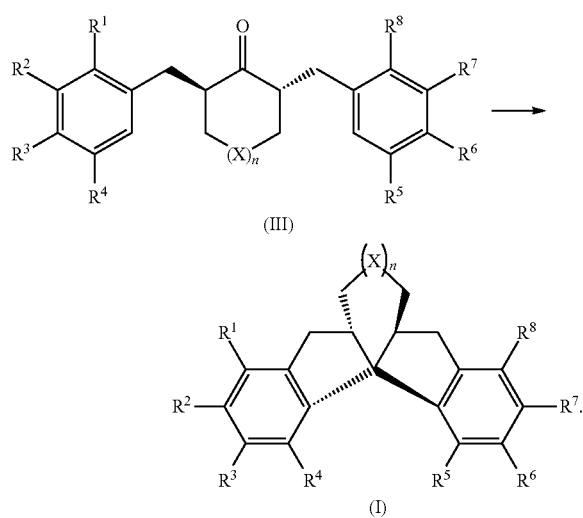

Preferably, the Browsteric acid is selected from one of hydrochloric acid, phosphoric acid, polyphosphoric acid, methanesulfonic acid, trifluoromethanesulfonic acid, acetic acid, trifluoroacetic acid, p-toluenesulfonic acid and phosphotungstic acidor selected from the mixture of them.

Preferably, the Lewis acid is selected from one of scandium trifluoromethanesulfonate, aluminum trichloride, tin tetrachloride, iron trichloride, boron trifluoride, titanium tetrachloride, titanium tetraisopropoxide, and indium trifluoromethylsulfonate and copper triflateor selected from the mixture of them.

More preferably, the Lewis acid is titanium tetrachloride.

Preferably, the method for preparing the compound represented by the formula I further comprises the following steps: mixing the solvent and the compound represented by the formula III, adding the catalyst at 0° C. and the reaction is performed for 1~100 minutes (preferably 30 minutes), naturally warms up to 15° C.~40° C. (preferably 25° C.) and continues for 1~20 hours (preferably 5~6 hours).

The addition to the catalyst is preferably a dropwise addition; more preferably a slow addition. The rate of drop acceleration of the slow addition is 0.1 mL/min~1.5 mL/min (preferably 0.5 mL/min).

The 0° C. condition is preferably achieved by ice bath cooling.

Preferably, the reaction continuely being carried out under stirring conditions.

Preferably, the intramolecular Friedel-Crafts reaction is performed under anhydrous and anaerobic conditions.

Preferably, the intramolecular Friedel-Crafts reaction is performed under protective gas conditions. The protective gas can be a conventional protective gas for such reactions in the art, and is preferably argon and/or nitrogen.

Preferably, the molar ratio of the compound represented by the formula III to the catalyst is in the range of 100:1~1:100; more preferably 2:1~1:10; for example, 1:4~1:1, Another example is 1:2.

The solvent of the intramolecular Friedel-Crafts reaction may be a common solvent for such reactions in the art. Preferably, the solvent of the intramolecular Friedel-Crafts reaction is one of an aromatic hydrocarbon solvent, a halogenated hydrocarbon solvent, an ether solvent, an alcohol solvent, an amide solvent, and a sulfoxide solvent or selected from the mixture of them. Preferably, the aromatic hydrocarbon solvent is one of benzene, toluene and xylene or selected from the mixture of them. Preferably, the halogenated hydrocarbon solvent is one of dichloromethane, chloroform, carbon tetrachloride and 1,2-dichloroethane or selected from the mixture of them. Preferably, the ether solvent is diethyl ether and/or tetrahydrofuran. Preferably, the alcoholic solvent is methanol and/or ethanol. Preferably, the amide solvent is N,N-dimethylformamide. Preferably, the sulfoxide solvent is dimethyl sulfoxide.

Preferably, the molar volume ratio of the compound of the formula III to the solvent of the molecular Friedel-Crafts reaction is in the range of 0.02 mol/L~0.2 mol/L, such as 0.05 mol/L or 0.1 mol/L.

The temperature of the intramolecular Friedel-Crafts reaction can be a conventional temperature according to the reaction temperature suitable for the type of this kind of reaction in the art, and is preferably −40° C.~100° C., more preferably 0-40° C., and optimally 0~25° C.; for example 5, 10 or 25° C.

In the method for preparing the compound represented by Formula I, the progress of the intramolecular Friedel-Crafts reaction can be monitored by conventional test methods (such as TLC, HPLC, GC or NMR) in the art. When the compound represented by Formula III disappears, the reaction reaches end point, the time of the intramolecular Friedel-Crafts reaction is preferably 0.1~48 hours; more preferably 1~24 hours; for example, 0.5~12 hours; For example, 2 hours, 4 hours, 5 hours, 5.5 hours, 6 hours, 6.5 hours, 8 hours, 10 hours, 12 hours, or 20 hours.

In the method for preparing the compound represented by the formula I, after the intramolecular Friedel-Crafts reaction is completed, preferably, the post-treatment operation can be further included. The method and conditions for the post-treatment can be conventional methods and conditions for post-treatment of such reactions in the art. Preferably, the reaction is quenched, extracted, dried, filtered, and concentrated. The quenching is preferably water quenching. The amount of water used is preferably 0.4~0.5 times the volume of the reaction solvent. The extractant for extraction is preferably a halogenated hydrocarbon solvent; the halogenated hydrocarbon solvent is preferably dichloromethane. The volume ratio of the extracted extractant to the reaction solvent in a single extraction is 0.5 to 10. The extraction is preferably performed three times. The dried desiccant is preferably anhydrous sodium sulfate. The concentration is preferably vacuum distillation.

In the method for preparing a compound represented by the formula I, after the intramolecular Friedel-Crafts reaction is completed, preferably, a column chromatography step can be further included. The column chromatography is preferably performed using a silica gel column. The column chromatography eluent is preferably a mixture of petroleum ether and an ester solvent. In the mixed liquid of the petroleum ether and the ester solvent, the volume of the petroleum ether and the ester solvent is preferably 1:100 to 100:1 (more preferably, 50:1). The ester solvent is preferably ethyl acetate.

Preferably, the method for preparing the compound represented by the formula III comprises the following steps: in the solvent and in the presence of the catalyst, between the compound of the formula II reacted with hydrogen through asymmetric hydrogenation reaction to obtain the Compounds as shown in Formula III;

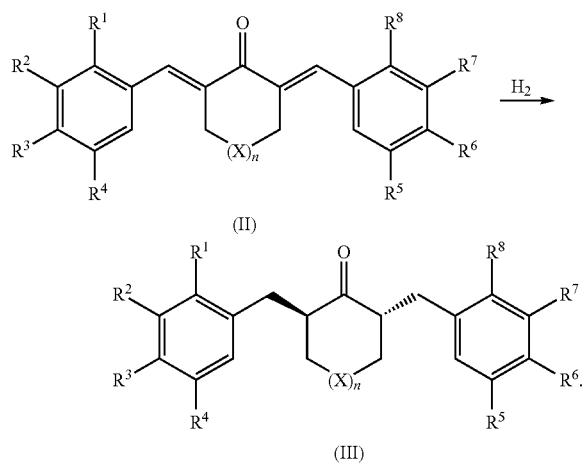

In the method for preparing the compound represented by Formula III, the asymmetric hydrogenation catalyst may be a conventional asymmetric hydrogenation catalyst for reactions of this type in the art, and is preferably selected from one of a transition metal of ruthenium, rhodium, iridium, and palladium,or selected from the mixture of them; the metal complex is chiral or unchiral; more preferably a phosphine-nitrogen ligand complex of ruthenium. Preferably, the phosphine-nitrogen ligand complex of rhodium is a chiral phosphine-nitrogen ligand complex of Ir. Preferably, the chiral phosphine-nitrogen ligand complex of Ir is a chiral monovalent rhodium/phosphine-oxazoline complex. The monovalent iridium/phosphine-oxazoline complex is preferably selected from one of IrI/(S)-tBu-PHOX, Ir$^I$/(R,S)-Bn-SpinPHOX and Ir$^I$/(S,S)-Bn-SpinPHOX and their respective enantiomers or diastereomers,or selected from the mixture of them:

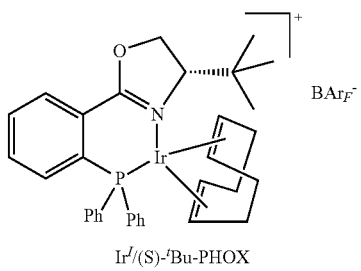

Ir$^I$/(S)-$^t$Bu-PHOX

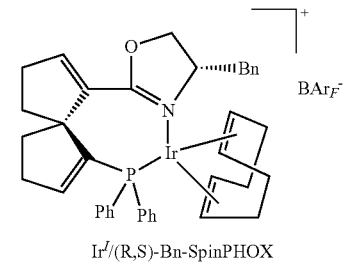

Ir$^I$/(R,S)-Bn-SpinPHOX

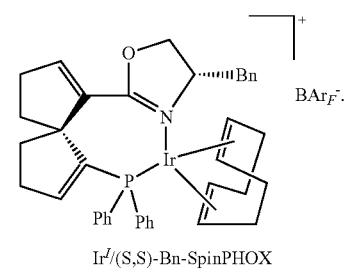

Ir$^I$/(S,S)-Bn-SpinPHOX

In the method for preparing the compound represented by Formula I, preferably, the molar ratio of the asymmetric hydrogenation catalyst to the compound represented by Formula II is in the range of 0.0001~0.1; more preferably 0.005~0.02; optimally 0.01 to 0.02.

In the method for preparing the compound represented by Formula I, the solvent for the asymmetric hydrogenation reaction may be a conventional solvent for such reactions in the art, and it is preferably selected from one of a halogenated hydrocarbon solvent, an aromatic hydrocarbon solvent, and an ether, an alcohol solvent, an amide solvent, and a sulfoxide solvent, or selected from the mixture of them. Preferably, the halogenated hydrocarbon solvent is selected from one of dichloromethane, chloroform, carbon tetrachloride and 1,2-dichloroethane,or selected from the mixture of them. Preferably, the aromatic hydrocarbon solvent is one of benzene, toluene and xylene, or selected from the mixture of them. Preferably, the ether solvent is diethyl ether and/or tetrahydrofuran. Preferably, the alcoholic solvent is methanol and/or ethanol. Preferably, the amide solvent is N,N-dimethylformamide. Preferably, the sulfoxide solvent is dimethyl sulfoxide.

In the method for preparing the compound represented by Formula I, the volume-to-mass ratio of the solvent for asymmetric hydrogenation and the compound represented by Formula II is 1 ml/g to 20 ml/g, for example, 12.0 ml/g~50 ml/g, for example 12.5 ml/g.

In the method for preparing the compound represented by Formula I, the pressure of hydrogen in the asymmetric hydrogenation reaction may be the conventional pressure in this type of reaction in the field; preferably, 1~100 atm; more preferably 30~50 atm.

In the method for preparing the compound represented by Formula I, the temperature of the asymmetric hydrogenation reaction may be the conventional temperature in this type of reaction in the field, preferably −78 to 80° C.; more preferably 10 to 35° C.

In the method for preparing the compound represented by Formula I, the progress of the asymmetric hydrogenation reaction may be monitored by a conventional test method in the art (such as TLC, HPLC, GC, or NMR), generally as shown in Formula II. When the compound shown to be disappeared, the reaction reaches end point, the reaction time of asymmetric hydrogenation is preferably 1~48 hours; more preferably 6~12 hours; for example, 6~8 hours.

The method for preparing the compound represented by the formula I may preferably further comprises a post-treatment operation after the asymmetric hydrogenation reaction is completed. The methods and conditions of post-treatment can be conventional methods and conditions for such post-reaction treatment in the art, and are preferably: concentration and column chromatography. The concentration is preferably vacuum distillation. The column chromatography is preferably a silica gel column. The column chromatography eluting agent is preferably a mixture of petroleum ether and an ester solvent having a volume ratio of 1:100~100:1 (for example, 20). Preferably, the ester solvent is ethyl acetate.

Preferably, the method for preparing the compound represented by the formula I, after the asymmetric hydrogenation reaction is ended, without performing post-treatment, and directly mixing the reaction system and the Friedel-Crafts reaction solvent, the catalyst and the compound shown in Formula III and subjected to the intramolecular Friedel-Crafts reaction.

Preferably, the method for preparing the compound represented by the formula II, comprises the following steps: the compound represented by the formula V, the formula VI and the formula VII is subjected to aldol condensation reaction as shown below in the solvent to prepared the compound as shown in Formula II;

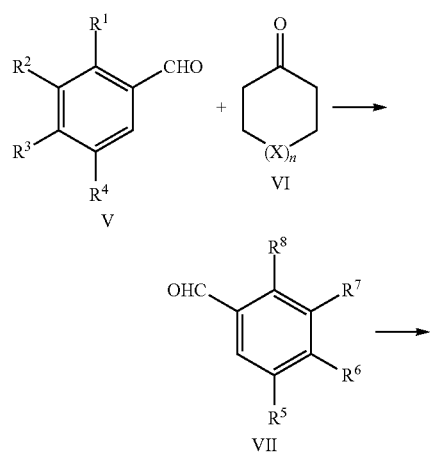

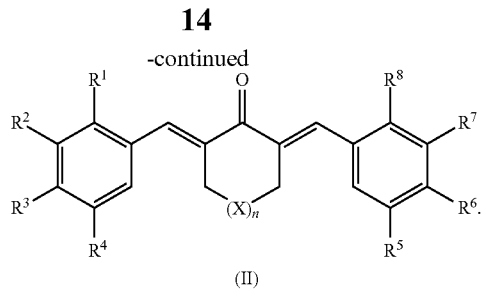

In the method for preparing the compound represented by Formula I, the method and conditions for the aldol condensation reaction can be conventional methods and conditions for such reactions in the art, and the present invention prefers to use the following conditions:

Preferably, the aldol condensation reaction is performed under alkaline condition.

Preferably, the alkaline condition is to add an inorganic base. Preferably, the inorganic base is as described above.

Preferably, the aldol condensation reaction solvent is a mixture of an alcohol solvent and water. Preferably, the alcohol solvent is selected from one of methanol, ethanol and propanol, or selected mixture of them. Preferably, among the mixture solvent of acohol with water, the volume ratio of alcohol solvent to water is in the range of 1:1~1:10.

Preferably, the molar ratio of the solvent of the aldol condensation reaction to the compound of the formula VI is 10000 ml/mol ~1 ml/mol.

Preferably, the reaction temperature of aldol condensation is 10~35° C.

In the method for preparing the compound represented by Formula II, the progress of the aldol condensation reaction can be monitored by a conventional test method in the art (such as TLC, HPLC, GC or NMR), generally When the compound represented by VI disappearing, the reaction reaches end point, the time of substitution reaction is preferably 1~12 hours (for example, 10 hours).

In the method for preparing the compound represented by the formula II, preferably, after the aldol condensation reaction is completed, an post-treatment operation can be further included. The methods and conditions of post-treatment can be conventional methods and conditions for such post-reaction treatment in the art, and preferably as following: filtration, washing, and drying. The filtration is preferably suction filtration. The washing is preferably first washed with water and then washed with an alcoholic solvent such as ethanol.

The fourth technical method of the present invention:

The present invention also provides a method for preparing a compound as shown in Formula I', which comprises the following steps: the compound represented by Formula I and the compound represented by Formula IV is subjected to substitution reaction in a solvent under alkaline condition to produce a compound of formula I'; W1 and W2 are each independently halogen; X, n, $R^1$, $R^2$, $R^3$, $R^4$, $R^5$, $R^6$, $R^7$, $R^8$, $R^{1'}$ and $R^{2'}$ are described as previous;

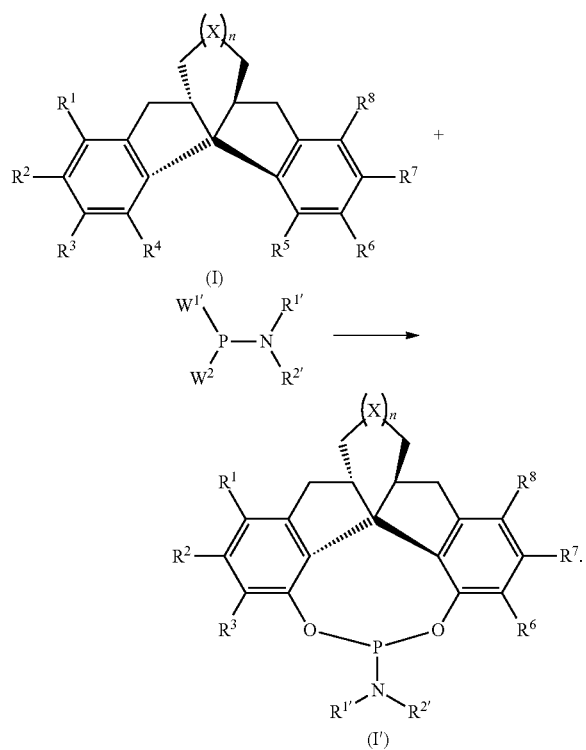

Preferably, in the substitution reaction, the halogen is preferably fluorine, chlorine, bromine or iodine.

Preferably, in the substitution reaction, the $C_1$~$C_{10}$ alkyl is a $C_1$~$C_6$ alkyl; more preferably, is a $C_1$~$C_3$ alkyl. Preferably, the $C_1$~$C_3$ alkyl is methyl, ethyl or propyl.

The method and conditions for the substitution reaction can be conventional methods and conditions in the art, and the present invention prefers to use the following conditions:

Preferably, the method for preparing the compound represented by the formula I' comprises the following steps: under alkaline conditions, the compound represented by the formula I is mixed with the solvent, and is cooled to −40~10° C. Then, the compound is mixed with the compound represented by the formula IV, and the substitution reaction is performed after the temperature is raised to 10 to 35° C.

Preferably, the method of mixing with the compound represented by the formula IV is to add the compound represented by the formula IV to the reaction system. Preferably, the adding method is dropping. The dropping is preferred to be slow.

Preferably, the substitution reaction is carried out under stirring conditions.

Preferably, the substitution reaction is carried out under anhydrous and anaerobic conditions.

Preferably, the substitution reaction is carried out under protective gas conditions. Preferably, the protective gas is argon and/or nitrogen.

Preferably, the alkaline condition is that the reaction is performed under the action of an alkali. Preferably, the base is an organic alkali and/or an inorganic alkali. Preferably, the organic alkali is selected from one of pyridines, imidazoles, pyrazines, anthraquinones, purines, morpholines, piperidines, piperazines, tertiary amines, anilines, and guanidine organic alkali, or selected from the mixture of them. Preferably, the tertiary amine organic base is selected from one of trimethylamine, triethylamine, tributylamine, N-ethyldiisopropylamine and N,N-dimethylbenzylamine,or selected from the mixture of them. Preferably, the aniline organic base is N,N-dimethylaniline. Preferably, the pyridine organic base is selected from one of pyridine, picoline, ethylmethylpyridine, 4-dimethylaminopyridine and 2-methyl-5-ethylpyridine, or selected from the mixture of them. Preferably, the piperidine organic base is N-methylpiperidine. Preferably, the morpholine organic base is N-methylmorpholine. Preferably, the piperazine organic base is 1,4-ethylene piperazine (DABCO). Preferably, the steroid organic base is 1,8-diazabicyclo[5.4.0]undec-7-ene (DBU) and/or 1,5-diazabicyclo[4.3.0] non-5-ene (DBN). Preferably, the inorganic base is selected from one of an alkali metal or alkaline earth metal hydride, an alkali metal or alkaline earth metal hydroxide, an alkali metal or alkaline earth metal alkoxide, an alkali metal or alkaline earth metal amide, an alkali metal or alkaline earth metal carbonates, alkali metal or alkaline earth metal bicarbonates, alkali metal or alkaline earth metal carboxylates, and ammonium carbonate, or selected from the mixture of them. Preferably, the hydride of the alkali metal or alkaline earth metal is sodium hydride and/or potassium hydride. Preferably, the alkali metal or alkaline earth metal hydroxide is selected from one of sodium hydroxide, potassium hydroxide and lithium hydroxide, or selected from the mixture of them. Preferably, the alkali metal or alkaline earth metal alkoxide is selected from one of sodium methoxide, sodium ethoxide, potassium tert-butoxide, sodium tert-butoxide, sodium tert-terpoxide and potassium tert-terpoxide,or selected from the mixture of them. Preferably, the alkali metal or alkaline earth metal amide is sodium amide and/or lithium diisopropylamide. Preferably, the alkali metal or alkaline earth metal carbonate is selected from one of potassium carbonate, sodium carbonate, lithium carbonate and cesium carbonate, or selected from the mixture of them. Preferably, the alkali metal or alkaline earth metal bicarbonate is potassium bicarbonate and/or sodium bicarbonate. Preferably, the alkali metal or alkaline earth metal carboxylate is sodium acetate.

Preferably, the solvent for the substitution reaction is selected from one of an ether solvent, a halogenated alkane solvent and an aromatic hydrocarbon solvent, or selected from the mixture of them. Preferably, the ether solvent is tetrahydrofuran.

Preferably, in the substitution reaction, the molar ratio of the compound represented by Formula I to the solvent is 0.05 mol/L~0.5 mol/L, more preferably is 0.1 mol/L.

Preferably, in the substitution reaction, the molar ratio of the compound represented by Formula I to the compound represented by Formula IV is 1: 1.1~1: 3; more preferably, it is 1: 1.1~1: 1.3.

Preferably, the temperature of the substitution reaction is 0~35° C.; more preferably 0~25° C.

In the method for preparing the compound represented by the formula I', the progress of the substitution reaction can be monitored by a conventional test method (such as TLC, HPLC, GC, or NMR) in the art, generally when the compound as shown in Formula I disappearing, the reaction reaches the end point, the time of substitution reaction is preferably 1~12 hours.

In the method for preparing the compound represented by the formula I', after the substitution reaction is completed, the post-treatment operation can be further included. The methods and conditions of post-treatment can be conventional methods and conditions for such post-treatment in the art, and are preferably as following: concentration and column chromatography. The concentration is preferably vacuum distillation. The column chromatography is preferably a silica gel column. The column chromatography eluting agent is preferably a mixture of petroleum ether and aliphatic amine solvents having a volume ratio of 100:1~10:1 (for example, 20). Preferably, the fatty amine solvent is triethylamine.

In the present invention, room temperature refers to an ambient temperature of 20~30° C.

The term "alkyl" means a saturated linear or branched hydrocarbon moiety, such as -$CH_3$ or -$CH(CH_3)_2$. The term "alkoxy" refers to a generating group after the attachment of an alkyl group to an oxygen atom, such as -$OCH_3$, -$OCH_2CH_3$. The term "cycloalkyl" means a saturated cyclic hydrocarbon moiety, such as cyclohexyl. The term "aryl" means a hydrocarbyl moiety comprising one or more aromatic rings, including but not limited to phenyl, phenylene, naphthyl, naphthylene, anthracenyl, anthryl, phenanthryl.

Unless otherwise specified, alkyl, alkoxy, cycloalkyl, and aryl groups described herein include both substituted and unsubstituted moieties. Possible substituents on alkyl, alkoxy, cycloalkyl, and aryl groups include, but are not limited to: $C_1$-$C_6$ alkyl, $C_1$-$C_6$ haloalkyl, $C_2$-$C_6$ alkenyl, $C_2$-$C_6$ alkynyl, $C_3$-$C_{10}$ cycloalkyl, $C_3$-$C_{10}$ cycloalkenyl, $C_1$-$C_6$ alkoxy, aryl, hydroxy, halogen, amino.

On the basis of the common knowledge in the art, the above preferred conditions can be arbitrarily combined to obtain the preferred examples of the present invention.

Unless otherwise specified, reagents and starting materials used in the present invention are commercially available.

The positive and progressive effect of the present invention lies in:

1. The method for preparing the chiral fused-ring spirobiindane skeleton compound of the present invention does not require the use of chiral starting materials or chiral resolving agents, does not require chiral resolving steps, is simple in method, is simple in post-treatment, and is economic and environmental friendly, high product yield, high product optical purity and chemical purity.

2. The transition metal complex is prepared by using the chiral fused ring spirobiindane skeleton compounds of the present invention as the asymmetric hydrogenation catalyst. It has a significant catalytic effect, a product yield of >99%, and a product ee value of up to >99%.

3. The process for the preparation of compound II by the aldol condensation reaction of the present invention can achieve a yield of >90% and the post-treatment is more simple.

DESCRIPTION OF THE DRAWINGS

FIG. 1 is an X-ray crystal diffraction molecular structure diagram of the chiral fused ring spirobiindane skeleton compound I-g obtained in Example 20.

DETAILED DESCRIPTION

The present invention will be further illustrated by the following examples, but the present invention is not limited to the scope of the examples. The experimental methods that do not specify the specific conditions in the following examples are selected according to conventional methods and conditions, or according to the description of the product.

In the present invention, according to the common knowledge in the art, anti and syn are used to distinguish between cis and trans isomers, wherein anti refers to a trans configuration of a pair of cis and trans isomer compounds, and syn refers to a cis configuration of a pair of cis and trans isomers compounds.

In the present invention, according to the common knowledge in the art, the dr value represents the molar ratio between diastereomers. For example, if the diastereomer is a cis-trans isomer and the molar amount of the trans-configuration compound and the cis-configuration compound in the diastereoisomer is large, dr value=anti/syn*100%, That is, the value of dr is the molar ratio of the trans-configurational compound to the cis-configurational compound in the diastereoisomers, and vice versa.

In the present invention, according to the common knowledge in the art, the ee value represents an enantiomeric excess. For example, if a pair of enantiomers is independently the R and S configuration, and the molarity of the R configuration compound is larger than that of the S configuration, then ee value=(R−S)/(R+S)*100%, That is, the ratio of the difference in the molar amount of the two compounds to the sum of the molar amounts of the two compounds, and vice versa.

In the following examples, unless otherwise specified, the yield of the product or productivity refers to the isolation yield, that is, the yield obtained after the product is isolated and purified by the post-treatment, rather than the conversion rate before the post-treatment.

In the following examples, unless otherwise specified, $t_R$ (major) indicates the peak time of main product, $t_R$ (minor) indicates the peak time of byproduct, and the by-products are generally the diastereomeric configuration of cis trans configuration of the main product.

In the following examples, IR (neat) represents infrared detection of a pure product sample unless otherwise specified.

In the following examples, calcd. For represents the calculated value of the mass spectrum data of the compound, and Found represents the experimental value of the mass spectrum data unless otherwise specified.

In the following examples, Chiralcel OD-H column represents the Chiralcel OD-H chiral column of Japan Daicel Corporation unless otherwise stated.

EXAMPLE 1

As shown in the reaction scheme of the following formula, the preparation of the compound II-a is taken as an example. In this example, the general preparation method of the α,α'-bis(arylene) ketone compound (general formula II) according to the present invention is described in detail:

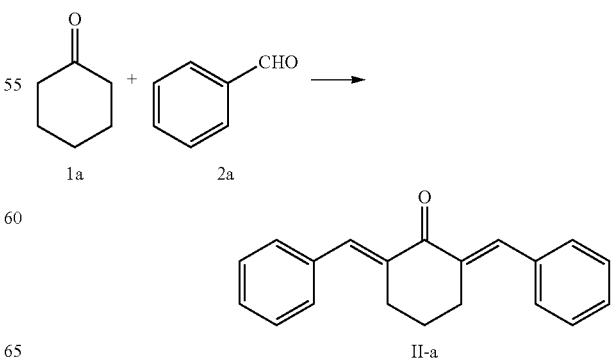

Sodium hydroxide (1.6 g, 40 mmol) and 1/1 (v/v) ethanol/water solution (100 mL) were added to a 250-mL egg plant-shaped vial, and were stirred to dissolve at room temperature. Then adding cyclohexanone (1.03 mL, 10 mmol) and benzaldehyde (2.2 mL, 22 mmol) in turn, and stirring at room temperature for 10 hours. A large amount of a yellow powder precipitated out from the reaction system and was suction-filtered, and the prepared solid was washed with a large amount of water (4 100 mL), and further washed with a small amount of ethanol (10 mL), and dried to give a yellow powdery solid product II-a (yield 85%).

II-a: M.P. 115-117° C., $^1$H NMR (400 MHz, CDCl$_3$) δ7.80 (s, 2 H), 7.47-7.32 (m, 10 H), 2.95-2.91 (m, 4 H), 1.82-1.75 (m, 2 H) ppm. $^{13}$C NMR (100 MHz, CDCl$_3$) δ190.4, 136.9, 136.1, 135.9, 130.3, 128.6, 128.4, 28.4, 23.0 ppm.

EXAMPLE 2

According to the preparation method of Example 1, only the substituents on the reaction substrate of the compound represented by Formula 2a were changed to prepare the α,α'-di(arylene) ketone compounds II-a~II-m shown as below:

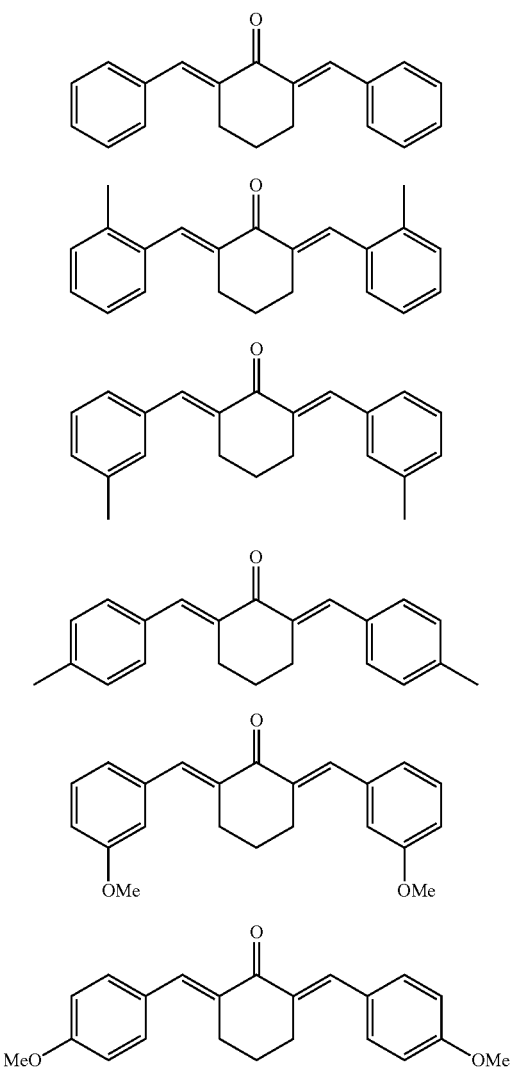

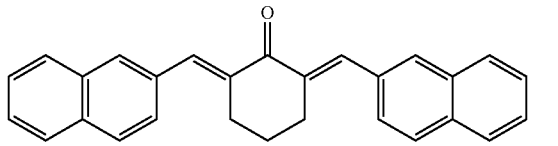

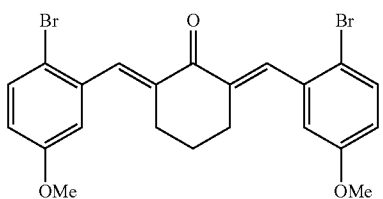

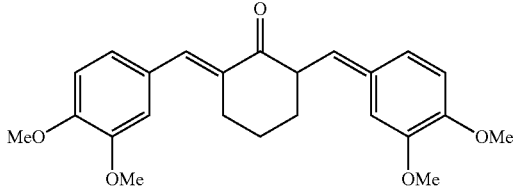

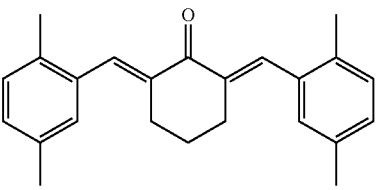

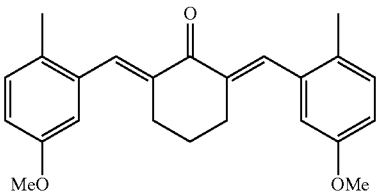

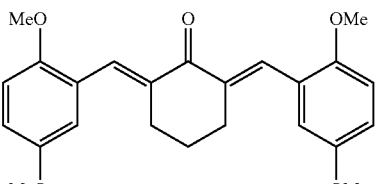

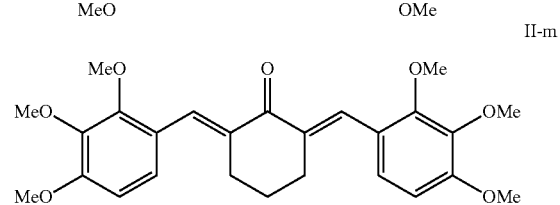

The Yield and Structure Identification Data of the Compound Shown in Formula II-b:

Yellow powder, 92%. M.P. 142-144° C., $^1$H NMR (400 MHz, CDCl$_3$) δ7.91 (s, 2 H), 7.26-7.18 (m, 8 H), 2.77-2.75 (m, 4 H), 2.34 (s, 6 H), 1.73-1.67 (m, 2 H), $^{13}$C NMR (100 MHz, CDCl$_3$) δ190.4, 137.9, 136.7, 136.0, 135.1, 130.1, 129.0, 128.4, 125.3, 28.4, 23.5, 20.0. IR (neat) v2932, 1664, 1590, 1463, 1400, 1277, 1240, 1195, 1165, 1138, 1018, 996, 968, 929, 860, 814, 783, 759, 736, 721, 607 cm$^{-1}$. HRMS (ESI) m/z: calcd. for C$_{22}$H$_{23}$O$^+$: 303.1743, Found: 303.1747 ([M+H]$^+$).

The Yield and Structure Identification Data of the Compound Shown in Formula II-c:

Yellow powder, yield 85%, M.P. 83-85° C., $^1$H NMR (400 MHz, CDCl$_3$) δ7.77 (s, 2 H), 7.31-7.24 (m, 6 H), 7.16-7.14 (m, 2 H), 2.94-2.91 (m, 4 H), 2.38 (s, 6 H), 1.80-1.74 (m, 2 H). $^{13}$C NMR (100 MHz, CDCl$_3$) δ109.3, 137.9, 137.0, 136.0, 135.9, 131.1, 129.4, 128.2, 127.4, 28.5, 23.0, 21.4. IR (neat) v 2939, 1659, 1597, 1490, 1428, 1276, 1227, 1180, 1162, 1143, 1072, 1050, 971, 946, 885, 835, 786, 758, 737, 717, 690, 616 cm$^{-1}$. HRMS (ESI) m/z: calcd. for C$_{22}$H$_{23}$O$^+$: 303.1743, Found: 303.1751 ([M+H]$^+$).

The Yield and Structure Identification Data of the Compound Shown in Formula II-d:

Yellow powder, yield 90%. M.P. 179-181° C., $^1$H NMR (400 MHz, CDCl$_3$) δ7.78 (s, 2 H), 7.38 (d, J=8.0 Hz, 4 H), 7.21 (d, J=8.4 Hz, 4 H), 2.92 (t, J=6 Hz, 4 H), 2.38 (s, 6 H), 1.81-1.75 (m, 2 H). $^{13}$C NMR (100 MHz, CDCl$_3$) δ190.4, 138.8, 136.8, 135.4, 133.1, 130.4, 129.1, 28.5, 23.0, 21.4. IR (neat) v 2938, 2915, 1660, 1598, 1564, 1507, 1311, 1266, 1197, 1154, 1139, 1016, 958, 935, 867, 817, 757, 729, 706, 660 cm$^{-1}$. HRMS (ESI) m/z: calcd. for C$_{22}$H$_{23}$O$^+$: 303.1743, Found: 303.1749 ([M+H]$^+$).

The Yield and Structure Identification Data of the Compound Shown in Formula II-e Yellow powder, yield 95%, $^1$H NMR (400 MHz, CDCl$_3$) δ7.76 (s, 2 H), 7.32 (t, J=8.0 Hz, 2 H), 7.06 (d, J=7.6 Hz, 2 H), 6.99 (s, 2 H), 6.89 (dd, J=8, 2.4 Hz, 2 H), 3.83 (s, 6 H), 2.94-2.91 (m, 4 H), 1.81-1.75 (m, 2 H). $^{13}$C NMR (100 MHz, CDCl$_3$) δ190.3, 159.4, 137.2, 136.8, 136.4, 129.3, 122.8, 115.7, 114.2, 55.2, 28.4, 22.9, IR (neat) v 2934, 2834, 1690, 1601, 1571, 1491, 1445, 1426, 1316, 1270, 1220, 1185, 1162, 1094, 1045, 993, 947, 921, 883, 868, 822, 769, 751, 674, 626 cm$^{-1}$. HRMS (ESI) m/z: calcd. for C$_{22}$H$_{23}$O$_3^+$: 335.1642, Found: 335.1646 ([M+H]$^+$).

The Yield and Structure Identification Data of the Compound Shown in Formula II-f:

Yellow powder, yield 90%, M.P. 167-169° C., 1H NMR (400 MHz, CDCl$_3$) δ7.76 (s, 2 H), 7.44 (d, J=8.8 Hz, 4 H), 6.92 (d, J=8.8 Hz, 4 H), 3.82 (s, 6 H), 2.89 (t, J=5.2 Hz, 4 H), 1.83-1.75 (m, 2 H). 13C NMR (100 MHz, CDCl$_3$) δ190.0, 159.8, 136.4, 134.2, 132.1, 128.6, 113.8, 55.2, 28.4, 22.9. IR (neat) v 2939, 2829, 1657, 1591, 1553, 1505, 1451, 1416, 1313, 1301, 1276, 1247, 1182, 1159, 1138, 1112, 1022, 965, 948, 868, 832, 809, 754, 731, 663 cm−1. HRMS (ESI) m/z: calcd. for C22 H23O3+: 335.1642, Found: 335.1647 ([M+H]+).

The Yield and Structure Identification Data of the Compound Shown in Formula II-g:

Yellow powder, yield 75%, M.P. 186-188° C.,$^1$H NMR (400 MHz, CDCl$_3$) δ7.98-7.95 (m, 4 H), δ7.88-7.83 (m, 6 H), δ7.60-7.58 (m, 2 H), δ7.52-7.50 (m, 4 H), $^{13}$C NMR (100 MHz, CDCl$_3$) δ190.3, 137.1, 136.4, 133.5, 133.1, 133.0, 130.2, 128.4, 127.9, 127.7, 127.6, 126.8, 126.4, 28.6, 23.0. IR (neat) v 3050, 2961, 2932, 2847, 2451, 1950, 1665, 1605, 1576, 1500, 1451, 1432, 1371, 1349, 1332, 1309, 1282, 1269, 1239, 1178, 1164, 1139, 1124, 1064, 1015, 987, 968, 946, 921, 893, 882, 860, 820, 773, 750, 728, 655, 640, 630, 611 cm$^{-1}$. HRMS-EI (m/z) M$^+$ calcd. for C$_{28}$H$_{22}$O$^+$ 374.1665 found 374.1673[M$^+$].

The Yield and Structure Identification Data of the Compound Shown in Formula II-h:

Yellow powder, yield 95%, M.P. 165-166° C., $^1$H NMR (400 MHz, CDCl$_3$) δ7.79 (s, 2 H), 7.50 (d, J=8.8 Hz, 2 H), 6.84 (d, J=2.8 Hz, 2 H), 6.75 (dd, J=8.4, 2.8 Hz, 2 H), 3.80 (s, 3H), 2.76 (t, J=5.6 Hz, 4 H), 1.79-1.72 (m, 2 H). $^{13}$C NMR (100 MHz, CDCl$_3$) δ189.3, 158.2, 137.4, 136.7, 136.2, 133.3, 116.3, 115.4, 115.1, 55.4, 28.2, 22.9. IR (neat) v 3071, 3000, 2961, 2941, 2872, 2847, 2829, 1656, 1590, 1566, 1462, 1438, 1398, 1299, 1280, 1263, 1238, 1193, 1165, 1145, 1111, 1041, 1017, 995, 858, 825, 813, 750, 733, 694, 606 cm$^{-1}$; EI-MS (70 eV), m/z=492 ([M]$^+$), 411, 331, 317, 301, 289, 274, 166, 128, 115, 102; calcd. for C$_{22}$H$_{20}$Br$_2$O$_3$: C, 53.68; H, 4.10%; Found: C, 53.67; H, 4.08%.

The Yield and Structure Identification Data of the Compound Shown in Formula II-i:

Yellow powder, yield 75%, M.P. 160-162° C.,$^1$H NMR (400 MHz, CDCl$_3$) δ7.76 (s, 2 H), 7.12-7.10 (m, 2 H), 7.02 (s, 2 H), 6.90 (d, J=8.4 Hz, 2 H), 3.91 (d, J=1 Hz, 12 H), 2.94 (t, J=5.2 Hz, 4 H), 1.85-1.81 (m, 2 H). $^{13}$C NMR (100 MHz, CDCl$_3$) δ189.9, 149.5, 148.5, 136.7, 134.4, 128.8, 123.8, 113.6, 110.7, 55.8, 55.8, 28.4, 22.9. IR (neat) v 2940, 2838, 1652, 1595, 1511, 1446, 1420, 1331, 1246, 1138, 1067, 1017, 991, 935, 920, 908, 865, 849, 806, 759, 719, 611 cm$^{-1}$. HRMS (ESI) m/z: calcd. for C$_{24}$H$_{27}$O$_5^+$: 395.1853, Found: 395.1860 ([M+H]$^+$).

The Yield and Structure Identification Data of the Compound Shown in Formula II-j:

Yellow powder, yield 90%, M.P. 142-144° C.,$^1$H NMR (400 MHz, CDCl$_3$) δ7.88 (s, 2 H), 7.13-7.04 (m, 6 H), 2.76 (m, 4 H), 2.33 (s, 6 H), 2.29 (s, 6 H), 1.72-1.70 (m, 2 H). $^{13}$C NMR (100 MHz, CDCl$_3$) δ190.4, 136.6, 136.1, 134.9, 134.8, 134.7, 130.0, 129.5, 129.1, 28.4, 23.5, 21.0, 19.6. IR (neat) v 2931, 1669, 1613, 1588, 1488, 1433, 1310, 1275, 1230, 1166, 1137, 1034, 928, 904, 810, 780, 751, 719 cm$^{-1}$. HRMS (ESI) m/z: calcd. for C$_{24}$H$_{27}$O$^+$: 331.2056, Found: 331.2063 ([M+H]$^+$).

The Yield and Structure Identification Data of the Compound Shown in Formula II-k:

Yellow powder, yield 85%, M.P. 75-77° C.,$^1$H NMR (400 MHz, CDCl$_3$) δ7.85 (s, 2 H), 7.12 (d, J=8.8, 2 H), 6.79-6.78 (m, 4 H), 3.78 (s, 6 H), 2.76 (t, J=4.8 Hz, 4 H), 2.25 (s, 6 H), 1.73-1.69 (m, 2 H). $^{13}$C NMR (100 MHz, CDCl$_3$) δ190.2, 157.1, 136.8, 136.0, 135.9, 130.9, 129.9, 114.7, 113.4, 55.3, 28.4, 23.4, 19.0. IR (neat) v 2919, 2834, 1663, 1605, 1582, 1491, 1466, 1444, 1411, 1282, 1250, 1235, 1211, 1159, 1138, 1116, 1038, 992, 950, 912, 884, 859, 819, 803, 749, 731, 706 cm$^{-1}$. HRMS (ESI) m/z: calcd. for C$_{24}$H$_{27}$O$_3^+$: 363.1955, Found: 363.1961 ([M+H]$^+$).

The Yield and Structure Identification Data of the Compound Shown in Formula II-l:

Yellow powder, yield 92%, M.P. 145-147° C. $^1$H NMR (400 MHz, CDCl$_3$) δ7.93 (s, 2 H), 6.88-6.85 (m, 6 H), 3.80 (s, 6 H), 3.79 (s, 6 H), 2.85 (t, J=5.2 Hz, 4 H), 1.77-1.74 (m, 2 H), $^{13}$C NMR (100 MHz, CDCl$_3$) δ190.4, 152.7, 136.8, 132.3, 125.8, 116.3, 114.3, 111.5, 56.0, 55.8, 28.7, 23.4. IR (neat) v 2945, 2832, 1663, 1600, 1491, 1462, 1414, 1280, 1249, 1218, 1180, 1155, 1141, 1036, 991, 934, 864, 809, 754, 732, 718, 698 cm$^{-1}$. HRMS (ESI) m/z: calcd. for C$_{24}$H$_{27}$O$_5^+$: 395.1853, Found: 395.1849([M+H]$^+$).

The Yield and Structure Identification Data of the Compound Shown in Formula II-m:

Yellow powder, yield 85%, M.P. 180-182° C., $^1$H NMR (400 MHz, CDCl$_3$) δ7.92 (s, 2 H), 7.08 (d, J=8.8 Hz, 2 H), 6.69 (d, J=8.4 Hz, 2 H), 3.90-3.89 (m, 18 H), 2.85-2.82 (m, 4 H), 1.77-1.75 (m, 2 H). $^{13}$C NMR (100 MHz, CDCl$_3$) δ190.1, 154.2, 153.4, 142.1, 135.7, 131.8, 125.1, 123.0, 106.5, 61.4, 60.8, 55.9, 28.8, 23.4. IR (neat) v 2938, 1660, 1587, 1490, 1456, 1410, 1264, 1204, 1160, 1137, 1090, 1041, 1017, 967, 943, 921, 879, 861, 820, 732, 698, 651 cm$^{-1}$.

EXAMPLE 3

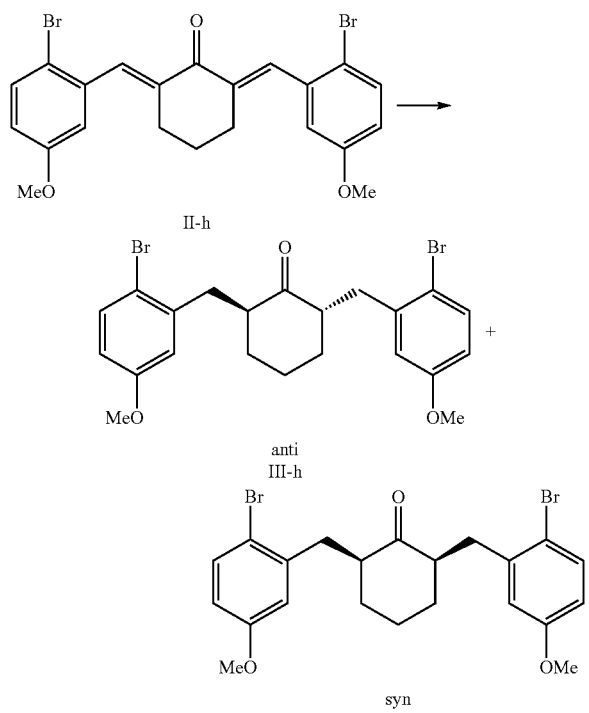

Under argon atmosphere, into an anhydrous anaerobic treatment of the Hydrogenated bottle (150-mL), were added compound II-h prepared in Example 2 (6.0 g, 12.2 mmol) and catalyst IrI/(S)-tBu-PHOX (0.061 mmol) and anhydrous dichloromethane (75 mL). The hydrogenated bottle was transferred to an autoclave in a glove box. After replacing hydrogen gas three times, hydrogen gas was charged to 30 atm and reacted at room temperature for 6~8 hours. Cautiously venting the residual hydrogen in a fume hood, opening the reaction vessel, and removing the solvent under reduced pressure, and sampling the mixture for 1 H NMR to determine the conversion of II-h >99% and the cis/reverse ratio of the product III-h (d.r.=anti/syn)>95: 5. The remaining mixture was decompressed to remove the solvent, and the residue was purified by silica gel column chromatography (petroleum ether/ethyl acetate 20:1) to give Colorless oily liquid III-h.

The compound III-h was obtained as a colorless oily liquid in 92% yield with an ee value of >99%. $[\alpha]_D^{20}$=−18.79 (c 1.0, $CHCl_3$). The ee value of the product was determined by chiral high performance liquid chromatography, the chiral column was a Chiralcel AS-H chiral column from Japan Daicel Corporation; (mobile phase, isopropanol/n-hexane (v/v)=5:95, temperature was room temperature; flow rate: 0.5 mL/min; UV-V is detection, detection wavelength λ=230 nm); Compound III-h retention time $t_R$ (major)= 17.49 min; the retention time of Cis configurational isomers, of compound III-h $t_R$ (minor)=19.31 min.

The Structure Identification Data of compound III-h: $^1$H NMR (400 MHz, $CDCl_3$) δ7.38 (d, J=8.4 Hz, 2 H), 6.72 (d, J=3.2 Hz, 2 H), 6.61 (dd, J=8.8, 2.8 Hz, 2 H), 3.73 (s, 3 H), 3.18 (dd, J=13.6, 3.0 Hz, 2 H), 2.97-2.90 (m, 2 H), 2.72 (dd, J=14.0, 8.4 Hz, 2 H), 1.96-1.88 (m, 2 H), 1.83-1.77 (m, 2 H), 1.70-1.62 (m, 2 H), $^{13}$C NMR (100 MHz, $CDCl_3$) δ213.7, 158.6, 139.9, 133.2, 116.9, 114.9, 113.5, 55.3, 48.9, 36.4, 32.2, 20.6, IR (pure sample) v 2992, 2959, 2920, 2854, 2834, 1571, 1466, 1457, 1437, 1315, 1286, 1271, 1256, 1174, 1102, 1079, 1035, 967, 800, 607 $cm^{-1}$; EI-MS (70 eV), m/z: 496 ([M]$^+$), 415, 336, 215, 199, 187, 137, 121, 91, 77; HRMS-EI (m/z): calculated value $C_{22}H_{24}O_3Br_2^+$: 494.0092, measured value: 494.0096 ([M]$^+$).

EXAMPLE 4

Under argon atmosphere, into an anhydrous anaerobic treatment of the Hydrogenated bottle(150-ml) were added the compound II-h prepared in Example 2 (0.1 g, 0.2 mmol), catalyst A (0.002 mmol), and Anhydrous dichloromethane. (5 mL). In the glove box, transfer the hydrogenated bottle to the autoclave, replace the hydrogen three times, and then fill it with hydrogen and react at room teinperature for 12 hours. The residual hydrogen was vented carefully in a fume hood, the reaction vessel was opened and the solvent was removed under reduced pressure. The mixture was sampled for the conversion of II-h and the ratio of product III-h (d.r.=anti/syn) as determined by $^1$H NMR. The remaining mixture was removed under reduced pressure to remove the solvent, and the residue was purified by silica gel column chromatography (petroleum ether/ethyl acetate 20:1) to give a colorless oily liquid III-h. The product ee value and the value of dr were determined as Chiral HPLC method in Example 3. The catalyst type and hydrogen pressure, product yield, dr value and ee value were as shown in Table 1.

TABLE 1

| Catalyst A | Hydrogen pressure (atm) | yield (%) | anti/syn[c] | ee (%) |
| --- | --- | --- | --- | --- |
| Ir$^I$/(S)-$^t$Bu-PHOX | 50 | 93 | >19:1 | 99 |
| Ir$^I$/(R,S)-Bn-SpinPHOX | 50 | 90 | 19:1 | 99 |
| Ir$^I$/(S,S)-Bn-SpinPHOX | 50 | 85 | >19:1 | 99 |
| Ir$^I$/(S)-$^t$Bu-PHOX | 30 | 93 | >19:1 | 99 |

The structure of each compound of catalyst A in Table 1 is as shown below:

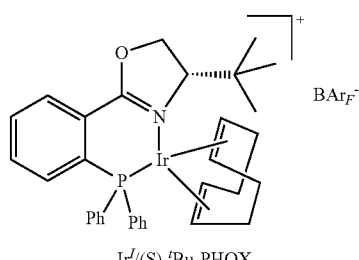

Ir$^I$/(S)-$^t$Bu-PHOX

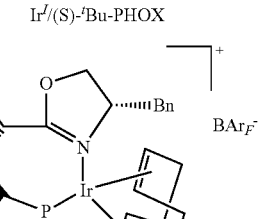

Ir$^I$/(R,S)-Bn-SpinPHOX

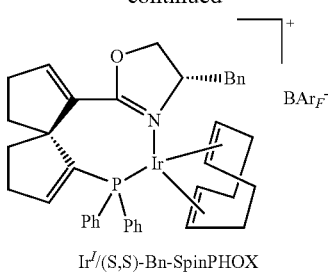

Ir[I]/(S,S)-Bn-SpinPHOX

It can be seen from Table 1 that the use of the above-mentioned several different chiral iridium (I)/phosphine-oxazoline complexes as catalysts have similar catalytic effects and all have excellent dr values (ant/syn≥19:1).) and 99% eeto obtain the corresponding asymmetric hydrogenation product III-h. The product yield was slightly different, with Ir I/(S)-t Bu-PHOX having the best overall effect. In a reaction condition of reacting at room temperature for 12 hours at 30 atm hydrogen pressure with a dr value of>19:1, 99% ee and 93% isolated yield giving III-h.

EXAMPLE 5

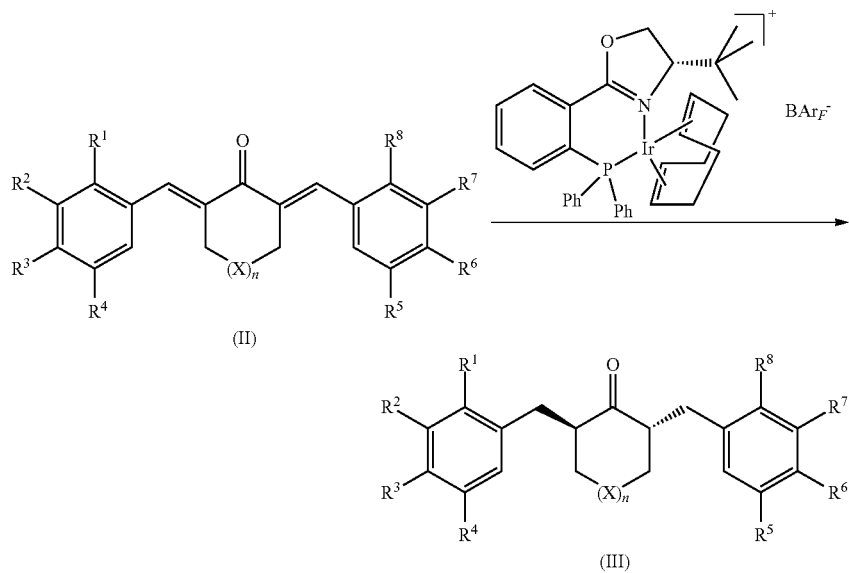

As shown in the above formula, the compounds II-a to II-m prepared from Example 2 were used as hydrogenation substrates, respectively, with 1.0% phosphine-oxazoline ligand ruthenium complex IrI/(S)-tBu-PHOX as a catalyst (percentage is catalyst molar ratio of compound II molar amount), according to the experimental method described in Example 3, only the hydrogenation substrate is changed, the hydrogen pressure is changed to 30 atm, the reaction time becomes 8 hours, the reaction was carried out to obtain hydrogenated products III-a to III-m shown below. The dr values of these products were all measured as anti/syn>19:1.

The relevant yields and structural analysis characterization data of the hydrogenated products I II-a to III-m are shown as below:

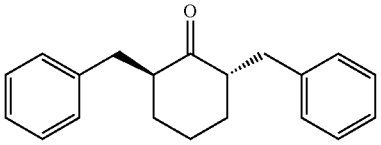

III-a

White powder, yield 90%. >99% ee, $[\alpha]_D^{20}=-56.5$ (c 1.00, CHCl$_3$). The ee of the product was determined by chiral high performance liquid chromatography, Chiralcel AS-H column; mobile phase, isopropanol/hexane (v/v)=2:98, temperature, room temperature; mobile phase flow rate, 0.5 mL/min; UV-V is detection, wavelength λ=220 nm; $t_R$ (major)=13.22 min; $t_R$ (minor)=20.22 min. $^1$H NMR (400 MHz, CDCl$_3$) δ7.28-7.11 (m, 10 H), 3.10 (dd, J=13.6, 5.6 Hz, 2 H), 2.80-2.75 (m, 2 H), 2.60 (dd, J=13.6, 9.2 Hz, 2 H), 1.90-1.84 (m, 2 H), 1.77-1.71 (m, 2 H), 1.63-1.57 (m, 2 H) ppm. $^{13}$C NMR (100 MHz, CDCl$_3$) δ214.7, 139.6, 129.0, 128.4, 126.2, 50.7, 36.2, 31.8, 20.3 ppm.

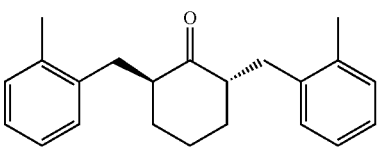

III-b

Colorless liquid, yield 94%. >99% ee, $[\alpha]_D^{20}=-38.0$ (c 0.97, CHCl$_3$). The ee of the product was determined by chiral high performance liquid chromatography, Chiralcel AS-H column; mobile phase, isopropanol/n-hexane (v/v)=5:95, temperature, room temperature; mobile phase flow rate, 0.5 mL/min; UV-V is detection, wavelength λ=220 nm; $t_R$ (major)=9.52 min; $t_R$ (minor)=11.27 min. The absolute configuration was assigned by analogy. $^1$H NMR (400 MHz, CDCl$_3$) δ7.08-6.99 (m, 8 H), 3.08 (dd, J=14.0, 5.2 Hz, 2 H), 2.73-2.71 (m, 2 H), 2.56 (dd, J=13.6, 9.2 Hz, 2 H), 2.26 (s, 6 H), 1.87-1.82 (m, 2 H), 1.71-1.68 (m, 2 H), 1.59-1.55 (m, 2 H). $^{13}$C NMR (100 MHz, CDCl$_3$) δ 214.0, 137.5, 135.8, 130.1, 129.5, 126.1, 125.5, 49.0, 33.1, 31.6, 20.3, 19.2. IR (neat) v 3016, 2929, 2860, 2349, 2323, 1703, 1604, 1492, 1454, 1379, 1270, 1143, 1120, 1031, 941, 919, 898, 867, 833, 741, 671, 665 cm$^{-1}$. HRMS (ESI) m/z: calcd. for C$_{22}$H$_{30}$NO$^+$: 324.2322, Found: 324.2321 ([M+NH$_4$]$^+$).

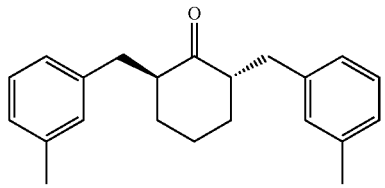

III-c

Colorless liquid, yield 82%. >99% ee, [α]$_D^{20}$=−56.3 (c 1.02, CHCl$_3$). The ee of the product was determined by chiral high performance liquid chromatography, Chiralcel AS-H column; mobile phase, isopropanol/n-hexane (v/v)=5: 95, temperature, room temperature; mobile phase flow rate, 0.5 mL/min; UV-V is detection, wavelength λ=220 nm; t$_R$(major)=9. 20 min; t$_R$(minor)=12.30 min. $^1$H NMR (400 MHz, CDCl$_3$) δ7.15-7.11 (m, 2 H), 6.99-6.89 (m, 6 H), 3.05 (dd, J=14.0, 6.0 Hz, 2 H), 2.75-2.72 (m, 2 H), 2.54 (dd, J=13.2, 8.8 Hz, 2 H), 2.29 (s, 6 H), 1.87-1.82 (m, 2 H), 1.70-1.67 (m,2 H), 1.57-1.54 (m, 2 H). $^{13}$C NMR (100 MHz, CDCl$_3$) δ214.5, 139.4, 137.7, 129.6, 128.1, 126.7, 125.8, 50.5, 35.9, 31.6, 21.2, 20.1. IR (neat) v 2925, 2859, 1705, 1608, 1488, 1446, 1377, 1117, 1037, 921, 852, 782, 766, 743, 699 cm$^{-1}$. HRMS-EI (m/z) calcd. for C$_{22}$H$_{26}$O$^+$ 306.1978 found 306.1988 [M$^+$].

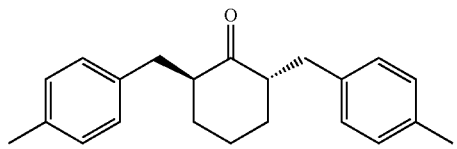

III-d

White powder, yield 90%. >99% ee, M.P. 71-73° C., [α]$_D^{20}$=−46.2 (c 1.10, CHCl$_3$). The ee of the product was determined by chiral high performance liquid chromatography, Chiralcel AS-H column; mobile phase, isopropanol/ hexane (v/v)=5:95, temperature, room temperature; mobile phase flow rate, 0.5 mL/min; UV-V is detection, wavelength λ=220 nm; t$_R$ (major)=9.45 min; t$_R$ (minor)=11.26 min. $^1$H NMR (400 MHz, CDCl$_3$) δ7.08 (d, J=8.0 Hz, 4 H), 7.01 (d, J=7.6 Hz, 4 H), 3.05 (dd, J=13.6, 5.6 Hz 2 H), 2.76-2.72 (m, 2 H), 2.56 (dd, J=13.6, 9.2 Hz, 2 H), 2.32 (s, 6 H), 1.90-1.85 (m, 2 H), 1.74-1.71 (m, 2 H), 1.60-1.55 (m, 2 H). $^{13}$C NMR (100 MHz, CDCl$_3$) δ215.0, 136.5, 135.6, 129.1, 128.9, 50.8, 35.7, 31.8, 21.0, 20.3. IR (neat) v 3007, 2928, 2854, 1902, 1695, 1516, 1441, 1344, 1320, 1286, 1258, 1231, 1150, 1091, 1022, 943, 921, 904, 868, 798, 772, 752, 708, 644, 613 cm$^{-1}$. HRMS (ESI) m/z: calcd. for C$_{22}$H$_{30}$NO$^+$: 324.2322, Found: 324.2319 ([M+NH$_4$]$^+$).

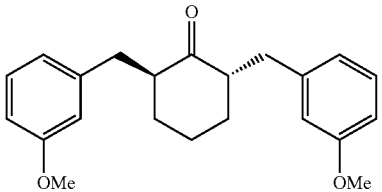

III-e

Colorless liquid, yield 97%. >99% ee, [α]$_D^{20}$=−48.2 (c 1.01, CHCl$_3$). The ee of the product was determined by chiral high performance liquid chromatography, Chiralcel AS-H column; mobile phase, isopropanol/n-hexane (v/v)= 10:90, temperature, room temperature; mobile phase flow rate, 0.5 mL/min; UV-V is detection, wavelength λ=220 nm; t$_R$ (major)=14.19 min; t$_R$ (minor)=19.48 min. $^1$H NMR (400 MHz, CDCl$_3$) δ7.16 (t, J=7.6 Hz, 2 H), 6.74-6.69 (m, 6 H), 3.75 (s, 6 H), 3.06 (dd, J=13.6, 5.2 Hz, 2 H), 2.76-2.73 (m, 2 H), 2.56 (dd, J=13.6, 9.2 Hz, 2 H), 1.88-1.84 (m, 2 H), 1.72-1.69 (m, 2 H), 1.61-1.54 (m, 2 H). $^{13}$C NMR (100 MHz, CDCl$_3$) δ214.4, 159.4, 141.0, 129.2, 121.2, 114.6, 111.2, 54.9, 50.4, 36.0, 31.6, 20.1. IR (neat) v 2930, 1703, 1583, 1488, 1453, 1257, 1152, 1118, 1041, 853, 780, 747 cm$^{-1}$. HRMS-EI (m/z) M$^+$ calcd. for C$_{22}$H$_{26}$O$_3^+$338.1876 found 338.1876.

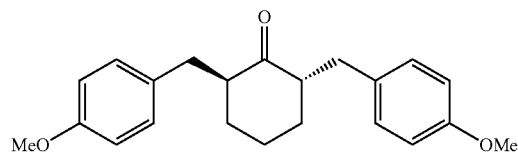

III-f

White powder, yield 95%. >99% ee, M.P. 68-70° C. [α]$_D^{20}$=−30.6 (c 1.03, CHCl$_3$). The ee of the product was determined by chiral high performance liquid chromatography, Chiralcel AS-H column; mobile phase, isopropanol/ hexane (v/v)=10:90, temperature, room temperature; mobile phase flow rate, 0.5 mL/min; UV-V is detection, wavelength λ=230 nm; t$_R$ (major)=16.16 min; t$_R$ (minor)=20.49 min. $^1$H NMR (400 MHz, CDCl$_3$) δ7.03 (d, J=8.4 Hz, 4 H), 6.80 (d, J=8.4 Hz, 4 H), 3.74 (s, 6 H), 3.04 (dd, J=14, 6.4 Hz, 2 H), 2.75-2.72 (m, 2 H), 2.55 (dd, J=13.6, 8.4 Hz, 2 H), 1.89-1.83 (m, 2 H), 1.73-1.70 (m, 2 H), 1.60-1.55 (m, 2 H). $^{13}$C NMR (100 MHz, CDCl$_3$) δ214.3, 157.6, 131.2, 129.5, 113.4, 54.7, 50.6, 35.0, 31.6, 20.0. IR (neat) v 2936, 2860, 2838, 1888, 1692, 1610, 1583, 1509, 1457, 1440, 1420, 1359, 1342, 1321, 1300, 1279, 1243, 1231, 1174, 1136, 1114, 1099, 1074, 1028, 959, 916, 893, 871, 846, 831, 810, 776, 759, 736, 708, 683, 623 cm$^{-1}$. HRMS (ESI) m/z: calcd. for C$_{22}$H$_{30}$NO$_3^+$: 335.2220, Found: 335.2216 ([M+NH$_4$]$^+$).

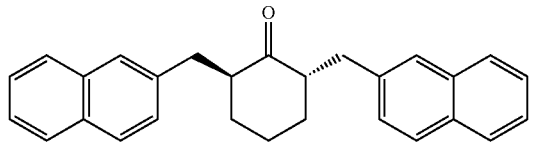

III-g

White powder, yield 95%. >99% ee, M.P. 108-110° C. $[\alpha]_D^{20}=-0.1$ (c 1.2, CHCl$_3$). The ee of the product was determined by chiral high performance liquid chromatography, Chiralcel AS-H column; mobile phase, isopropanol/hexane (v/v)=10:90, temperature, room temperature; mobile phase flow rate, 0.5 mL/min; UV-V is detection, wavelength λ=220 nm; $t_R$ (major)=12.98 min; $t_R$ (minor)=15.58 min. $^1$H NMR (400 MHz, CDCl$_3$) δ7.73-7.71 (m, 2 H), 7.65 (d, J=8.4 Hz, 4 H), 7.49 (s, 2 H), 7.39-7.34 (m, 4 H), 7.19 (dd, J=8.0, 1.2 Hz, 2 H), 3.21 (dd, J=14.0, 6.0 Hz, 2 H), 2.86-2.82 (m, 2 H), 2.69 (dd, J=13.6, 8.8 Hz, 2 H), 1.83-1.78 (m, 2 H), 1.63-1.60 (m, 2 H), 1.55-1.50 (m, 2 H). $^{13}$C NMR (100 MHz, CDCl$_3$) δ214.3, 137.0, 133.3, 131.9, 127.9, 127.4, 127.3, 127.3, 127.2, 125.8, 125.2, 50.5, 36.2, 31.8, 20.1. IR (neat) v 3055, 2922, 2858, 2349, 2323, 1948, 1703, 1632, 1600, 1505, 1470, 1448, 1358, 1312, 1274, 1247, 1211, 1157, 1123, 1107, 1083, 1067, 1015, 989, 974, 949, 921, 900, 876, 861, 826, 817, 773, 742, 687, 671, 665, 650, 622, 610 cm$^{-1}$. HRMS (ESI) m/z: calcd. for C$_{28}$H$_{30}$NO$^+$: 396.2322, Found: 396.2320 ([M+H]$^+$).

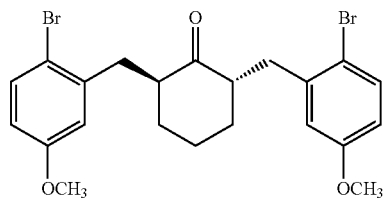

III-h

Colorless oily liquid, yield 92%. >99% ee, $[\alpha]_D^{20}=-18.79$ (c 1.0, CHCl$_3$). The ee of the product was determined by chiral high performance liquid chromatography, Chiralcel AS-H column; mobile phase, isopropanol/n-hexane (v/v)=5:95, temperature, room temperature; mobile phase flow rate, 0.5 mL/min; UV-V is detection, wavelength λ=230 nm; $t_R$ (major)=17.49 min; $t_R$ (minor)=19.31 min. $^1$H NMR (400 MHz, CDCl$_3$) δ7.38 (d, J=8.4 Hz, 2 H), 6.72 (d, J=3.2 Hz, 2 H), 6.61 (dd, J=8.8, 2.8 Hz, 2 H), 3.73 (s, 6 H), 3.18 (dd, J=13.6, 6.0 Hz, 2 H), 2.97-2.90 (m, 2 H), 2.72 (dd, J=14.0, 8.4 Hz, 2 H), 1.96-1.88 (m, 2 H), 1.83-1.77 (m, 2 H), 1.70-1.62 (m, 2 H) ppm; $^{13}$C NMR (100 MHz, CDCl$_3$) δ213.7, 158.6, 139.9, 133.2, 116.9, 114.9, 113.5, 55.3, 48.9, 36.4, 32.2, 20.6 ppm; EI-MS (70 eV), m/z: 496 ([M]$^+$), 415, 336, 215, 199, 187, 137, 121, 91, 77; HRMS-EI (m/z): calcd. for C$_{22}$H$_{24}$O$_3$Br$_2^+$: 494.0087, found: 494.0096 ([M]$^+$).

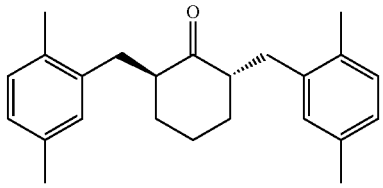

III-i

White powder, yield 95%. >99% ee, M.P. 102-104° C., $[\alpha]_D^{20}=-44.1$ (c 1.10, CHCl$_3$), >99% ee. The ee of the product was determined by chiral high performance liquid chromatography, Chiralcel AS-H column; mobile phase, isopropanol/hexane (v/v)=10:90, temperature, room temperature; mobile phase flow rate, 0.5 mL/min; UV-Vis detection, wavelength λ=220 nm; $t_R$ (major)=26.73 min; $t_R$ (minor)=34.04 min. $^1$H NMR (400 MHz, CDCl$_3$) δ6.58-6.45 (m, 6 H), 3.65 (s, 12 H), 2.88 (dd, J=13.6, 6.4 Hz, 2 H), 2.61-2.58 (m, 2 H), 2.39 (dd, J=13.6, 8.4 Hz, 2 H), 1.75-1.70 (m, 2 H), 1.60-1.57 (m, 2 H), 1.46-1.41 (m, 2 H). $^{13}$C NMR (100 MHz, CDCl$_3$) δ214.0, 148.1, 146.7, 131.4, 120.2, 111.5, 110.4, 55.0, 55.0, 50.2, 35.2, 31.4, 19.7. IR (neat) v 2996, 2920, 2847, 2349, 1604, 1495, 1463, 1451, 1406, 1330, 1295, 1278, 1260, 1242, 1207, 1184, 1116, 1077, 1063, 1024, 996, 943, 880, 853, 786, 768, 732, 701, 671, 665, 609 cm$^{-1}$. HRMS-EI (m/z) M$^+$ calcd. for C$_{24}$H$_{30}$O$_5^+$ 398.2088 found 398.2099[M$^+$].

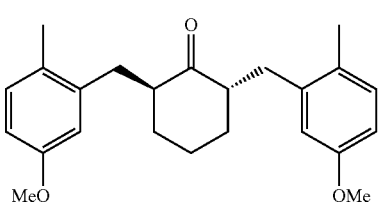

III-j

White powder, yield 95%. >99% ee, M.P. 103-105° C., $[\alpha]_D^{20}=-30.5$ (c 1.10, CHCl$_3$). The ee of the product was determined by chiral high performance liquid chromatography, Chiralcel AS-H column; mobile phase, isopropanol/hexane (v/v)=5:95, temperature, room temperature; mobile phase flow rate, 0.5 mL/min; UV-Vis detection, wavelength λ=220 nm; $t_R$ (major)=8.03 min; $t_R$ (minor)=8.94 min. $^1$H NMR (400 MHz, CDCl$_3$) δ7.20-7.06 (m, 6 H), 3.26 (dd, J=14, 4.8 Hz, 2 H), 2.93-2.91 (m, 2 H), 2.74 (dd, J=14, 9.6 Hz 2 H), 2.45 (s, 6 H), 2.43 (s, 6 H), 2.09-2.05 (m, 2 H), 1.93-1.90 (m, 2 H), 1.83-1.76 (m, 2 H). $^{13}$C NMR (100 MHz, CDCl$_3$) δ214.2, 137.5, 134.8, 132.7, 130.3, 130.1, 126.8, 49.2, 33.2, 31.6, 20.7, 20.4, 18.8. IR (neat) v 3002, 2929, 2852, 2349, 1894, 1698, 1615, 1503, 1455, 1370, 1339, 1297, 1261, 1244, 1235, 1178, 1157, 1143, 1121, 1094, 1075, 1051, 1032, 949, 921, 895, 855, 810, 709, 671, 664, 615 cm$^{-1}$. HRMS (ESI) m/z: calcd. for C$_{24}$H$_{34}$NO$^+$: 352.2635 Found: 352.2634([M+NH$_4$]$^+$).

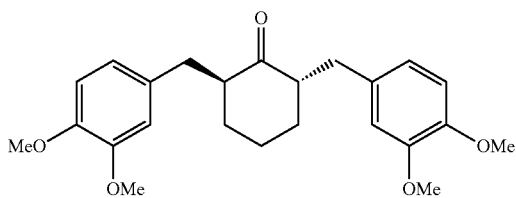

III-k yellow powder, yield 90%. M.P. 88-90° C., $[\alpha]_D^{20}=-41.9$ (c 1.10, CHCl$_3$), 99% ee. The ee of the product was determined by chiral high performance liquid chromatography, Chiralcel AS-H column; mobile phase, isopropanol/hexane (v/v)=10:90, temperature, room temperature; mobile phase flow rate, 0.5 mL/min; UV-V is detection, wavelength λ=220 nm; $t_R$ (major)=12.17 min; $t_R$ (minor)=13.82 min. $^1$H NMR (400 MHz, CDCl$_3$) δ7.04 (d, J=8.0 Hz, 2 H), 6.67-6.64 (m, 2 H), 3.74 (s, 6 H), 3.06 (dd, J=13.6, 4.4 Hz, 2 H), 2.76-2.73 (m, 2 H), 2.57 (dd, J=13.6, 9.6 Hz, 2 H), 2.22 (s, 6 H), 1.91-1.87 (m, 2 H), 1.76-1.73 (m, 2 H), 1.64-1.59 (m, 2 H). $^{13}$C NMR (100 MHz, CDCl$_3$) δ214.5, 157.5, 138.9, 131.0, 128.0, 115.6, 111.0, 55.0, 49.1, 33.5, 31.6, 20.4, 18.5. IR (neat) v 2998, 2957, 2925, 2849, 2834, 2349, 2323, 2073, 1694, 1607, 1580, 1499, 1442, 1382, 1361, 1338, 1307, 1289, 1273, 1249, 1215, 1204, 1160, 1121, 1096, 1056, 1030, 996, 973, 930, 895, 870, 853, 833, 816, 802, 757, 725, 715, 691, 671, 665, 652, 613 cm$^{-1}$. HRMS-EI (m/z) calcd. for $C_{24}H_{30}O_3{}^+$ 366.2189 found 366.2197.

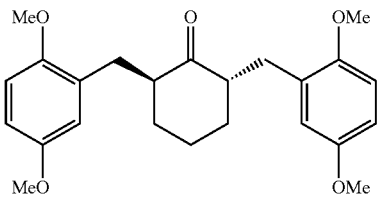
III-l

Colorless oily liquid, yield 89%. $[\alpha]_D^{20}=-15.9$ (c 1.15, CHCl$_3$), >99% ee. The ee of the product was determined by chiral high performance liquid chromatography, Chiralcel AS-H column; mobile phase, isopropanol/n-hexane (v/v)= 10:90, temperature, room temperature; mobile phase flow rate, 0.5 mL/min; UV-V is detection, wavelength λ=230 nm; $t_R$ (major)=20.94 min; $t_R$ (minor)=23.53 min. $^1$H NMR (400 MHz, CDCl$_3$) δ6.76-6.69 (m, 6 H), 3.75 (s, 6 H), 3.72 (s, 6 H), 3.11 (dd, J=13.2, 5.6 Hz, 2 H), 2.90-2.88 (m, 2 H), 2.62 (dd, J=13.2, 9.2 Hz, 2 H), 1.87-1.83 (m, 2 H), 2.73 (m, 2 H), 1.60-1.57 (m, 2 H). $^{13}$C NMR (100 MHz, CDCl$_3$) δ214.8, 152.9, 151.5, 129.0, 116.8, 110.8, 110.7, 55.3, 55.1, 48.8, 32.3, 30.9, 20.2. IR (neat) v 2931, 2833, 1702, 1590, 1497, 1463, 1426, 1282, 1219, 1179, 1158, 1127, 1045, 1024, 934, 854, 800, 733, 712 cm$^{-1}$. HRMS (ESI) m/z: calcd. for $C_{24}H_{34}NO_5{}^+$: 416.2429, Found: 416.2431 ([M+NH$_4$]$^+$).

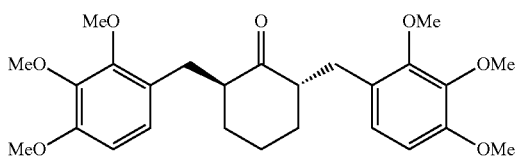
III-m

Colorless oily liquid, yield, >99% ee. $[\alpha]_D^{20}=-8.7$ (c 1.00, CHCl3). The ee of the product was determined by chiral high performance liquid chromatography, Chiralcel AS-H column; mobile phase, isopropanol/n-hexane (v/v)= 10:90, temperature, room temperature; mobile phase flow rate, 0.5 mL/min; UV-V is detection, wavelength λ=220 nm; $t_R$ (major)=15.51 min; $t_R$ (minor)=16.71 min. $^1$H NMR (400 MHz, CDCl$_3$) δ6.64 (d, J=8.4 Hz, 2 H), 6.45 (d, J=8.4 Hz, 2 H), 3.77 (s, 6 H), 3.74 (s, 6 H), 3.70 (s, 6 H), 2.91 (dd, J=13.6, 6.4 Hz, 2 H), 2.73-2.70 (m, 2 H), 2.47 (dd, J=13.2, 8 Hz, 2 H), 1.78-1.74 (m, 2 H), 1.66-1.63 (m, 2 H), 1.50-1.46 (m, 2 H). $^{13}$C NMR (100 MHz, CDCl$_3$) δ214.6, 151.7, 151.5, 141.6, 125.0, 124.1, 106.5, 60.2, 60.1, 55.3, 49.4, 32.1, 30.0, 20.1. IR (neat) v 2932, 2854, 1703, 1601, 1493, 1464, 1416, 1274, 1257, 1233, 1199, 1163, 1094, 1039, 1015, 950, 904, 854, 795, 752, 682, 665 cm$^{-1}$.

EXAMPLE 6

In an argon atmosphere, compound III-h (ee, >99%, 247 mg, 0.5 mmol) and anhydrous dichloromethane (10 mL) were added to a 50-mL Schlenk tube. The temperature was cooled to 0° C. in an ice bath, slowly adding the catalyst (TiCl$_4$ as the catalyst in this example) (0.11 mL, 1.0 mmol), the reaction mixture was stirred at 0° C. for 30 minutes, then slowly warm to room temperature, continue stirring for 5 hours. After the reaction was monitored by TLC, 5 mL of water was added to quench the reaction. The mixture of the reaction was extracted three times with dichloromethane (5 mL×3). The organic phases were combined and dried over anhydrous sodium sulfate. The desiccant was removed by filtration and the filtrate was evaporated under reduced pressure. The residue was purified by silica gel column chromatography (petroleum ether/Ethyl acetate=50:1) to give a white powder(1S, 2S, 2'S)-I-h. The ee value of the product was determined by chiral HPLC [Chiralcel OD-H column; mobile phase, isopropanol/n-hexane=0:100, Temperature, room temperature. Mobile phase flow rate, 0.8 mL/min; UV-V is detection wavelength λ=230 nm; $t_R$ (major)=15.80 min; $t_R$ (minor)=23.00 min.].

EXAMPLE 7

Comparative Example 1

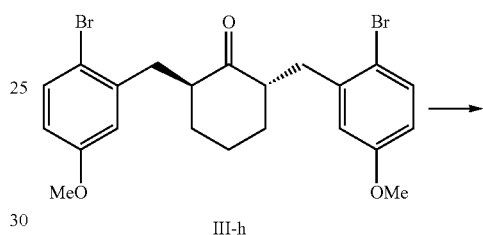
III-h

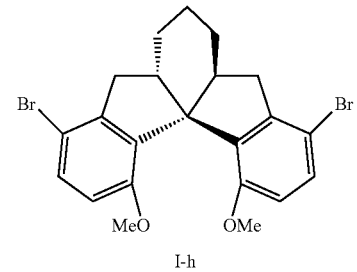
I-h

According to the method of Example 6, the amount of the substrate compound III-h (0.2 mmol in the present example), the type and amount of the catalyst, the kind and the amount of the solvent (The dosage of the solvent was 2.0 mL in the present example) were used only in accordance with the conditions shown in Table 2. And the reaction temperature was changed. The yield and ee values are shown in Table 2. The molar equivalents in Table 2 represent the multiples of the molar amount of the catalyst relative to the molar amount of Compound III-h. In Solvents column of Table 2, "—" indicates no solvent. In ee value of Table 2, "—" indicates that cannot be measured.

In this example, the reaction time is 12h

TABLE 2

| Catalyst No | (molar equivalent) | Solvent | Reaction Temperature (° C.) | Yield (%) | ee (%) |
|---|---|---|---|---|---|
| 1 | Polyphosphate (30) | — | 80 | 72 | |
| 2 | Methane sulfonic acid (30) | — | 40 | 70 | |
| 3 | Phosphotungstic acid H$_3$[W$_{12}$PO$_{40}$] (0.1) | methylbenzene | 110 | 25 | |

TABLE 2-continued

| Catalyst No | (molar equivalent) | Solvent | Reaction Temperature (° C.) | Yield (%) | ee (%) |
|---|---|---|---|---|---|
| 4 | Chiral Phosphoric Acid (0.2) | methylbenzene | 80 | 0 | |
| 5 | Chiral Phosphoric Acid and 4 Å Molecular Sieves (0.5) | methylbenzene | 25-80 | 0 | |

From the data in Table 2, it can be seen that when polyphosphoric acid (PPA) or methane sulfonic acid is used, the reaction proceeds smoothly under heating conditions, and the ring-closing products are obtained in yields of 72% and 70%, but unfortunately the product is not optically active (see the ee values data in two rows numbered 1 and 2 in Table 2), most likely due to the racemization of compound III-h in these protonic acid environments. When the phosphotungstic acid $H_3[W_{12}PO_{40}]$ was refluxed in toluene, the reaction yield was low, only 25%, and a completely racemic ring-closing product I-h was also obtained. When catalyzed by chiral phosphoric acid (CPA) or chiral phosphoric acid and 4A molecular sieves (CPA/4A MS), no corresponding ring product was obtained.

The catalysts in this example are all Bronsted type of common protonic acids, and it can be seen that Bronsted type protonic acid is not suitable as a catalyst for compound III-h stereoselective ring closing.

In the present invention, the structure of chiral phosphoric acid (CPA) is represented by the following formula:

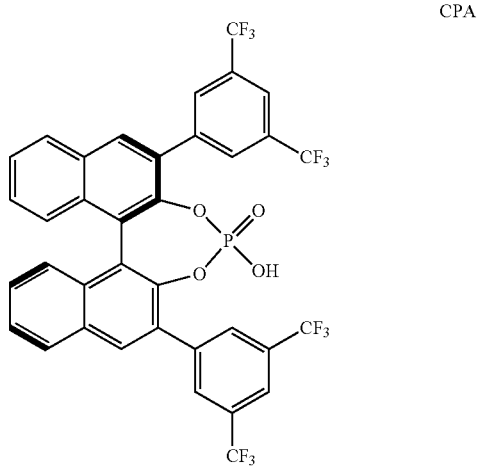

CPA

EXAMPLE 8

Comparative Example 2

According to the method of Example 6, the amount of the substrate compound III-h (0.2 mmol in the present example), the type and amount of the catalyst, the kind and the amount of the solvent (The dosage of the solvent was 2.0 mL in the present example) were used only in accordance with the conditions shown in Table 3. And the reaction temperature was changed. The yield and ee values are shown in Table 3. The molar equivalents in Table 3 represent the multiples of the molar amount of the catalyst relative to the molar amount of Compound III-h. In ee value of Table 2, "–" indicates that cannot be measured.

In this example, the reaction time is 12 h.

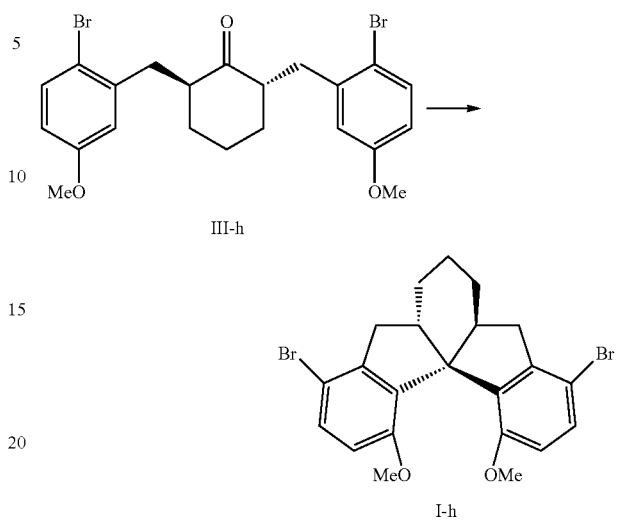

TABLE 3

| No | Catalyst (molar equivalent) | solvent | reaction temperature (° C.) | yield (%) | ee (%) |
|---|---|---|---|---|---|
| 1 | Sc(OTf)$_3$ (2) | CH$_2$Cl$_2$ | 40 | 0 | — |
| 2 | In(OTf)$_3$ (2) | CH$_2$Cl$_2$ | 40 | 0 | — |
| 3 | Cu(OTf)$_2$ (2) | CH$_2$Cl$_2$ | 40 | 0 | — |
| 4 | AlCl$_3$ (2) | CH$_2$Cl$_2$ | 40 | 0 | — |
| 5 | SnCl$_4$ (2) | CH$_2$Cl$_2$ | 40 | 0 | — |
| 6 | FeCl$_3$ (2) | CH$_2$Cl$_2$ | 40 | 0 | — |
| 7 | Ti($^i$PrO)$_4$ (2) | CH$_2$Cl$_2$ | 40 | 0 | — |
| 8 | Cp$_2$TiCl$_2$ (2) | CH$_2$Cl$_2$ | 40 | 0 | — |
| 9 | TiCl$_4$/(±)BINOL (2) | CH$_2$Cl$_2$ | 40 | 0 | — |
| 10 | Ti($^i$PrO)$_4$ (0.1) | methylbenzene | 80 | little | — |
| 11 | Sc(OTf)$_3$ (0.2) | methylbenzene | 80 | 0 | — |
| 12 | Ti($^i$PrO)$_4$ (1) | methylbenzene | 80 | 0 | — |
| 13 | SnCl$_4$/(±)BINOL (1.2/0.2) | CH$_2$Cl$_2$ | 25 | 0 | — |
| 14 | Cp$_2$TiCl$_2$ (1) | methylbenzene | 80 | 0 | — |
| 15 | AlCl$_3$ (1.5) | DCE | 80 | 0 | — |
| 16 | Cu(OTf)$_2$ (0.5) | DCE | 80 | 0 | — |

EXAMPLE 9

According to the method of Example 6, the amount of the substrate compound III-h (0.2 mmol in the present example), the type and amount of the catalyst, the kind and the amount of the solvent (The dosage of the solvent was 2.0 mL in the present example) were used only in accordance with the conditions shown in Table 4. And the reaction temperature was changed. The yield and ee values are shown in Table 4. The molar equivalents in Table 4 represent the multiples of the molar amount of the catalyst relative to the molar amount of Compound III-h.

In this example, the reaction time is 12 h.

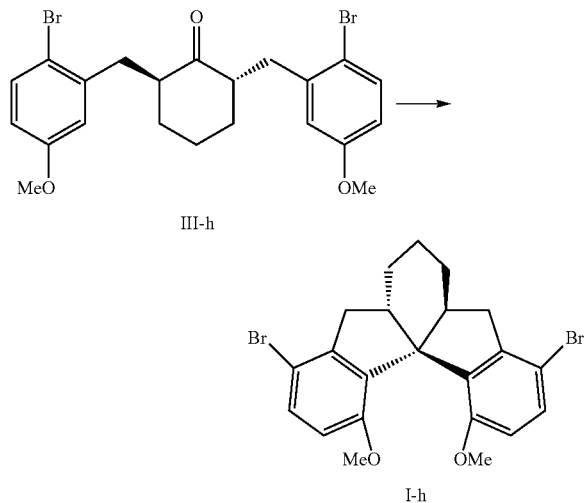

III-h

I-h

TABLE 4

| No | Catalyst (molar equivalent) | solvent | reaction temperature (° C.) | yield (%) | ee (%) |
|---|---|---|---|---|---|
| 1 | TiCl4 (2) | CH2Cl2 | 40 | 51 | 99 |

As can be seen from Table 3 and Table 4, a series of Lewis acid (Lewis acid) metal salts in Table 3 has no promoting effect on the ring-closing reactions, and no corresponding products were obtained. However, under the action of the strong Lewis acid TiCl4 in Table 4, the reaction proceeds smoothly, and (1S, 2S, 2'S)-I-h is obtained with a yield of 51%, and the optical purity of the raw materials is basically maintained. The ee value of (1S, 2S, 2'S)-I-h reaches 99%.

EXAMPLE 10

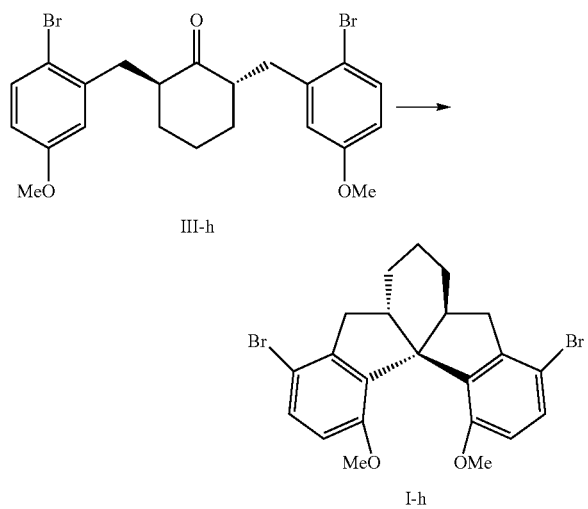

III-h

I-h

According to the method of Example 6, only change the amount of the substrate compound III-h (0.2 mmol in the present example), the type and amount of the catalyst(the catalyst is TiCl4 and the dosage of catalyst is 0.4 mmol in the present example.), the kind and the amount of the solvent (The solvent is dichloromethane, and the dosage is 2.0 mL. In the present example),and change the temperature and the time of the reaction were only in accordance with the conditions shown in Table 4. The yield and ee values are shown in Table 4.

In this example, the reaction time is 12 h.

TABLE 5

| No | reaction temperature (° C.) | response time (h) | yield (%) | ee (%) |
|---|---|---|---|---|
| 1 | 40 | 2 | 52 | 99 |
| 2 | 25 | 2 | 55 | 99 |
| 3 | 10 | 8 | 72 | >99 |

As can be seen from Table 5, for the III-h asymmetric dehydration cyclization catalyzed by TiCl4 in methylene chloride, the product yield is medium and the product ee value is 99% after reacting 2 hours when the temperature is between 25° C. and 40° C. When the reaction was conducted at 10° C. for 8 hours, the yield of the product was increased to 72%, and the ee of the product slightly increased to >99%. After continuously reducing the temperature to 5° C., the product yield remained essentially unchanged after 12 hours of reaction, and the product ee value was also maintained. Further lowering the temperature to 0° C., the reaction system was cleaner, but the activity was reduced, and the reaction time was extended to 20 hours. The yield was only 62%. When the reaction slowly recovers from the 0° C. in initial to room temperature, the side reactions are also effectively suppressed and the ring-closing product I-h is obtained in 84% yield and >99% ee.

EXAMPLE 11

The experimental procedure was carried out in the same manner as in Example 6, only changes were made of the amount of the substrate compound of formula III-h (in this example is 0.2mmol). The type and amount of catalysts (in this example the catalyst is TiCl4, the amount is 0.4 mmol), the amount of solvent (in this example the amount is 2.0 mL), and making changes of the type of solvent, reaction temperature and reaction time according to the conditions shown in Table 6. The yield and EE value are shown in Table 6.

TABLE 6

| No | Solvent | Reactino time (h) | yield (%) | ee (%) |
|---|---|---|---|---|
| 1 | CH2Cl2 | 6 | 84 | >99 |
| 2 | DCE | 10 | 52 | >99 |
| 3 | CHCl3 | 8 | 65 | >99 |
| 4 | Toluene | 12 | 56 | >99 |

It can be concluded from table 6 that different solvents have great influence on yield of the Cyclization reaction. When 1,2-dichloroethane (DEC) and CHCl3 used as solvent, the reaction products yield reduced to 52% and 65% respectively, but the enantio selectivity was still kept and more than 99% ee. When toluene used as solvent, the reaction was reacted relatively slow, the reaction system is more complex, and the product yield was dropped to 56%, but the enantio selectivity is stillmore than 99% ee of the target product. Therefore, methylene chloride is the most optimal reaction solvent.

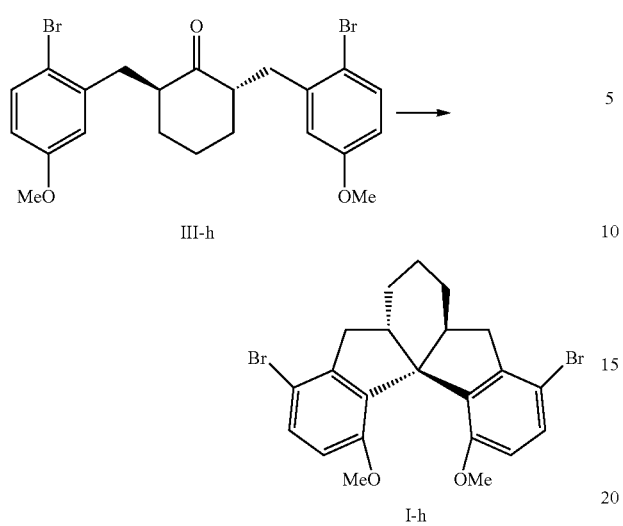

III-h

I-h

The experimental procedure was carried out in the same manner as in Example 6, only changes were made of the amount of the substrate compound of formula III-h (in this example is 0.2 mmol). The type and amount of catalysts (in this example the catalyst is $TiCl_4$), the type of solvent (in this example the solvent is $CH_2Cl_2$), making changes of the amount of catalyst, substrate concentration (the molar volume ratio (mol/L) of substrate compound of formula III-h and solvent), reaction time according to the conditions shown in Table 7. In Table 7, the molar equivalent indicates the molar ratio of the catalyst to the molar ratio of the substrate compound of formula III-h.

TABLE 7

| No. | $TiCl_4$ (Molar equivalents) | Substrate concentration (mol/L) | Reaction time (h) | Yield (%) | ee (%) |
| --- | --- | --- | --- | --- | --- |
| 1 | 2 | 0.2 | 4 | 75 | >99 |
| 2 | 2 | 0.1 | 6 | 84 | >99 |
| 3 | 2 | 0.05 | 6 | 93 | >99 |
| 4 | 2 | 0.02 | 6 | 91 | >99 |
| 5 | 4 | 0.05 | 4 | 72 | >99 |
| 6 | 1 | 0.05 | 6 | 81 | >99 |

It can be concluded from table 7 that: under the temperature condition from 0° C. warm back slowly to room temperature, the substrate concentration and the amount change of $TiCl_4$ have certain influence on reactivity, while less effected on the optical purity of the product (>99% ee). When the substrate concentration was increased to 0.2 M, the side effects increased, the reaction yield was decreased to 75%. When reducing the substrate concentration to 0.05 M, side effects were suppressed, with the product I-h yield of up to 93%. This shows that the lower concentration of the reactant is beneficial to the intramolecular N-cyclohexylmaleimide reactions. Continuely reducing the substrate concentration to 0.02 M, the reaction ratio was slowed. The amount of $TiCl_4$ also affect the yield of the product. When the amount of $TiCl_4$ increased from 2 eq. to 4 eq, the yield significantly reduced. When the amount of $TiCl_4$ reduced to 1 eq., the substrate was not completely conversed, the yield was reduced to 81%.

EXAMPLE 13

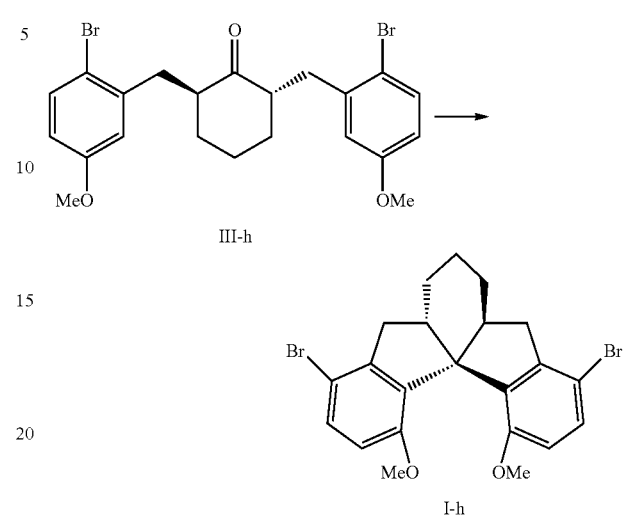

III-h

I-h

Under the argon atmosphere, into an anhydrous anaerobic treatment Schlenk tube (50 mL), were added compound III-h (>99% ee) (247 mg, 0.5 mmol) and anhydrous methylene chloride (10 mL), the temperature was cooled to 0° C., slowly add $TiCl_4$ (0.11 mL, 1.0 mmol), the reaction mixture was reacted for 30 minutes below 0° C., then warm back slowly to room temperature, continuely stirred for 5 hours, adding 5 mL water to quench the reaction, the reaction mixture was extracted with dichloromethane for three times (5 mL×3), the anqueous layer was combined and dried over $Na_2SO_4$, and was filter to remove desiccant. After the filtrate was decompressed and removed the solvent, the residue was separated and purified by silica gel column chromatography (petroleum ether/ethyl acetate=50:1).The white solid I-h was obtained (220 mg, 93%), and the ee value of the product was determined by HPLC.

EXAMPLE 14

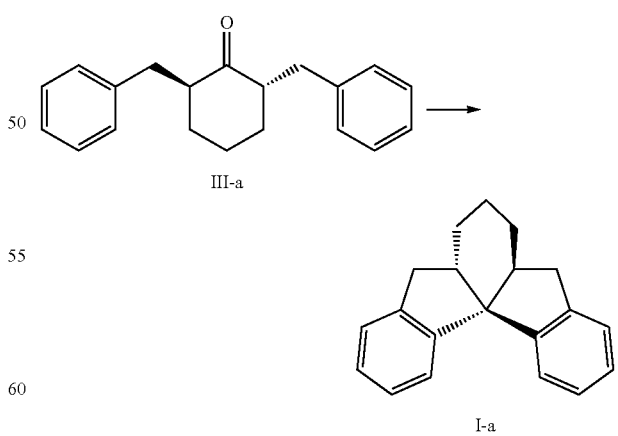

III-a

I-a

Taking the compound III-a (>99% ee) obtained in Example 5 as substrate, referring to the experimental methods disclosed in Example 13, the compound of III-a was reacted through intramolecular asymmetric cyclization under the presence of 2 molar equivalent TiCl$_4$ (the molar equivalent relative to the comound III-a) to afford the chiral spirobiindane skeleton compound I-a.

The data of character and structure of product compound I-a: colorless liquid, yield 83%, 96% ee, $[\alpha]_D^{20}$=131.1 (c 1.10, CHCl$_3$) and the ee value of the product was determined by chiral HPLC. Chiralcel OD-H column; eluent, 2-propanol/hexane 5:95; temp, r.t.; flow rate, 0.5 mL/min; uv-vis detection, λ=210 nm; $t_R$ (minor)=8.52 min; $t_R$ (major)=9.97 min. $^1$H NMR (400 MHz, CDCl$_3$) δ7.31-7.06 (m, 6 H), δ6.76 (d, J=7.6 Hz, 2 H), δ3.10 (dd, J=15.6, 7.2 Hz, 2 H), δ2.75 (dd, J=15.2, 5.6 Hz, 2 H), δ2.62-2.55 (m 2 H), δ1.61-1.49 (m, 4 H), δ1.43-1.37 (m, 2 H) ppm. $^{13}$C NMR (100 MHz, CDCl$_3$) δ149.0, 142.8, 126.5, 126.3, 124.9, 123.1, 61.0, 43.6, 36.1, 27.4, 19.6 ppm. IR (neat) v 3065, 3017, 2922, 2847, 2661, 2310, 1944, 1905, 1600, 1474, 1456, 1260, 1025, 934, 880, 800, 747, 727, 706, 661, 635 cm$^{-1}$. HRMS-EI (m/z) calcd. for C$_{20}$H$_{20}$$^+$260.1560, found 260.1568 [M$^+$].

EXAMPLE 15

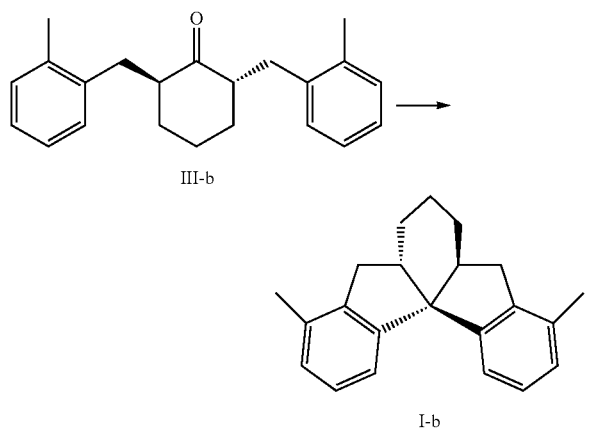

Taking the compound III-b (>99% ee) obtained in Example 5 as substrate, referring to the experimental methods disclosed in Example 13, the compound of III-b was reacted through intramolecular asymmetric cyclization under the presence of 2 molar equivalent TiCl$_4$ to afford the chiral spirobiindane skeleton compound I-b.

The data of character and structure of product compound I-b: white solid, yield 85%, >99% ee, M.P. 151-153° C., $[\alpha]_D^{20}$=225.0 (c 1.10, CHCl$_3$), and the ee value of the product was determined by chiral HPLC. Chiralcel PA-2 column; eluent, acetonitrile/water 80:20; temp, r.t.; flow rate, 0.7 mL/min; uv-vis detection, λ=230 nm; $t_R$ (major)= 9.54 min; $t_R$ (minor)=10.21 min. $^1$H NMR (400 MHz, CDCl$_3$) δ7.01-6.98 (m, 4 H), δ6.59-6.57 (m, 2 H), δ3.01 (dd, J=15.6, 7.2 Hz, 2 H), δ2.65 (dd, J=15.6, 5.6 Hz, 2 H), δ2.57-2.54 (m 2 H), δ2.31 (s, 6 H), δ1.60-1.50 (m, 4 H), δ1.43-1.36 (m, 2 H). $^{13}$C NMR (100 MHz, CDCl$_3$) δ148.9, 141.4, 134.1, 127.4, 126.5, 120.4, 61.3, 43.3, 34.7, 27.6, 19.7, 19.1. IR (neat) v 3016, 2921,2852, 2834, 1918, 1856, 1795, 1595, 1459, 1446, 1377, 1319, 1261, 1210, 1196, 1158, 1141, 1094, 1076, 1032, 953, 930, 896, 871, 790, 779, 756, 727, 711, 668, 645, 619 cm$^{-1}$. HRMS-EI (m/z) calcd. for C$_{22}$H$_{24}$$^+$288.1873, found 288.1874 [M$^+$].

EXAMPLE 16

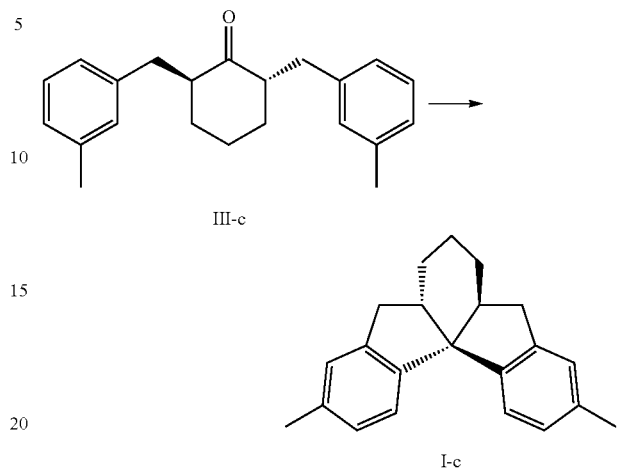

Taking the compound III-c (>99% ee) obtained in Example 5 as substrate, referring to the experimental methods disclosed in Example 13, the compound of III-c was reacted through intramolecular asymmetric cyclization under the presence of 2 molar equivalent TiCl$_4$ to afford the chiral spirobiindane skeleton compound I-c.

The product property and structure identification data: colorless liquid, yield 75%, 96% ee, $[\alpha]_D^{20}$=168.5 (c 1.10, CHCl$_3$). And the ee value of the product was determined by chiral HPLC. Chiralcel PA-2 column; eluent, acetonitrile/water 80:20; temp, r.t.; flow rate, 0.7 mL/min; uv-vis detection, λ=230 nm; $t_R$ (major)=10.21 min; $t_R$ (minor)=12.39 min. $^1$H NMR (400 MHz, CDCl$_3$) δ7.11 (s, 2 H), 6.89 (d, J=8.0 Hz, 2 H), 6.65 (d, J=8.0 Hz, 2 H), 3.04 (dd, J=15.2, 6.8 Hz, 2 H), 2.69 (dd, J=15.2, 6 Hz, 2 H), 2.55-2.52 (m, 2 H), 2.32 (s, 6 H), 1.57-1.48 (m, 4 H), 1.39-1.36 (m,2 H). $^{13}$C NMR (100 MHz, CDCl$_3$) δ146.3, 142.8, 136.0, 127.1, 125.7, 122.8, 60.3, 43.9, 36.1, 27.5, 21.3, 19.7. IR (neat) v 3004, 2920, 2847, 1614, 1485, 1447, 1377, 1357, 1299, 1260, 1217, 1191, 1136, 1082, 1037, 956, 930, 879, 810, 799, 756, 708, 680, 668, 626 cm$^{-1}$.

EXAMPLE 17

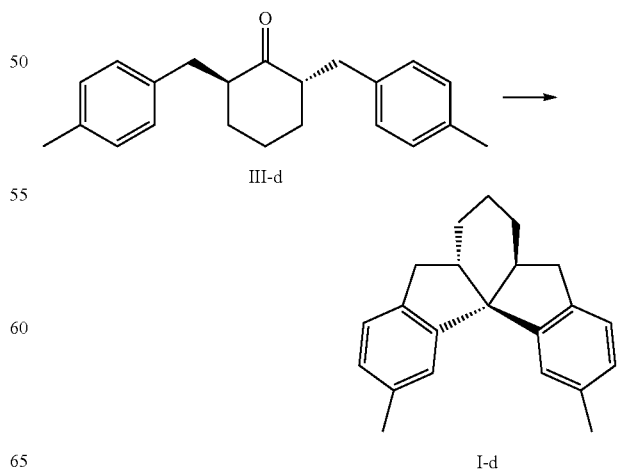

Taking the compound III-d (>99% ee) obtained in Example 5 as substrate, referring to the experimental methods disclosed in Example 13, the compound of III-d was reacted through intramolecular asymmetric cyclization under the presence of 2 molar equivalent TiCl$_4$ to afford the chiral spirobiindane skeleton compound I-d.

The product property and structure identification data: white solid, yield 70%, 93% ee, M.P. 102-104 ° C., $[\alpha]_D^{20}$=31.3 (c 1.10, CHCl$_3$). And the ee value of the product was determined by chiral HPLC. Chiralcel PC-3 column; eluent, acetonitrile/water 60:40; temp, r.t.; flow rate, 0.5 mL/min; uv-vis detection, $\lambda$=230 nm; t$_R$ (minor) =27.33 min; t$_R$ (major)=29.00 min. $^1$H NMR (400 MHz, CDCl$_3$) δ7.19 (d, J=7.6 Hz, 2 H), 6.98 (d, J=7.6 Hz, 2 H), 6.57 (s, 2 H), 3.05 (dd, J=15.6, 7.2 Hz, 2 H), 2.69 (dd, J=19.2, 9.2 Hz, 2 H), 2.57-2.54 (m, 2 H), 2.23 (s, 6 H), 1.59-1.47 (m, 4 H), 1.41-1.35 (m, 2 H). $^{13}$C NMR (100 MHz, CDCl$_3$) δ149.2, 139.7, 135.8, 127.3, 124.6, 123.8, 60.8, 43.9, 35.8, 27.5, 21.4, 19.7. IR (neat) v 3003, 2919, 2848, 2350, 1892, 1756, 1612, 1488, 1447, 1377, 1312, 1260, 1207, 1137, 1080, 1022, 948, 930, 879, 847, 810, 796, 727, 706, 632 cm$^{-1}$. HRMS-EI (m/z) M$^+$ calcd. for C$_{22}$H$_{24}^+$ 288.1873 found 288.1873 [M$^+$].

EXAMPLE 18

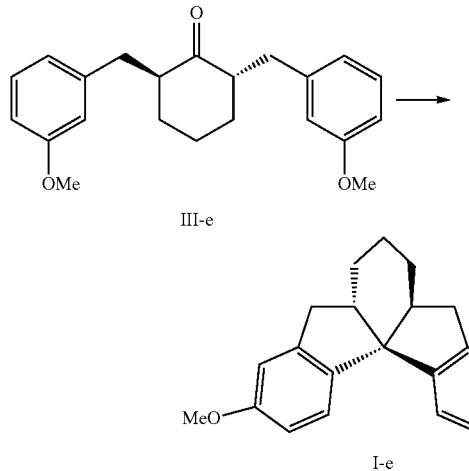

Taking the compound III-e (>99% ee) obtained in Example 5 as substrate, referring to the experimental methods in Example 13, the compound of III-e was reacted through intramolecular asymmetric cyclization reaction under the presence of 2 molar equivalent TiCl$_4$ to afford the chiral spirobiindane skeleton compound I-e.

The product property and structure identification data: white solid, yield 65%, 97% ee, M.P. 94-96° C., $[\alpha]_D^{20}$=138.1 (c 1.10, CHCl$_3$). And the ee value of the product was determined by chiral HPLC. Chiralcel OD-H column; eluent, 2-propanol/hexane 2:98; temp, r.t.; flow rate, 0.5 mL/min; uv-vis detection, $\lambda$=220 nm; t$_R$ (minor)= 10.52 min; t$_R$ (major)=11.62 min. $^1$H NMR (400 MHz, CDCl$_3$) δ6.85 (s, 2 H), 6.67-6.60 (m, 4 H), 3.76 (s, 6 H), 3.04 (dd, J=15.6, 7.2 Hz, 2 H), 2.69 (dd, J=15.6, 6.0 Hz, 2 H), 2.55-2.51 (m, 2 H), 1.58-1.46 (m, 4 H), 1.40-1.34 (m, 2 H). $^{13}$C NMR (100 MHz, CDCl$_3$) δ158.7, 144.0, 141.5, 123.5, 111.8, 110.4, 59.4, 55.2, 44.1, 36.2. 27.4, 19.6.IR (neat) v 2919, 2845, 1605, 1584, 1484, 1463, 1308, 1246, 1219, 1193, 1142, 1116, 1033, 913, 839, 799, 750. HRMS-EI (m/z) M$^+$ calcd. for C$_{22}$H$_{24}$O$_2^+$320.1771 found 320.1780[M$^{+1}$

EXAMPLE 19

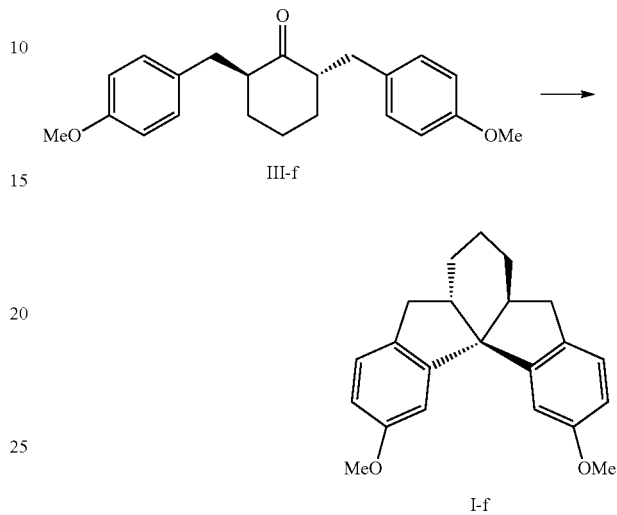

Taking the compound III-f (>99% ee) obtained in Example 5 as substrate, referring to the experimental methods in Example 13, the compound of III-f was reacted through intramolecular asymmetric cyclization reaction under the presence of 2 molar equivalent TiCl$_4$ to afford the chiral spirobiindane skeleton compound I-f.

The product property and structure identification data: white solid, yield 60%,79.9% ee, M.P. 146° C., $[\alpha]_D^{20}$=67.3 (c 1.10, CHCl$_3$). And the ee value of the product was determined by chiral HPLC. Chiralcel OD-H column; eluent, 2-propanol/hexane 2:98; temp, r.t.; flow rate, 0.5 mL/min; uv-vis detection, $\lambda$=220nm; t$_R$ (minor)=10.05 min; t$_R$ (major)=16.65 min. $^1$H NMR (400 MHz, CDCl$_3$) δ7.24 (d, J=8.0 Hz, 2 H), 6.76 (dd, J=8.0, 2.4 Hz, 2 H), 6.39 (d, J=2.8 Hz, 2 H), 3.73 (s, 6 H), 3.07 (dd, J=14.8, 6.8 Hz, 2 H), 2.72 (dd, J=15.2, 6 Hz, 2 H), 2.62-2.59 (m, 2 H), 1.64-1.54 (m, 4 H), 1.46-1.43 (m, 2 H).$^{13}$C NMR (100 MHz, CDCl$_3$) δ158.7, 150.3, 134.6, 125.4, 111.9, 109.0, 61.4, 55.2, 44.1, 35.3, 27.5, 19.6. IR (neat) v 2995, 2927, 2852, 1605, 1584, 1482, 1462, 1327, 1283, 1273, 1240, 1228, 1215, 1199, 1151, 1141, 1121, 1086, 1061, 1032, 930, 866, 845, 823, 808, 768, 755, 704, 672 cm$^{-1}$. HRMS (ESI) m/z: calcd. for C$_{22}$H$_{25}$O$_2^+$: 321.1849, Found: 321.1851 ([M+H]$^+$).

EXAMPLE 20

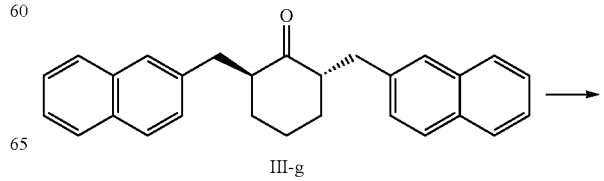

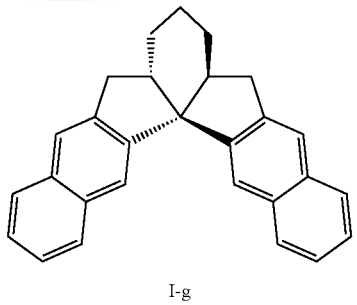

I-g

Taking the compound III-g (>99% ee) obtained in Example 5 as substrate, referring to the experimental methods disclosed in Example 13. The compound of III-g was reacted through intramolecular asymmetric cyclization reaction under the presence of 2 molar equivalent TiCl$_4$ to obtain the chiral spirobiindane skeleton compound I-g.

The product property and structure identification data: colorless solid, yield 57%, M.P. 248-250° C., $[\alpha]_D^{20}$=−151.0 (c 1.10, CHCl$_3$), 99% ee. $^1$H NMR (400 MHz, CDCl$_3$) δ7.82-7.79 (m, 4 H), 7.61 (d, J=8.0 Hz, 2 H), 7.41-7.33 (m, 3 H), 7.31 (s, 1 H), 7.19 (s, 2 H), 3.33 (dd, J=16, 7.2 Hz, 2 H), 2.97 (dd, J=15.6, 6.4 Hz, 2 H), 2.78-2.75 (m, 2 H), 1.68-1.56 (m, 4 H), 1.46-1.42 (m, 2 H). $^{13}$C NMR (100 MHz, CDCl$_3$) δ148.5, 142.1, 133.2, 133.0, 127.8, 127.3, 125.1, 124.9, 123.1, 121.5, 60.4, 43.8, 35.6, 27.3, 19.6. HPLC [(column, Chiralcel PC-2; eluent, acetonitrile/water 60:40; temp, r.t.; flow rate, 0.7 mL/min; detection, 230 nm light); $t_R$ (R)=125.33 min; $t_R$ (S)=131.56 min]. IR (neat) v 3050, 2952, 2925, 2902, 2847, 2349, 2323, 1951, 1701, 1634, 1604, 1498, 1447, 1432, 1336, 1289, 1261, 1208, 1143, 1096, 1037, 1018, 951, 930, 886, 868, 801, 750, 671, 665, 623, 614. HRMS-EI (m/z) M$^+$ calcd. for C$_{28}$H$_{28}^+$ 360.1873 found 360.1880[M$^+$].

The PXRD spectrum of chiral spirobiindane skeleton compound I-g as shown in FIG. 1.

EXAMPLE 21

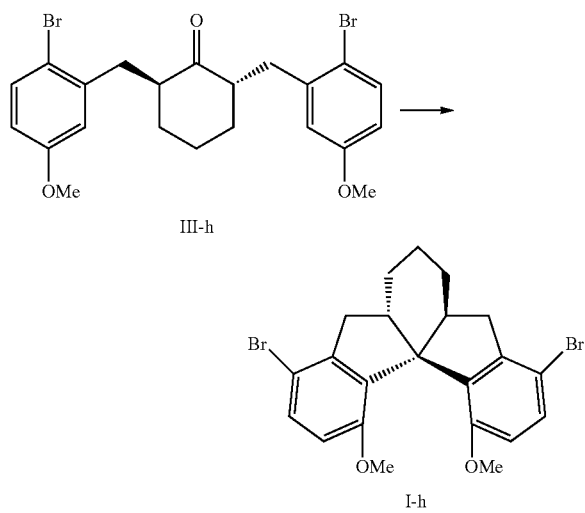

Taking the compound III-h (>99% ee) obtained in Example 5 as substrate, referring to the experimental methods disclosed in Example 13.The compound of III-h was reacted through intramolecular asymmetric cyclization reaction under the presence of 2 molar equivalent TiCl$_4$ to obtain the chiral spirobiindane skeleton compound I-h.

The product property and structure identification data: white solid, yield 93%, M.P. 192-193° C., $[\alpha]_D^{20}$=189.70 (c 1.0, CHCl$_3$) >99.6% ee. And the ee value of the product was determined by chiral HPLC. Chiralcel OD-H column; eluent, 2-propanol/hexane 0:100, temp, r.t.; flow rate, 0.8 mL/min; uv-vis detection, λ=230 nm; $t_R$ (major)=15.80 min; $t_R$ (minor)=23.00 min. $^1$H NMR (400 MHz, CDCl$_3$) δ7.24 (d, J=8.4 Hz, 2 H), 6.50 (d, J=8.4 Hz, 2 H), 3.44 (s, 6 H), 3.09 (dd, J=15.6, 7.6 Hz, 2 H), 2.92-2.88 (m, 2 H), 2.73 (dd, J=15.6, 6.4 Hz, 2 H), 1.56-1.51 (m, 4 H), 1.46-1.44 (m, 2 H); $^{13}$C NMR (100 MHz, CDCl$_3$) δ156.25, 145.89, 136.70, 130.30, 111.47, 111.09, 64.30, 55.49, 41.92, 39.46, 26.18, 17.88.

EXAMPLE 22

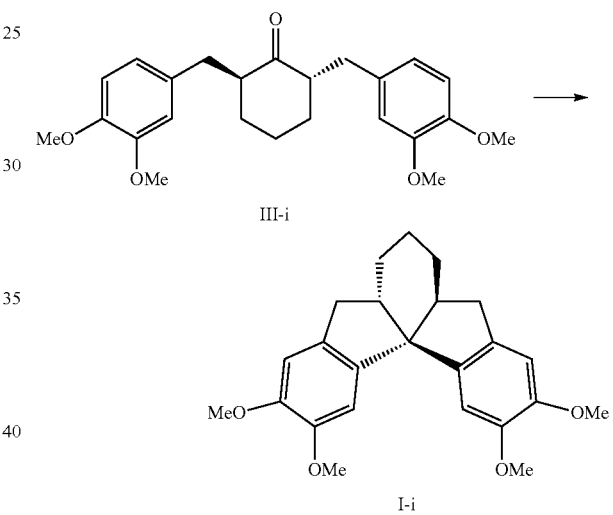

Taking the compound III-i (>99% ee) obtained in Example 5 as substrate, referring to the experimental methods disclosed in Example 13. The compound of III-i was reacted through intramolecular asymmetric cyclization reaction under the presence of 2 molar equivalent TiCl$_4$ to obtain the chiral spirobiindane skeleton compound I-i.

The product property and structure identification data: colourless liquid, yield 45%, 96% ee, $[\alpha]_D^{20}$=81.3 (c 1.10, CHCl$_3$). And the ee value of the product was determined by chiral HPLC. Chiralcel PC-3 column; eluent, acetonitrile/water 70:30; temp, r.t.; flow rate, 0.7 mL/min; uv-vis detection, λ=230 nm; $t_R$ (major)=6.34 min; $t_R$ (minor)=6.97 min. $^1$H NMR (400 MHz, CDCl$_3$) δ6.85 (s, 2 H), 6.31 (s, 2 H), 3.88 (s, 6 H), 3.72 (s, 6 H), 3.03 (dd, J=15.2, 7.2 Hz, 2 H), 2.67 (dd, J=15.2, 6 Hz, 2 H), 2.54-2.51 (m, 2 H), 1.59-1.49 (m, 4 H), 1.41-1.37 (m, 2 H). $^{13}$C NMR (100 MHz, CDCl$_3$) δ147.9, 147.8, 140.8, 133.8, 108.0, 106.3, 60.9, 55.8, 55.8, 44.3, 36.0, 27.5, 19.5. IR (neat) v 3001, 2933, 2857, 2834, 1702, 1607, 1590, 1513, 1463, 1451, 1417, 1337, 1258, 1235, 1192, 1155, 1140, 1026, 944, 854, 805, 749, 665, 638 cm$^{-1}$. HRMS-EI (m/z) M$^+$ calcd. for C$_{24}$H$_{28}$O$_4^+$ 380.1982 found 380.1985[M$^+$].

EXAMPLE 23

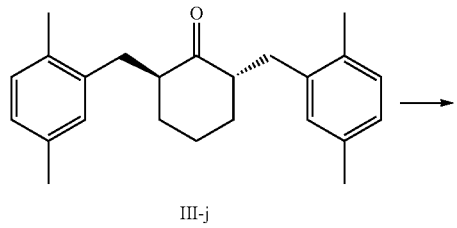

III-j

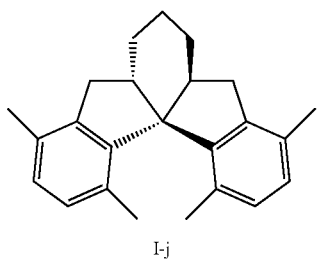

I-j

Taking the compound III-j (>99% ee) obtained in Example 5 as substrate, referring to the experimental methods disclosed in Example 13. The compound of III -j was reacted through intramolecular asymmetric cyclization reaction under the action of 2 molar equivalent TiCl$_4$ to obtain the chiral spirobiindane skeleton compound I-i.

The product property and structure identification data: colourless solid, yield 80%, 99% ee, M.P. 128-130° C., $[\alpha]_D^{20}$=90.0 (c 1.00, CHCl$_3$). And the ee value of the product was determined by chiral HPLC. Chiralcel PC-1 column; eluent, acetonitrile/water 80:20; temp, r.t.; flow rate, 0.7 mL/min; uv-vis detection, $\lambda$=230 nm; $t_R$ (major) =16.66 min; $t_R$ (minor)=17.67 min $^1$H NMR (400 MHz, CDCl$_3$) δ6.92 (d, J=7.2 Hz, 2 H), 6.80 (d, J=7.2 Hz, 2 H), 2.95-2.81 (m, 4 H), 2.66-2.61 (m, 2 H), 2.25 (s, 6 H), 1.86-1.79 (m, 2 H), 1.70 (s, 6 H), 1.66-1.53 (m, 4 H). $^{13}$C NMR (100 MHz, CDCl$_3$) δ146.5, 142.2, 131.6, 131.2, 128.9, 127.4, 63.8, 43.0, 34.9, 20.0, 18.9, 17.9, 14.6. IR (neat) v 2921, 2847, 1488, 1448, 1217, 1039, 879, 807, 753, 667 cm$^{-1}$. HRMS-EI (m/z) M$^+$ calcd. for C$_{24}$H$_{28}$$^+$316.2186, found 316.2187 [M$^+$].

EXAMPLE 24

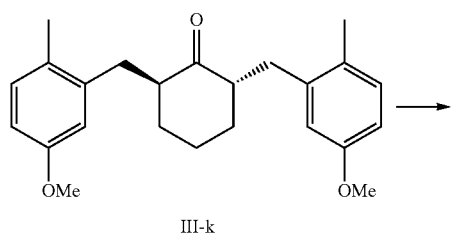

III-k

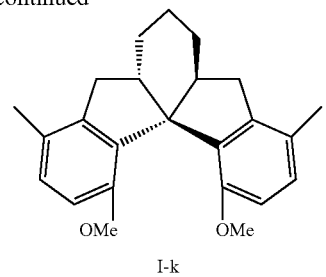

I-k

Taking the compound III-k (>99% ee) obtained in Example 5 as substrate, referring to the experimental methods disclosed in Example 13. The compound of III-k was reacted through intramolecular asymmetric cyclization reaction under the presence of 2 molar equivalent TiCl$_4$ to obtain the chiral spirobiindane skeleton compound I-k.

The product property and structure identification data: white solid, yield 78%, M.P. 73-75° C., $[\alpha]_D^{20}$=109.7 (c 1.05, CHCl$_3$), 94% ee. And the ee value of the product was determined by chiral HPLC. Chiralcel PC-1 column; eluent, acetonitrile/water 80:20; temp, r.t.; flow rate, 0.7 mL/min; uv-vis detection, $\lambda$=230 nm; $t_R$ (major)=13.17 min; $t_R$ (minor)=15.42 min. $^1$H NMR (400 MHz, CDCl$_3$) δ6.94 (d, J=8.4 Hz, 2 H), 6.57 (d, J=8.4 Hz), 3.41 (s, 6 H), 3.04 (dd, J=15.2, 7.6 Hz, 2 H), 2.97-2.94 (m, 2 H), 2.64 (dd, J=14.8, 6.0 Hz, 2 H), 2.25 (s, 6 H), 1.60-1.55 (m, 2 H), 1.49-1.45 (m, 2 H). $^{13}$C NMR (100 MHz, CDCl$_3$) δ155.4, 145.1, 135.4, 127.9, 126.1, 110.2, 62.3, 55.9, 42.4, 36.8, 26.9, 18.5, 18.4. IR (neat) v 2919, 2848, 1977, 1602, 1490, 1463, 1437, 1378, 1313, 1255, 1220, 1183, 1161, 1087, 1034, 964, 937, 870, 844, 795, 754, 721, 666, 611. HRMS-EI (m/z) calcd. for C$_{28}$H$_{28}$O$_2$$^+$348.2084; found 348.2089 [M$^+$].

EXAMPLE 25

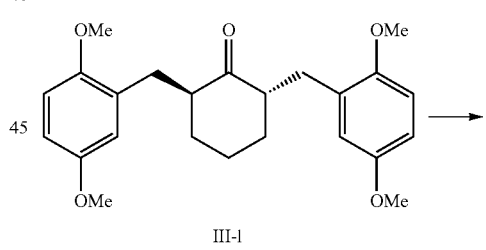

III-l

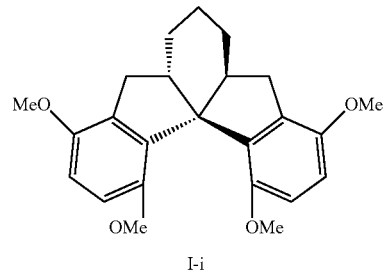

I-i

Taking the compound III-I (>99% ee) obtained in Example 5 as substrate, referring to the experimental methods in Example 13, the compound of III-I was reacted through intramolecular asymmetric cyclization reaction under the presence of 2 molar equivalent TiCl$_4$ to obtain the chiral spirobiindane skeleton compound I-I.

The product property and structure identification data: Colorless oily liquid, yield 85%, [α]$_D^{20}$=95.2 (c 1.10, CHCl$_3$), 90% ee. And the ee value of the product was determined by chiral HPLC. Chiralcel PC-2 column; eluent, acetonitrile/water 60:40; temp, r.t.; flow rate, 0.7 mL/min; uv-vis detection, λ=230 nm; t$_R$ (minor)=33.33 min; t$_R$ (major)=35.19 min. $^1$H NMR (400 MHz, CDCl$_3$) δ6.65 (d, J=8.8 Hz, 2 H), 6.59 (d, J=8.8 Hz, 2 H), 3.82 (s, 6 H), 3.40 (s, 6 H), 3.09 (dd, J=15.2, 7.6 Hz, 2 H), 2.94-2.91 (m, 2 H), 2.67 (dd, J=15.6, 6.4 Hz, 2 H), 1.59-1.52 (m, 4 H), 1.48-1.45 (m, 2 H). $^{13}$C NMR (100 MHz, CDCl$_3$) δ151.6, 150.4, 137.6, 133.9, 110.7, 108.8, 62.7, 56.3, 55.7, 42.8, 34.5, 26.6, 18.3. IR (neat) v 2999, 2919, 2850, 2832, 2050, 1810, 1596, 1488, 1460, 1448, 1436, 1329, 1312, 1297, 1254, 1239, 1213, 1186, 1164, 1117, 1094, 1073, 1049, 1003, 987, 975, 953, 929, 908, 875, 795, 751, 714, 652, 637 cm$^{-1}$. HRMS (ESI) m/z: calcd. for C$_{24}$H$_{32}$NO$_4^+$: 398.2326, Found: 398.2324 ([M+NH$_4$]$^+$).

EXAMPLE 26

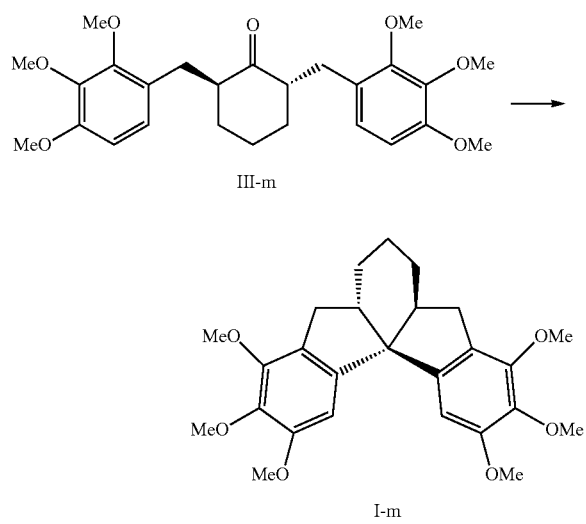

III-m

I-m

Taking the compound III-m (>99% ee) obtained in Example 5 as substrate, referring to the experimental methods in Example 13, the compound of III-m was reacted through intramolecular asymmetric cyclization reaction under the presence of 2 molar equivalent TiCl$_4$ to obtain the chiral spirobiindane skeleton compound I-m.

The product property and structure identification data: Colorless oily liquid, yield 56%, [α]$_D^{20}$=51.8 (c 1.10, CHCl$_3$), 59.9% ee. And the ee value of the product was determined by chiral HPLC. Chiralcel PA-2 column; eluent, acetonitrile/water 60:40; temp, r.t.; flow rate, 0.7 mL/min; uv-vis detection, λ=230 nm; t$_R$ (major)=8.89 min; t$_R$ (minor) =14.31 min. $^1$H NMR (400 MHz, CDCl$_3$) δ6.11 (s, 2 H), 3.94 (s, 6 H), 3.87 (s, 6 H), 3.71 (s, 6 H), 3.04 (dd, J=15.6, 7.2 Hz, 2 H), 2.68 (dd, J=15.6, 6.0 Hz, 2 H), 2.51-2.49 (m, 2 H), 1.64-1.50 (m, 4 H), 1.42-1.37 (m, 2 H). $^{13}$C NMR (100 MHz, CDCl$_3$) δ152.8, 150.0, 144.4, 140.3, 126.3, 102.4, 61.8, 61.0, 60.5, 56.1, 43.8, 32.9, 27.5, 19.5. IR (neat) v 2927, 2849, 1586, 1463, 1411, 1324, 1299, 1229, 1196, 1115, 1096, 1034, 947, 910, 831, 793, 750 cm$^{-1}$.

EXAMPLE 26-1

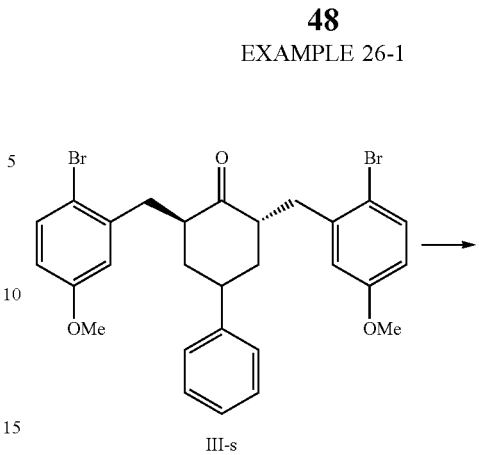

III-s

I-s'

Taking the compound III-s (>99% ee) obtained in Example 5 as substrate, referring to the experimental methods in Example 13, the compound of III-s was reacted through intramolecular asymmetric cyclization reaction under the presence of 2 molar equivalent TiCl$_4$, and the chiral spirobiindane skeleton compound I-s'.

The product property and structure identification data: White solid, yield 82%, [α]$_D^{20}$=141.7 (c 1.10, CHCl$_3$), >99% ee. And the ee value of the product was determined by chiral HPLC. Chiralcel IA-3 column; eluent, 2-propanol/hexane 10:90; temp, r.t.; flow rate, 0.5 mL/min; uv-vis detection, λ=214 nm; t$_R$ (major)=7.38 min; t$_R$ (minor)=8.54 min. $^1$H NMR (400 MHz, CDCl$_3$) δ7.32-7.15 (m, 7 H), 6.60 (d, J=8.8 Hz, 1 H),6.49 (d, J=8.8 Hz, 1 H), 4.06-3.99 (m, 1 H), 3.64 (s, 3 H), 3.36-3.29 (m, 4 H), 3.12-2.99 (m, 2 H), 2.93-2.87 (m, 1 H), 2.55 (d, J=16.0 Hz, 1 H), 2.42-2.36 (m, 1 H), 1.95-1.91 (m, 1 H), 1.86-1.83 (m, 1 H), 1.77-1.69 (m, 1 H), 1.41-1.31 (m, 1 H). $^{13}$C NMR (100 MHz, CDCl$_3$) δ157.2, 155.9, 148.1, 146.9, 144.2, 138.8, 133.2, 130.7, 130.4, 128.3, 126.9, 126.0, 112.3, 111.3, 111.21, 111.17, 64.0, 55.7, 55.5, 45.4, 42.1, 40.3, 38.8, 38.1, 36.4, 33.4. IR (neat) v2923, 1574, 1469, 1259, 1191, 1082, 1021, 971, 849, 797, 759, 698, 671, 659, 642cm$^{-1}$. HRMS-EI (m/z) calcd. for C$_{28}$H$_{26}$Br$_2$O$_2^+$: 552.0294, found: 552.0298 [M$^+$].

EXAMPLE 26-2

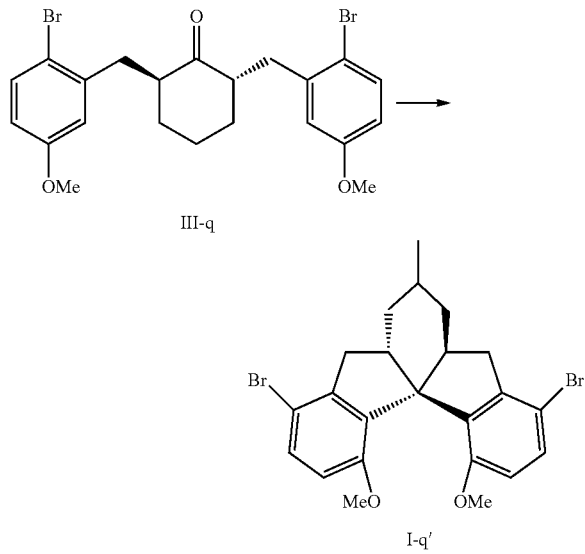

Taking the compound III-q (>99% ee) obtained in Example 5 as substrate, referring to the experimental methods in Example 13, the compound of III-q was reacted through intramolecular asymmetric cyclization reaction under the presence of 2 molar equivalent TiCl$_4$ to obtain the chiral spirobiindane skeleton compound I-q'.

The product property and structure identification data: White solid, yield 78%, $[\alpha]_D^{20}$=210.6 (c 1.10, CHCl$_3$), >99% ee. And the ee value of the product was determined by chiral HPLC. Chiralcel IA-3 column; eluent, 2-propanol/hexane 10:90; temp, r.t.; flow rate, 0.5 mL/min; uv-vis detection, λ=214 nm; $t_R$ (major)=7.66 min; $t_R$ (minor)=8.23 min. $^1$H NMR (400 MHz, CDCl$_3$) δ7.27 (d, J=8.8 Hz, 1 H), 7.20 (d, J=8.4 Hz, 1 H),6.55 (d, J=8.8 Hz, 1 H),6.44 (d, J=8.4 Hz, 1 H), 3.81-3.75 (m, 1 H), 3.60 (s, 3 H), 3.29-3.24 (m, 4 H), 3.01 (dd, J=16.0, 8.4 Hz, 1 H), 2.85 (dd, J=16.0, 10.8 Hz, 1 H), 2.51 (d, J=15.6 Hz, 1 H), 2.27-2.21 (m, 1 H), 1.77-1.59 (m, 3 H), 1.18-1.11 (m, 1 H), 0.87-0.78 (m, 4 H). $^{13}$C NMR (100 MHz, CDCl$_3$) δ157.1, 155.9, 148.1, 144.5, 139.0, 133.6, 130.6, 130.3, 112.2, 111.3, 111.25, 111.20, 64.3, 55.7, 55.5, 44.8, 42.1, 40.2, 39.5, 38.4, 34.4, 24.7, 22.5.IR (neat) v2946, 1573, 1470, 1274, 1257, 1188, 1099, 1077, 1047, 987, 960, 805, 796, 764, 670, 614cm$^{-1}$. HRMS-EI (m/z) calcd. for C$_{23}$H$_{24}$Br$_2$O$_2$$^+$: 490.0138, found: 490.0141 [M$^+$].

EXAMPLE 26-3

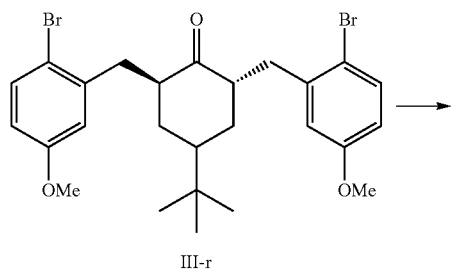

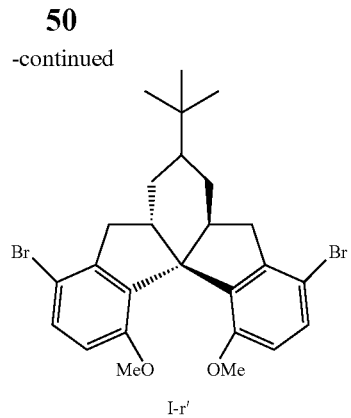

Taking the compound III-r (>99% ee) obtained in Example 5 as substrate, referring to the experimental methods in Example 13, the compound of III-r was reacted through intramolecular asymmetric cyclization under the presence of 2 molar equivalent TiCl$_4$ to obtain the chiral spirobiindane skeleton compound I-r'.

The product property and structure identification data: White solid, yield 75%, $[\alpha]_D^{20}$=13.2 (c 1.10, CHCl$_3$), 97% ee. And the ee value of the product was determined by chiral HPLC. Chiralcel IA-3 column; eluent, 2-propanol/hexane 10:90; temp, r.t.; flow rate, 0.5 mL/min; uv-vis detection, λ=214 nm; $t_R$ (major)=7.38 min; $t_R$ (minor)=8.54 min. $^1$H NMR (400 MHz, CDCl$_3$) δ7.27 (d, J=8.4 Hz, 1 H), 7.21 (d, J=8.4 Hz, 1 H),6.55 (d, J=8.8 Hz, 1 H),6.45 (d, J=8.4 Hz, 1 H), 3.77-3.60 (m, 1 H), 3.60 (s, 3 H), 3.37-3.32 (m, 4H), 3.08 (dd, J=16.0, 8.4 Hz, 1 H), 2.82 (dd, J=16.0, 9.6 Hz, 1 H), 2.53 (d, J=15.6 Hz, 1 H), 2.26-2.20 (m, 1 H), 1.72-1.61 (m, 2 H), 1.37-1.23 (m, 2 H), 0.95-0.86 (m, 1 H), 0.83 (s, 9 H). $^{13}$C NMR (100 MHz, CDCl$_3$) δ157.1, 155.9, 147.9, 144.5, 138.8, 133.9, 130.5, 130.3, 112.0, 111.2, 111.17, 111.12, 64.6, 55.6, 55.5, 45.5, 42.6, 40.3, 40.2, 39.0, 32.4, 32.3, 27.7, 27.4. IR (neat) v 2922, 1573, 1470, 1274, 1258, 1098, 1077, 961, 796, 766, 670, 615 cm$^{-1}$. HRMS-EI (m/z) calcd. for C$_{26}$H$_{30}$Br$_2$O$_2$$^+$: 532.0607, found: 532.0621 [M$^+$].

EXAMPLE 27

Catalytic Asymmetric Hydrogenation reaction and ring closing reaction can be used as one-pot reaction, with compound II as raw material, and without the separation of intermediate compound III. It carries out by adding a proper amount of TiCl$_4$ to the hydrogenated reaction mixture to synthesize compound I. In the example of the present invention, such as, the compound I-h was synthesized by one pot reaction of asymmetric oxidation and ring closing reaction to synthesize compound II-h. It explains a typical experimental method for the synthesis of compound I from the compound II.

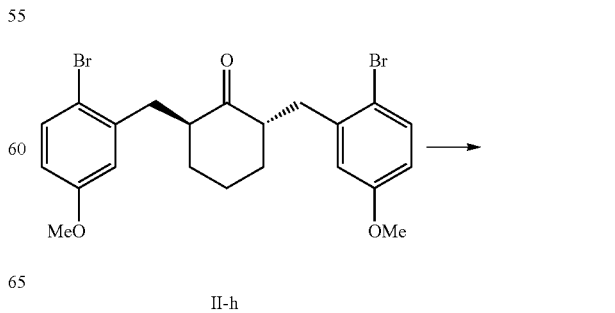

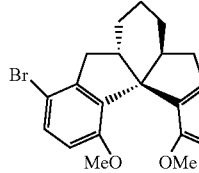

I-h

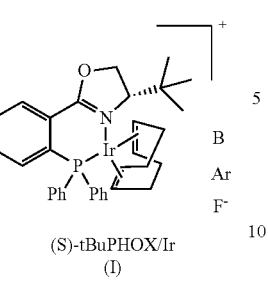

(S)-tBuPHOX/Ir
(I)

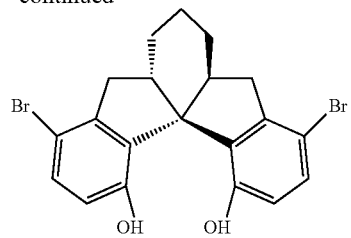

I-n

Under argon atmosphere, into an anhydrous anaerobic treatment of the Hydrogenated bottle(150 mL), were added catalyst(S)-$^t$BuPHOX/Ir(I) (96.0 mg, 0.061 mmol), the substrate compound II-h (6.15 g, 12.55 mmol) and anhydrous methylene dichloride (75 mL). Transferring hydrogen in the hydrated bottle to the autoclave in the glove box, replacing hydrogen three times until the hydrogen pressure to 50 atm. The reaction was carried out for 12 hrs at room temperature. After carefully emptying hydrogen, under the protection of argon, the light yellow reacton liquid was quickly transferred to another three bottle (500-ml), the anhydrous dichloromethane175 mL was added into, the reaction mixture was cooled under ice bath condition,and TiCl$_4$(2.75 mL, 25.1 mmol)was dropped slowly, the reaction was reacted for 30 minutes at the temperature of 0° C., warmed back to room temperature slowly, and continued stirred for 6 hours. The reaction was quenched by adding 100 mL water, the reaction mixture was extracted with dichloromethane for three times(5 mL×3), the organic layer was combined and dried over Na$_2$SO$_4$ and filtered to remove desiccant, after the filtrate was decompressed, the residue was separated and purified by silica gel column chromatography(petroleum ether/ethyl acetate=50:1). The white solid I-h was obtained (5.02 g, yield 84%, >99% ee).

EXAMPLE 28 the Preparation Method of 7,7'-dibromo chiral spirobiindane skeleton spirobiindane-7,7'-diol I-n

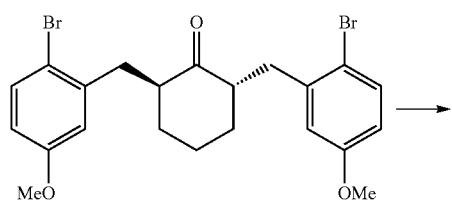

II-h

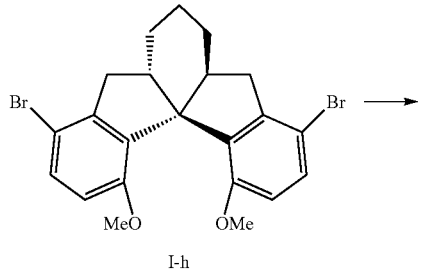

I-h

As shown in the above formula, the first step is to adopt the method described in example 27, the compound II-h was used as starting material to obtain the compound of I-h by one-pot asymmetric hydrogenation and ring closing reaction with a yield of 84% cacluated by two steps total yield, and with an enantioselective of more than 99% ee.

In second step, the operation method of removing methyl group of compound I-h by BBr$_3$ reagent: In argon atmosphere, into anhydrous anaerobic treatment schlenk bottle (100 mL),were added (1S, 2S, 2'S)-I-h (5.02 g, 10.55 mmol), methylene dichloride (35.0 mL), the temperature was cooled to −78° C. was added BBr$_3$ (4 M in CH$_2$Cl$_2$) (6.59 mL, 26.38 mmol) by dropwise. The reaction mixture was continued to stir for 12 hours. The reaction was quenched by adding 100 mL water and the reaction mixture was extracted with dichloromethane(20 mL×3), the organic layer was combined and dried over Na$_2$SO$_4$, and filtered to remove desiccant, after the filtrate was decompressed, the residue was separated and purified by silica gel column chromatography (petroleum ether/ethyl acetate=50:1). The white solid I-n was obtained (4.02 g, 85%)

The product property and structure identification data: White solid, yield 85%, M.p. 132-133° C., $[\alpha]_D^{20}$=301.63 (c 1.0, CHCl$_3$). $^1$H NMR (400 MHz, CDCl$_3$) δ7.25 (d, J=8.0 Hz, 2 H), 6.50 (d, J=8.8 Hz, 2 H), 4.58 (s, 2 H), 3.07-3.00 (m, 2 H), 2.90-2.81 (m, 4 H), 1.72-1.66 (m, 2 H), 1.60-1.55 (m, 4 H); $^{13}$C NMR (75 MHz, CDCl$_3$) δ152.36, 145.39, 132.19, 132.16, 116.85. 111.34, 62.75, 42.60, 38.43, 23.00, 16.09; IR (neat) ν 3470, 3392, 2921, 2913, 2851, 1573, 1461, 1422, 1291, 1211, 1184, 1084, 1065, 1045, 806, 718, 677, 660, 627 cm$^{-1}$; EI-MS (70 eV), m/z=450 ([M]$^+$), 369, 290, 263, 184, 145, 124, 115, 107, 94; HRMS-EI (m/z) calcd. for C$_{20}$H$_{18}$O$_2$Br$_2^+$, 447.9668, found, 447.9670 [M]$^+$.

EXAMPLE 29

The Preparation Method of chiral spirobiindane skeleton spirobiindane-7,7'-diol I-o

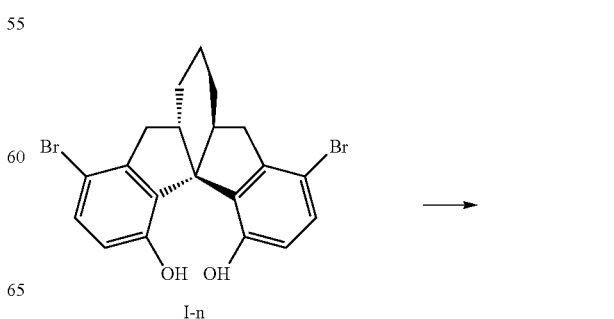

I-n

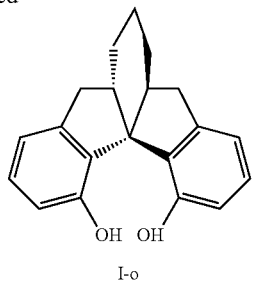

I-o

Starting from the compound I-n synthesized from example 28, reacted through a reaction step of Pd/C catalytic hydrogenation reaction and debromination reaction to obtain chiral spirobiindane skeleton spirobiindane-7,7'-diol I-o with a yield of 95%. The specific operation method are as follows: into hydrogenated reaction bottle, were added (1S, 2S, 2'S)-I-n (4.02 g, 8.97 mmol), methanol (20.0 mL), acetic acid (6 mL) and 10% Pd/C (0.40 g),the hydrogenated reaction bottle was transferred to the autoclave and was replaced with hydrogen for three times until a hydrogen pressure of 20 atm. The reaction mixture was reacted for 12 hrs at room temperature, the hydrogen was carefully vented, the reaction mixture was removed Pd/C by filtration, the filtrate was decompressed to remove ethanol, the mixture was extracted with saturated NaHCO$_3$, ethyl acetate (20 mL×3) for three times, the organic layer was combined and dried over Na$_2$SO$_4$. The filtrate was decompressed to remove desiccant to obtain the (1S, 2S, 2'S)-I-o (2.54 g) product.

The product property and structure identification data: colorless liquid, yield 95%, >99% ee. [α]$_D^{20}$=157.9 (c 1.0, CHCl$_3$). And the ee value of the product was determined by chiral HPLC. Chiralcel AD-H column. Conditions: hexane/ isopropanol=80:20; flow rate=1.0 mL/min; UV detection at 230 nm; t$_R$=4.84 min(minor), 9.42 min(major). $^1$H NMR (400 MHz, CDCl$_3$) δ7.14 (t, J=7.6 Hz, 2 H), 6.89 (d, J=7.6 Hz, 2 H), 6.61 (d, J=8.0 Hz, 2 H), 4.60 (s, 2 H), 3.03 (dd, J=18.4, 10.8 Hz, 2 H), 2.94-2.89 (m, 4 H), 1.67-1.55 (m, 6 H); $^{13}$C NMR (100 MHz, CDCl$_3$) δ153.50, 145.67, 130.72, 129.40, 118.02, 114.76, 60.20, 43.65, 36.92, 24.05, 16.90; IR (KBr pellet) v 3588, 3568, 2924, 2846, 1609, 1586, 1485, 1460, 1340, 1261, 1225, 1190, 1137, 1107, 986, 933, 779, 734 cm$^{-1}$; EI-MS (70 eV), m/z=292 ([M]$^+$), 290, 207, 184, 169, 78, 51; HRMS-EI (m/z) [M]$^+$ calcd for C$_{20}$H$_{20}$O$_2$, 292.1463, found, 292.1465. Anal. calcd. for C$_{20}$H$_{20}$O$_2$: C, 82.16; H, 6.89%; Found: C, 82.46; H, 7.04%.

EXAMPLE 30

Referring to the experimental methods described in examples 28 and 29, (R)-$^t$BuPHOX/Ir(I) is used as an asymmetric hydrogenation catalyst to obtain chiral spirobiindane skeleton spirobiindane-7,7'-diol I-p.

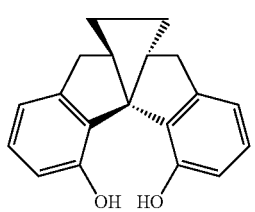

I-p (1R,2R,2'R)-I-p: white solid, yield 66%; >99% ee, M.p. 53-54° C. [α]$_D^{20}$=−201.7 (c 0.70, CHCl$_3$); $^1$H NMR (400 MHz, CDCl$_3$) δ7.16 (t, J=7.6 Hz, 2 H), 6.85 (d, J=7.2 Hz, 2 H), 6.64 (d, J=7.6 Hz, 2 H), 4.41 (s, 6 H), 3.44 (dd, J=16.8, 9.2 Hz, 2H), 3.00-2.98 (m, 2H), 2.80 (dd, J=17.2, 4.8 Hz, 2 H), 2.05-2.01 (m, 2 H), 1.60-1.56 (m, 2 H); $^{13}$C NMR (100 MHz, CDCl$_3$) δ152.95, 145.09, 131.90, 129.52, 117.52, 114.14, 70.50, 50.85, 38.76, 33.15; IR (neat) v 3514, 3031, 2952, 2936, 2915, 1849, 2837, 1610, 1585, 1479, 1462, 1271, 1161, 989, 780, 772, 742, 721 cm$^{-1}$; EI-MS (70 eV), m/z=278 ([M]$^+$), 250, 231, 202, 189, 171, 165, 145, 115, 91, 77; HRMS-EI (m/z) calcd for C$_{19}$H$_{18}$O$_2$, 278.1307, found, 278.1310 [M]$^+$. Anal. calcd. for C$_{19}$H$_{18}$O$_2$: C, 81.99; H, 6.52%; Found: C, 81.82; H, 6.62%.

EXAMPLE 31

Referring to the experimental methods described in examples 28 and 29, (R)-$^t$BuPHOX/Ir(I) is used as an asymmetric hydrogenation catalyst to obtain chiral spirobiindane skeleton spirobiindane-7,7'-diol I-q.

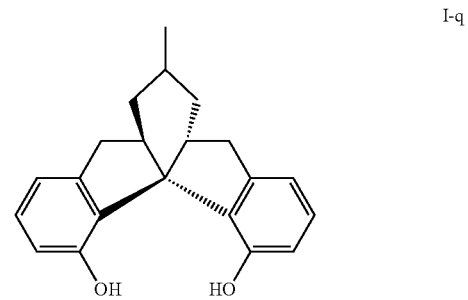

I-q (1R,2R,2'R)-I-q: white solid, yield 59%; >99% ee. M.p. 132-133° C., [α]$_D^{20}$=−217.6 (c 0.74, CHCl$_3$); $^1$H NMR (400 MHz, CDCl$_3$) δ7.18 (t, J=7.6 Hz, 1 H), 7.05 (t, J=7.6 Hz, 1 H), 6.95 (d, J=7.6 Hz, 1 H), 6.84 (d, J=7.2 Hz, 1 H), 6.59 (d, J=8.0 Hz, 1H), 6.53 (d, J=8.0 Hz, 1 H), 4.89 (s, 1 H), 4.46 (s, 1 H), 3.74-3.71 (m, 1 H), 3.31 (dd, J=15.6, 6.8 Hz, 1 H), 3.06 (dd, J=15.6, 12.0 Hz, 1 H), 2.85 (dd, J=15.6, 8.4 Hz, 1 H), 2.57 (d, J=8.0 Hz, 1 H), 2.39-2.33 (m, 1 H), 1.82-1.77 (m, 2 H), 1.65-1.57 (m, 1 H), 1.25-1.17 (m, 1 H), 0.90-0.81 (m, 4 H); $^{13}$C NMR (100 MHz, CDCl$_3$) δ154.38, 152.94, 146.58, 144.73, 132.74, 129.84, 128.86, 128.31, 118.99, 117.20, 115.44, 114.58, 45.80, 42.85, 39.34, 38.26, 35.99, 33.72, 24.53, 22.60; IR (neat) v 3452, 3387, 2924, 2898, 1583, 1472, 1456, 1286, 1248, 1233, 1199, 981, 776, 734 cm$^{-1}$; EI-MS (70 eV), m/z=306 ([M]$^+$), 249, 231, 199, 189, 157, 145, 115, 107, 91, 71, 57, 41; HRMS-EI (m/z) calcd for C$_{21}$H$_{22}$O$_2$, 302.1620, found, 306.1617 [M]$^+$.

EXAMPLE 32

Referring to the experimental methods described in examples 28 and 29, (R)-$^t$BuPHOX/Ir(I) is used as an asymmetric hydrogenation catalyst to obtain chiral spirobiindane skeleton spirobiindane-7,7'-diol I-r.

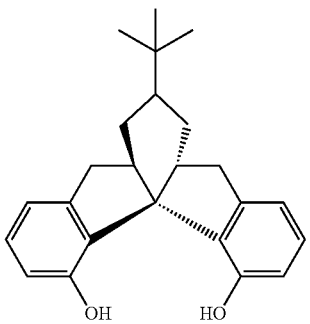

(1R,2R,2'R)-I-r: white solid, yield 50%; >99% ee, M.p. 112-113° C., $[\alpha]_D^{20}=-167.4$ (c 0.835, CHCl$_3$); $^1$H NMR (400 MHz, CDCl$_3$) δ7.01 (t, J=7.6 Hz, 1 H), 6.95 (t, J=7.6 Hz, 1 H), 6.82 (d, J=7.6 Hz, 1 H), 6.76 (d, J=7.2 Hz, 1 H), 6.45 (d, J=7.6 Hz, 1 H), 6.31 (d, J=8.0 Hz, 1 H), 5.55 (s, 1 H), 4.57 (s, 1 H), 3.90-3.88 (m, 1 H), 3.28 (dd, J=16.0, 6.4 Hz, 1 H), 3.01 (dd, J=15.2, 12.0 Hz, 1 H), 2.78 (dd, J=15.6, 8.0 Hz, 1 H), 2.46 (d, J=8.0 Hz, 1 H), 2.27-2.23 (m, 1 H), 1.77-1.73 (m, 1 H), 1.62-1.58 (m, 1 H), 1.39-1.35 (m, 1 H), 1.29-1.24 (m, 1 H), 0.88-0.80 (m, 10H); $^{13}$C NMR (100 MHz, CDCl$_3$) δ154.80, 152.60, 146.44, 144.76, 133.35, 129.87, 128.92, 118.80, 117.49, 115.64, 114.62, 60.94, 46.92, 42.52, 40.05, 39.74, 36.21, 32.19, 31.89, 27.62, 26.74; IR (neat) v 3503, 3461, 2930, 2854, 1609, 1584, 1458, 1279, 1225, 1197, 1155, 990, 776, 733, 721 cm$^{-1}$; EI-MS (70 eV), m/z=348 ([M]$^+$), 291, 241, 231, 202, 185, 165, 145, 107, 57, 41; HRMS-EI (m/z) calcd for C$_{24}$H$_{28}$O$_2$, 348.2089, found, 348.2093 [M]$^+$.

EXAMPLE 33

Referring to the experimental methods described in examples 28 and 29, (R)-$^t$BuPHOX/Ir(I) is used as an asymmetric hydrogenation catalyst to obtain chiral spirobiindane skeleton spirobiindane-7,7'-diol I-s.

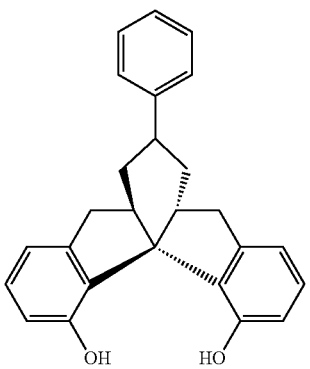

(1R,2R,2'R)-I-s: white solid, yield 50%; >99% ee, M.p. 93-94° C., $[\alpha]_D^{20}=-222.5$ (c 0.545, CHCl$_3$); $^1$H NMR (300 MHz, CDCl$_3$) δ7.13-7.28 (m, 6 H), 7.05 (t, J=10.0 Hz, 1 H), 6.93 (d, J=9.6 Hz, 1 H), 6.86 (d, J=10.0 Hz, 1 H), 6.54 (t, J=9.2 Hz, 2 H), 5.04 (s, 1 H), 4.49 (s, 1 H), 3.98 (m, 1 H), 3.35 (dd, J=21.2, 8.4 Hz, 1 H), 3.21 (dd, J=20.4, 16.8 Hz, 1 H), 3.00-2.86 (m, 2 H), 2.57-2.44 (m, 2 H), 2.02-1.93 (m, 1 H), 1.84-1.72 (m, 2 H), 1.34 (dd, J=33.2, 16.4 Hz, 1 H); $^{13}$C NMR (75 MHz, CDCl$_3$) δ154.57, 152.89, 146.68, 146.47, 144.48, 132.79, 129.97, 128.54, 128.34, 128.32, 126.90, 125.99, 119.06, 117.30, 115.61, 114.72, 60.55, 46.39, 42.57, 39.34, 38.00, 36.27, 35.86, 32.82; IR (neat) v 3327, 3026, 2921, 2845, 1604, 1457, 1435, 1345, 1328, 1267, 988, 779, 764, 753, 737, 699 cm$^{-1}$; EI-MS (70 eV), m/z=368 ([M]$^+$), 261, 250, 231, 202, 127, 107, 85, 71, 57, 43; HRMS-EI (m/z) calcd for C$_{26}$H$_{24}$O$_2$, 368.1776, found, 368.1771 [M]$^+$.

EXAMPLE 34 the Preparation Method of chiral spirobiindane skeleton phosphoramidite ligand I-t)

Using the same method as example 28, starting from II-h, used (R)-$^t$BuPHOX/Ir(I) catalyst, the asymmetric enantiomer ent-I-o of compound I-o can be obtained by dehydrogenation of bromine according to the method of Example 29 through the one-pot asymmetric hydrogenation/cyclization reaction. As shown in the following formula, the corresponding monophosphate ligand I-t can be synthesized by the reaction of diphenol ent-I-o with dimethylphosphoramidous dichloride under alkaline conditions.

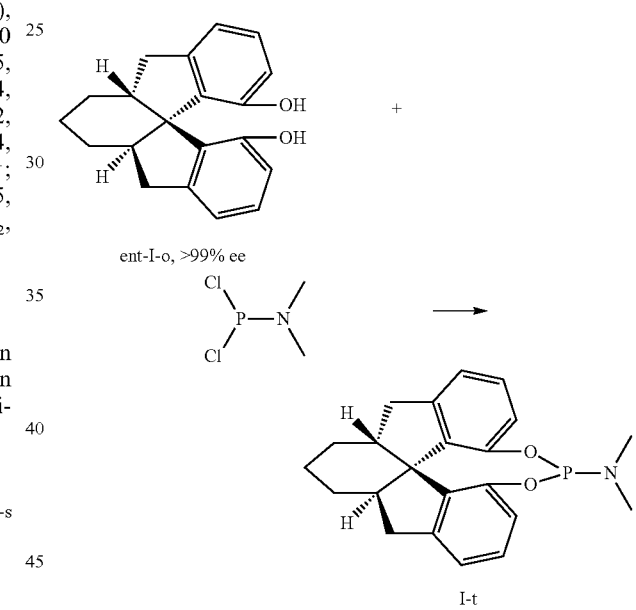

Operation method: into anhydrous anaerobic treatment Schlenk tube (15 mL), in argon atmosphere,were added spirobiindane-7,7'-diol ent-I-o(0.30 mmol), THF(3.5 mL) and Et$_3$N(0.15 mL), the temperature was cooled to 0° C., was add slowly dimethylphosphoramidous dichloride (37.9 μL, 0.33 mmol). After the dropping is finished, warmed back slowly to room temperature, the reaction mixture was reacted for 12 hrs at room temperature and was decompressed to remove most of the solvent. The silica gel column was flushed with solvent (petroleum ether/three ethylamine=20:1),the residue was separated and purified by silica gel column chromatography (Eluent, petroleum ether/ethyl acetate=20:1), product I-t was obtain by drying with oil pump.

Product compound I-t white solid, yield 86%, M.p. 89-90° C., $[\alpha]_D^{20}=+234.95$ (c 0.50, CHCl$_3$); $^1$H NMR (400 MHz, CDCl$_3$) δ7.11 (t, J=7.6 Hz, 1 H), 7.03 (t, J=7.6 Hz, 1 H), 6.93-6.88 (m, 3 H), 6.54 (d, J=8.0 Hz,1 H), 3.26-3.16 (m, 2 H), 2.90-2.69 (m, 4 H), 2.19 (d, J=8.8 Hz, 6 H), 1.95-1.88

(m, 2 H), 1.68-1.63 (m, 2 H); $^{13}$C NMR (100 MHz, CDCl$_3$) δ149.18 (d, J=5.3 Hz), 145.88 (d, J=5.6 Hz), 145.57 (d, J=2.1 Hz), 144.80, 128.72 (d, J=2.0 Hz), 128.59, 121.29 (d, J=1.7 Hz), 121.03 (d, J=6.5 Hz), 120.56 (d, J=2.5 Hz), 119.46 (d, J=0.8 Hz), 61.09, 46.10, 45.85 (d, J=1.1 Hz), 36.57, 35.98, 35.16, 34.97, 19.04, 19.01, 14.93; $^{31}$P NMR (161 MHz, CDCl$_3$) δ125.38; IR (neat) v 2926, 2891, 2883, 2864, 2841, 1582, 1459, 1441, 1290, 1235, 1224, 1190, 1159, 1140, 1027, 972, 925, 803, 790, 775, 742, 725, 692, 678 cm$^{-1}$; ESI-MS (m/z): 365 ([M]$^+$); HRMS-ESI (m/z): calcd. for C$_{22}$H$_{25}$NO$_2$P$^+$: 366.1617, found: 366.1626 ([M+H]$^+$).

EXAMPLE 35

Asymmetric Hydrogenation of the Catalyticα-Dehydrogenated Amino Acid Methyl Esters by Using Rh(I)/chiral spirobiindane skeleton phosphoramidite ligand I-t)

In this example, the asymmetric hydrogenation reaction of the α-dehydrogenated amino acid methyl ester catalyzed by the complex formed by chiral spirobiindane skeleton phosphoramidite ligand I-t and [Rh(COD)$_2$OTf] as a chiral catalyst is used to illustrate the application of chiral spirobiindane skeleton compound in asymmetric catalysis in the present invention.

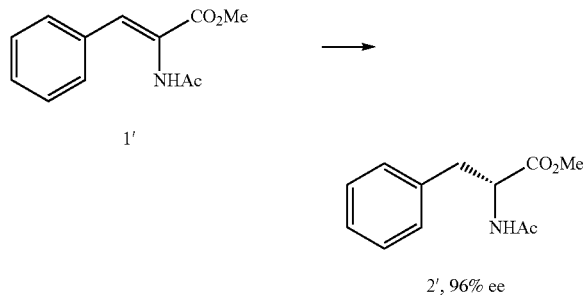

Operation method: under argon atmosphere, anhydrous anaerobic treatment hydrogenated reaction bottle, were added [Rh(COD)$_2$]OTf (1.17 mg, 0.0025 mmol) and I-t, then CH$_2$Cl$_2$(2.5 mL)was added after replaced with argon for three times. The hydrogenated reaction bottle was transferred to the glove box, α-dehydrogenated amino acid methyl ester substrate 1'(54.8 mg, 0.25 mmol) was added into it. The hydrogenated bottle was put to the autoclave. The autoclave was replaced with hydrogen for three times until the hydrogen pressure of 20 atm. The reaction was stirred for reaction of an hour of 12 h at room temperature, the reaction was stopped, the hydrogen was vented, the reaction mixture was decompressed to remove solvent, the conversion rate was determined by $^1$H NMR, and the residue was separated from ethyl acetate by a short silica gel column to obtain hydride 2'. White solid, yield >99%, M.p. 85-87° C., 96% ee, [α]$_D^{20}$=-97.92 (c 1.0, CHCl$_3$); $^1$-1 NMR (400 MHz, CDCl$_3$) δ7.21-7.31 (m, 3 H), 7.09-7.12 (m,2 H), 6.22 (d, J=6.4 Hz,1 H), 4.84-4.90 (m, 1 H), 3.71 (s,3 H), 3.04-3.16 (m, 2 H), 1.97 (s, 3 H). The cc value of the product 2' was determined by chiral high performance liquid chromatography, the chiral column was a Chiralcel AS-H chiral column from Japan Daicel Corporation; Conditions: hexane/isopropanol=92:8; flow rate=1.0 mL/min; UV detection at 230 nm; t$_R$=14.50 min(major), 18.99 min(minor)

EXAMPLE 36

Synthesis of chiral spirobiindane skeleton phosphoramidite ligand I-u)

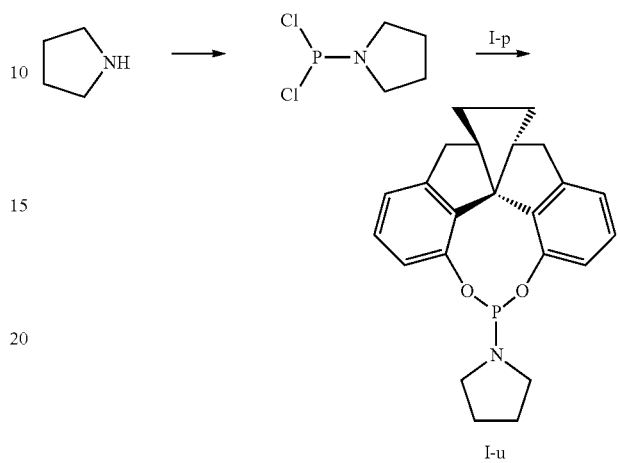

Into an anhydrous anaerobic treatment Schlenk bottle (100 mL), was added THF (30 mL) and pyrrolidine (20.0 mmol), the temperature was cooled to −78° C., n-BuLi (2.4 M in Hexanes) (9.17 mL, 22 mmol)was added by dropwise and the temperature was slowly increased to room temperature after dropping. Into another anhydrous anaerobic treatment Schlenk bottle, was added THF (10 mL) and PCl$_3$ (2.27 ml), the temperature was cooled to −78° C. Take lithium amine solution to the THF solution of PCl$_3$, the temperature was increased to room temperature slowly and stir for 12 hrs. The reaction system was depressured to remove the solvent, the reaction mixture was washed with THF (10 mL×3) and dried on to remove the excess PCl$_3$ then THF was added to form a solution.

Into an anhydrous anaerobic treatment Schlenk bottle (15 mL), were added spirobiindane-7,7'-diol I-p(0.55 mmol), THF (5.0 ml) and Et$_3$N (0.40ml) under the argon atmosphere, the temperature was cooled to 0° C. Then was added dimethylphosphoramidous dichloride slowly(1.70 mL). After finishing dropping, the temperature was warmed to room temperature slowly, the reaction mixture was stirred for a reaction hour of 12 hrs at room temperature, then the reaction was stopped. The reaction system was depressured to remove most of the solvent. The silica gel column was flushed with solvent (petroleum ether/three ethylamine=20:1),the residue was separated and purified by silica gel column chromatography(petroleum ether/ethyl acetate=20:1), the solid product was obtained after drying by oil pump (1R, 2R, 2'R)-I-u. white solid, yield 49%, M.p. 87-88° C., [α]$_D^{20}$ =−237.2° (c 0.565, CHCl$_3$); $^1$H NMR (400 MHz, CDCl$_3$) δ7.18 (t, J=8.0 Hz, 1 H), 7.08 (t, J=8.0 Hz, 1 H), 6.93-6.85 (m, 3 H), 6.57 (d, J=8.0 Hz,1 H), 3.27-3.17 (m, 2 H), 2.89-2.78 (m, 4 H), 2.73 (dd, J=17.2, 5.2 Hz, 2 H), 2.34-2.26 (m, 2 H), 1.99-1.85 (m, 2 H), 1.68-1.64 (m, 4 H), 1.55-1.52 (m, 2 H); $^{13}$C NMR (100 MHz, CDCl$_3$) δ149.67 (d, J=4.8 Hz), 146.13 (d, J=5.9 Hz), 145.48 (d, J=2.0 Hz), 144.96, 142.82 (d, J=3.6 Hz), 141.21 (d, J=1.2 Hz), 128.75 (d, J=2.0 Hz), 128.00, 121.69 (d, J=1.6 Hz), 120.90 (d, J=6.3 Hz), 120.47 (d, J=2.4 Hz), 119.36 (d, J=0.8 Hz), 71.34, 53.18, 52.68 (d, J=1.2 Hz), 45.25, 45.10, 40.90, 40.52, 31.51, 31.32, 25.80, 25.75; $^{31}$P NMR (161 MHz, CDCl$_3$)

δ124.43; IR (neat) v 2922, 2850, 1732, 1582, 1460, 1293, 1227, 1206, 1075, 1006, 981, 804, 780, 726, 676 cm$^{-1}$; EI-MS (70 eV), m/z: 377 ([M]$^+$), 348, 308, 280, 202, 189, 101, 70, 43; HRMS-EI (m/z): calcd. for $C_{23}H_{24}NO_2P$: 377.1545, found: 377.1543.

All the documents mentioned in the present invention are incorporated herein by reference, as if each of them is individually incorporated.

In addition, it should be understood that after reading the above teaching contents of the present invention. Having read the above described teaching of the invention, one skilled in the art could make various changes or modifications to the present invention, it should be pointed out that all similar, equivalent replacements and modifications become apparent to those skilled in the art, and they are deemed to be within the spirit, scope and contents of the present invention and also the attached claims.

The invention claimed is:

1. A chiral fused ring spirobiindane skeleton compound of formula I,

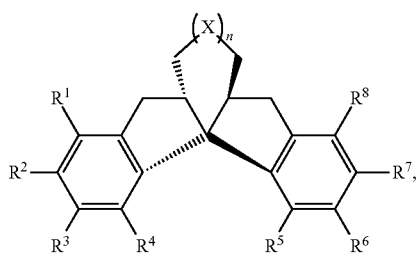

wherein $R^1$, $R^2$, $R^3$, $R^4$, $R^5$, $R^6$, $R^7$, and $R^8$ are each independently selected from H, $C^1$-$C^{10}$ alkyl, $C^1$-$C^4$ alkoxy, aryl, and hydroxyl, with the proviso that $R^1$, $R^2$, $R^3$, $R^4$, $R^5$, $R^6$, $R^7$, and $R^8$ are not simultaneously hydrogen;

or, wherein $R^1$, $R^4$, $R^5$, and $R^8$ are each independently selected from H, $C^1$-$C^{10}$ alkyl, $C^1$-$C^4$ alkoxy, aryl, and hydroxyl, $R^2$ and $R^3$ together with carbon atoms on a molecular skeleton to which they are attached form an aromatic ring, and the aromatic ring is fused with a phenyl ring in which the carbon atoms on the molecular skeleton attached to $R^2$ and $R^3$ are located to form a fused ring, and $R^6$ and $R^7$ together with carbon atoms on a molecular skeleton to which they are attached form an aromatic ring, and the aromatic ring is fused with a phenyl ring in which the carbon atoms on the molecular skeleton attached to $R^6$ and $R^7$ are located to form a fused ring;

wherein X is $CY^1Y^2$, $NY^1$, O, or S, n=1, $Y^1$ and $Y^2$ are each independently selected from H, $C_1$-$C_{10}$ alkyl, $C_3$-$C_{10}$ cycloalkyl, aryl, and $C_1$-$C_4$ alkoxy, and wherein $R^1$ and $R^8$ are the same, $R^2$ and $R^7$ are the same, $R^3$ and $R^6$ are the same, and $R^4$ and $R^5$ are the same.

2. The compound of claim 1, wherein, when $R^1$, $R^2$, $R^3$, $R^4$, $R^5$, $R^6$, $R^7$ and $R^8$ are each independently $C_1$-$C_{10}$ alkyl, the $C_1$-$C_{10}$ alkyl is $C_1$-$C_6$ alkyl;

when $R^1$, $R^2$, $R^3$, $R^4$, $R^5$, $R^6$, $R^7$ and $R^8$ are each independently $C_1$-$C_4$ alkoxy, the $C_1$-$C_4$ alkoxy is $C_1$-$C_3$ alkoxy;

when $R_1$, $R^2$, $R^3$, $R^4$, $R^5$, $R^6$, $R^7$ and $R^8$ are each independently aryl, the aryl is $C_6$-$C_{20}$ aryl;

when $R^2$ and $R^3$ together with the carbon atoms on the molecular skeleton to which they are attached form the aromatic ring, the aromatic ring is $C_6$-$C_{20}$ aromatic ring;

when $R^6$ and $R^7$ together with the carbon atoms on the molecular skeleton to which they are attached form the aromatic ring, the aromatic ring is $C_6$-$C_{20}$ aromatic ring;

when $Y^1$ and $Y^2$ are each independently $C_1$-$C_{10}$ alkyl, the $C_1$-$C_{10}$ alkyl is $C_1$-$C_4$ alkyl;

when $Y^1$ and $Y^2$ are each independently $C_3$-$C_{10}$ cycloalkyl, the $C_3$-$C_{10}$ cycloalkyl is $C_3$-$C_6$ cycloalkyl;

when $Y^1$ and $Y^2$ are each independently aryl, the aryl is $C_6$-$C_{20}$ aryl; or when $Y^1$ and $Y^2$ are each independently $C_1$-$C_4$ alkoxy, the $C_1$-$C_4$ alkoxy is methoxyl or ethoxyl.

3. The compound of claim 2, wherein:

when $R^1$, $R^2$, $R^3$, $R^4$, $R^5$, $R^6$, $R^7$ and $R^8$ are each independently $C_1$-$C_6$ alkyl, the $C_1$-$C_6$ alkyl is $C_1$-$C_3$ alkyl;

when $R^1$, $R^2$, $R^3$, $R^4$, $R^5$, $R^6$, $R^7$ and $R^8$ are each independently $C_1$-$C_3$ alkoxy, the $C_1$-$C_3$ alkoxy is methoxyl, ethoxyl or propoxy;

when $R^1$, $R^2$, $R^3$, $R^4$, $R^5$, $R^6$, $R^7$ and $R^8$ are each independently $C_6$-$C_{20}$ aryl, the $C_6$-$C_{20}$ aryl is $C_6$-$C_{12}$ aryl;

when $R^2$ and $R^3$ together with the carbon atoms on the molecular skeleton to which they are attached form the $C_6$-$C_{20}$ aromatic ring, the $C_6$-$C_{20}$ aromatic ring is $C_6$-$C_{12}$ aromatic ring;

when $R^6$ and $R^7$ together with the carbon atoms on the molecular skeleton to which they are attached form the $C_6$-$C_{20}$ aromatic ring, the $C_6$-$C_{20}$ aromatic ring is $C_6$-$C_{12}$ aromatic ring;

when $Y^1$ and $Y^2$ are each independently $C_1$-$C_4$ alkyl, the $C_1$-$C_4$ alkyl is methyl, ethyl, propyl or tert-butyl;

when $Y^1$ and $Y^2$ are each independently $C_3$-$C_6$ cycloalkyl, the $C_3$-$C_6$ cycloalkyl is cyclopropyl;

or when $Y^1$ and $Y^2$ are each independently $C_6$-$C_{20}$ aryl, the $C_6$-$C_{20}$ aryl is $C_6$-$C_{12}$ aryl.

4. The compound of claim 3, wherein:

when $R^1$, $R^2$, $R^3$, $R^4$, $R^5$, $R^6$, $R^7$ and $R^8$ are each independently $C_1$-$C_3$ alkyl, the $C_1$-$C_3$ alkyl is methyl, ethyl or propyl;

when $R^1$, $R^2$, $R^3$, $R^4$, $R^5$, $R^6$, $R^7$ and $R^8$ are each independently $C_6$-$C_{12}$ aryl, the $C_6$-$C_{12}$ aryl is phenyl or naphthyl;

when $R^2$ and $R^3$ together with the carbon atoms on the molecular skeleton to which they are attached form the $C_6$-$C_{12}$ aromatic ring, the $C_6$-$C_{12}$ aromatic ring is benzene ring or naphthalene ring;

when $R^6$ and $R^7$ together with the carbon atoms on the molecular skeleton to which they are attached form the $C_6$-$C_{12}$ aromatic ring, the $C_6$-$C_{12}$ aromatic ring is benzene ring or naphthalene ring; or when $Y^1$ and $Y^2$ are each independently $C_6$-$C_{12}$ aryl, the $C_6$-$C_{12}$ aryl is phenyl or naphthyl.

5. The compound of claim 1 is
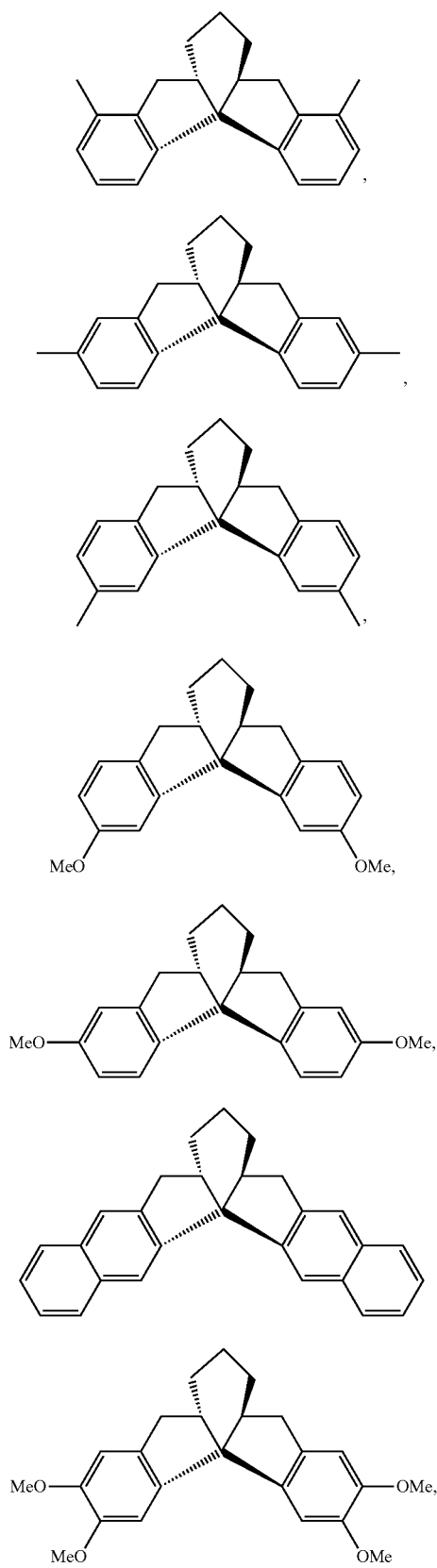

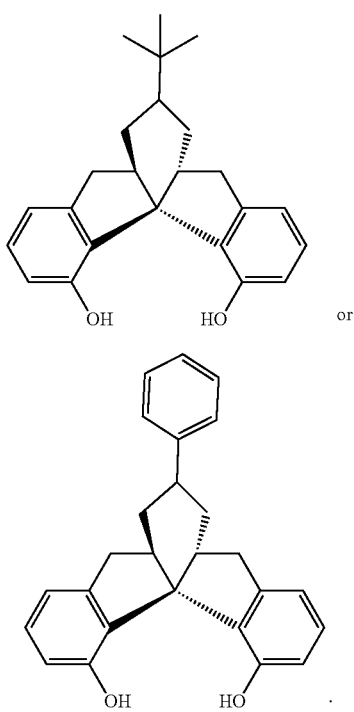

6. A method for preparing the chiral fused ring spirobiindane skeleton compound of formula I according to claim 1, comprising following steps:
subjecting a compound of formula III to a intramolecular Friedel-Crafts reaction under a catalyst in a solvent to form the compound of formula I; wherein the catalyst is Bronsted acid or Lewis acid,

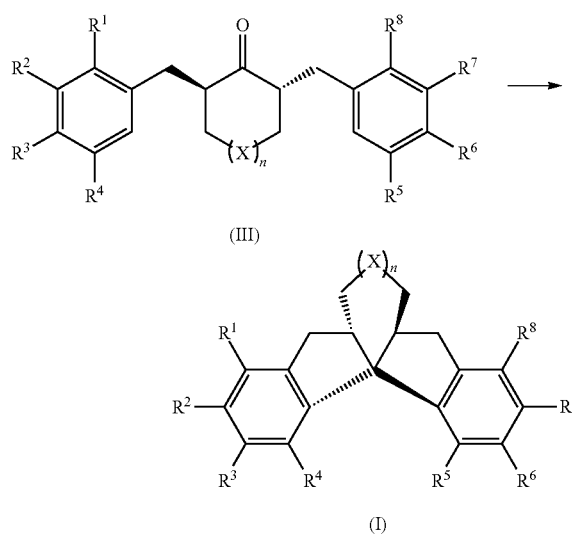

7. The method according to claim 6, wherein,
the Bronsted acid is one or more selected from the group consisting of hydrochloric acid, phosphoric acid, polyphosphoric acid, methanesulfonic acid, trifluoromethanesulfonic acid, acetic acid, trifluoroacetic acid, p-toluene sulfonic acid, and phosphotungstic acid; the Lewis acid is one or more selected from the group consisting of scandium triflate, aluminium trichloride, stannic chloride, ferric trichloride, boron trifluoride, titanium tetrachloride, tetraisopropyl titanium, indium trifluoromethyl sulfonate, and copper trifluoromethyl sulfonate;

and/or, the method for preparing the compound of formula I further comprises following steps:
mixing the solvent with the compound of formula III, adding the catalyst to react for 1-100 minutes at a temperature of 0° C., naturally rising the temperature to 15-40° C. and reacting for 1-20 hrs;

and/or, the intramolecular Friedel-Crafts reaction is carried out under anhydrous and anaerobic conditions;

and/or, the intramolecular Friedel-Crafts reaction is carried out under protective gas;

and/or, a molar ratio of the compound of formula III to the catalyst is 100:1-1:100;

and/or, the solvent of the intramolecular Friedel-Crafts reaction is one or more selected from the group consisting of aromatic solvent, halogenated hydrocarbon solvent, ether solvent, alcohol solvent, amide solvent, and sulfoxide solvent;

and/or, a molar volume ratio of the compound of formula III to the solvent of the intramolecular Friedel-Crafts reaction is 0.02 mol/L-0.2 mol/L;

and/or, a reaction temperature of the intramolecular Friedel-Crafts reaction is −40° C.-100° C.;

and/or, a reaction time of the intramolecular Friedel-Crafts reaction is 0.1-48 hrs.

8. The method according to claim 6 or 7, further comprising following steps: subjecting a compound of formula II to an asymmetric hydrogenation reaction with hydrogen in presence of a catalyst in a solvent to form the compound of formula III:

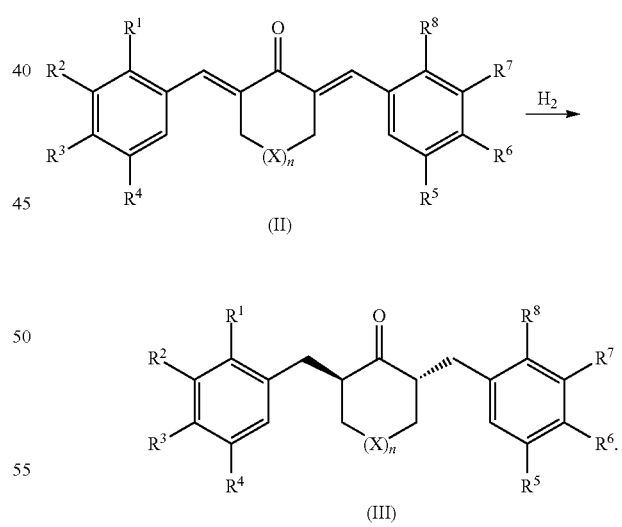

9. The method according to claim 8, wherein,
the catalyst of the asymmetric hydrogenation reaction is one or more selected from the group consisting of a transition metal complex of ruthenium, rhodium, iridium, and palladium;

the transition metal complex is chiral or non-chiral;

and/or, a molar ratio of the catalyst to the compound of formula II is 0.0001-0.1;

and/or, the solvent of the asymmetric hydrogenation reaction is one or more selected from the group consisting of halogenated hydrocarbon solvent, aromatic solvent, ether solvent, alcohol solvent, amide solvent and sulfoxide solvent;

and/or, a volume mass ratio of the solvent of the asymmetric hydrogenation reaction to the compound of formula II is 1 ml/g-20 ml/g;

and/or, a hydrogen pressure of the asymmetric hydrogenation reaction is 1-100 atm;

and/or, a reaction temperature of the asymmetric hydrogenation reaction is −78° C.-80° C.;

and/or, a reaction time of the asymmetric hydrogenation reaction is 1-48 hrs;

and/or, after completion of the asymmetric hydrogenation reaction, the reaction system containing the compound of formula III, without post treatment, is directly mixed with the solvent and the catalyst of the intramolecular Friedel-Crafts reaction to carry out the intramolecular Friedel-Crafts reaction.

10. The method according to claim 8, further comprising following steps: subjecting compounds of formulae V, VI and VII to an aldol condensation reaction as shown below in a solvent to obtain the compound of formula II:

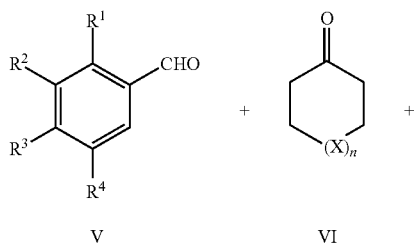

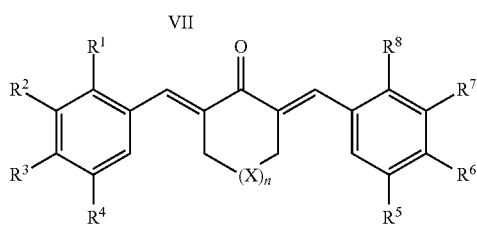

11. The method according to claim 10, wherein, the aldol condensation reaction is carried out under alkaline condition;

and/or, the solvent of the aldol condensation reaction is a mixture of alcohol solvent and water;

and/or, a volume molar ratio of the solvent of the aldol condensation reaction to the compound of formula VI is 10000 ml/mol -1 ml/mol;

and/or, a reaction temperature of the aldol condensation reaction is 10° C.-35° C.;

and/or, a reaction time of the aldol condensation reaction is 1-12 hrs.

* * * * *